United States Patent
Jackson et al.

(10) Patent No.: US 12,414,801 B2
(45) Date of Patent: Sep. 16, 2025

(54) SPINAL FIXATION SYSTEM WITH MODULAR RECEIVER SUB-ASSEMBLIES FOR CONNECTING WITH BI-SPHERICAL UNIVERSAL SHANK HEADS

(71) Applicant: Roger P. Jackson, Prairie Village, KS (US)

(72) Inventors: Roger P. Jackson, Prairie Village, KS (US); James L. Surber, Kansas City, KS (US); Nathaniel D. Ginzton, Boise, ID (US)

(*) Notice: Subject to any disclaimer, the term of this patent is extended or adjusted under 35 U.S.C. 154(b) by 129 days.

(21) Appl. No.: 18/501,495

(22) Filed: Nov. 3, 2023

(65) Prior Publication Data
US 2024/0252212 A1    Aug. 1, 2024

Related U.S. Application Data

(60) Provisional application No. 63/382,277, filed on Nov. 3, 2022.

(51) Int. Cl.
*A61B 17/70*    (2006.01)
*A61B 17/86*    (2006.01)

(52) U.S. Cl.
CPC ...... *A61B 17/7037* (2013.01); *A61B 17/7035* (2013.01); *A61B 17/7038* (2013.01); *A61B 17/8605* (2013.01); *A61B 17/7005* (2013.01); *A61B 17/8625* (2013.01)

(58) Field of Classification Search
CPC ......... A61B 17/7032–17/7038; A61B 17/8605
See application file for complete search history.

(56) References Cited

U.S. PATENT DOCUMENTS

| | | | |
|---|---|---|---|
| 5,547,873 | A  | 8/1996  | Magneson et al. |
| 5,690,630 | A  | 11/1997 | Errico et al. |
| 6,063,090 | A  | 5/2000  | Schläpfer |
| 6,069,090 | A  | 5/2000  | Eriguchi |
| 6,090,111 | A  | 7/2000  | Nichols |
| 6,146,383 | A  | 11/2000 | Studer et al. |
| 6,485,491 | B1 | 11/2002 | Farris et al. |
| 6,530,929 | B1 | 3/2003  | Justis et al. |
| 6,837,889 | B2 | 1/2005  | Shluzas |
| 6,905,500 | B2 | 6/2005  | Jeon et al. |

(Continued)

*Primary Examiner* — Julianna N Harvey
(74) *Attorney, Agent, or Firm* — Polsinelli PC

(57) ABSTRACT

A spinal fixation system includes a plurality of bone anchors, each having an anchor portion and a shank head with an upper spherical surface having a first diameter extending downward to an inner edge of an annular shelf spaced below a hemisphere plane, and a lower spherical surface having a second diameter greater than the first diameter extending downward from an outer edge of the annular shelf toward a neck extending between the shank head and anchor portion. The system also includes both pivoting and non-pivoting receiver sub-assemblies, with each receiver sub-assembly including a receiver having a central bore with a seating surface adjacent a bottom opening and a channel for receiving a rod. Each receiver sub-assembly also includes one of a multiplanar retaining structure, a monoplanar retaining structure, or a monoaxial retaining structure positioned therein and slidably engageable with the seating surface after capturing the shank head upon its uploading through the bottom opening.

21 Claims, 38 Drawing Sheets

(56) References Cited

U.S. PATENT DOCUMENTS

| | | |
|---|---|---|
| 6,945,975 B2 | 9/2005 | Dalton |
| 7,087,057 B2 | 8/2006 | Konieczynski et al. |
| 7,144,396 B2 | 12/2006 | Shluzas |
| 7,377,923 B2 | 5/2008 | Purcell et al. |
| 7,479,156 B2 | 1/2009 | Lourdel et al. |
| 7,604,655 B2 | 10/2009 | Warnick |
| 7,749,258 B2 | 7/2010 | Biedermann et al. |
| 7,776,067 B2 | 8/2010 | Jackson |
| 7,789,900 B2 | 9/2010 | Levy et al. |
| 7,811,310 B2 | 10/2010 | Baker et al. |
| 7,833,251 B1 | 11/2010 | Ahlgren et al. |
| 7,901,436 B2 | 3/2011 | Baccelli |
| 7,942,909 B2 | 5/2011 | Hammill, Sr. et al. |
| 7,947,065 B2 | 5/2011 | Hammill, Sr. et al. |
| 7,951,172 B2 | 5/2011 | Chao et al. |
| 7,951,173 B2 | 5/2011 | Hammill, Sr. et al. |
| 7,967,850 B2 | 6/2011 | Jackson |
| 8,075,599 B2 | 12/2011 | Johnson et al. |
| 8,075,603 B2 | 12/2011 | Hammill, Sr. et al. |
| 8,197,518 B2 | 6/2012 | Hammill, Sr. et al. |
| 8,308,782 B2 | 11/2012 | Jackson |
| 8,339,922 B2 | 12/2012 | Hotta et al. |
| 8,353,932 B2 | 1/2013 | Jackson |
| 8,361,123 B2 | 1/2013 | Fanger et al. |
| 8,366,753 B2 | 2/2013 | Jackson |
| 8,382,805 B2 | 2/2013 | Wang et al. |
| 8,394,108 B2 | 3/2013 | McLean et al. |
| 8,449,578 B2 | 5/2013 | Keiser et al. |
| 8,562,652 B2 | 10/2013 | Biedermann et al. |
| 8,628,558 B2 | 1/2014 | Harvey et al. |
| 8,663,298 B2 | 3/2014 | Keyer et al. |
| 8,696,712 B2 | 4/2014 | Biedermann et al. |
| 8,876,869 B1 | 11/2014 | Schafer et al. |
| 8,882,817 B2 | 11/2014 | Jones et al. |
| 8,888,827 B2 | 11/2014 | Harper et al. |
| 8,906,068 B1 * | 12/2014 | Bedor ................. A61B 17/7037 606/267 |
| 8,986,349 B1 | 3/2015 | German et al. |
| 8,998,959 B2 | 4/2015 | Jackson et al. |
| 9,044,272 B2 | 6/2015 | Shaffrey et al. |
| 9,060,814 B2 | 6/2015 | Doubler et al. |
| 9,119,674 B2 | 9/2015 | Matthis |
| 9,254,150 B2 | 2/2016 | Biedermann et al. |
| 9,358,047 B2 | 6/2016 | Mishra et al. |
| 9,439,680 B2 | 9/2016 | Biedermann et al. |
| 9,451,993 B2 | 9/2016 | Jackson et al. |
| 9,453,526 B2 | 9/2016 | Black et al. |
| 9,486,246 B2 | 11/2016 | Biedermann et al. |
| 9,492,204 B2 | 11/2016 | Biedermann et al. |
| 9,526,529 B2 | 12/2016 | Charvet |
| 9,572,599 B1 | 2/2017 | Casey et al. |
| 9,572,600 B2 | 2/2017 | Biedermann et al. |
| 9,615,858 B2 | 4/2017 | Doubler et al. |
| 9,649,134 B2 | 5/2017 | Hannen |
| 9,724,145 B2 | 8/2017 | Spratt et al. |
| 9,763,702 B2 | 9/2017 | Schlaepfer et al. |
| D799,949 S | 10/2017 | Stevenson et al. |
| 9,775,660 B2 | 10/2017 | Spratt et al. |
| 9,918,745 B2 | 3/2018 | Jackson et al. |
| 9,924,971 B2 | 3/2018 | Biedermann et al. |
| 9,924,975 B2 | 3/2018 | Jackson et al. |
| 10,028,770 B2 | 7/2018 | Rezach et al. |
| 10,052,136 B2 | 8/2018 | Nelson |
| 10,058,354 B2 | 8/2018 | Jackson et al. |
| 10,064,657 B2 | 9/2018 | Spitler |
| 10,117,680 B2 | 11/2018 | Trautwein et al. |
| 10,130,396 B2 | 11/2018 | Vedula et al. |
| 10,172,647 B2 | 1/2019 | Elsbury |
| 10,188,432 B2 | 1/2019 | Jackson et al. |
| 10,194,951 B2 | 2/2019 | Jackson et al. |
| 10,285,738 B1 | 5/2019 | Doubler et al. |
| 10,335,203 B2 | 7/2019 | Fiechter et al. |
| 10,363,070 B2 | 7/2019 | Jackson et al. |
| 10,507,043 B1 | 12/2019 | Gladieux |
| 10,517,645 B2 | 12/2019 | van der Pol |
| 10,695,100 B2 | 6/2020 | May et al. |
| 10,765,455 B2 | 9/2020 | Jackson et al. |
| 10,792,074 B2 | 10/2020 | Jackson |
| 11,020,150 B1 | 6/2021 | Doubler et al. |
| 11,141,199 B1 | 10/2021 | Doubler et al. |
| 11,219,470 B2 | 1/2022 | Avidano et al. |
| 11,234,738 B2 | 2/2022 | Jackson et al. |
| 11,234,745 B2 | 2/2022 | Jackson |
| 11,304,732 B2 | 4/2022 | Mueller et al. |
| 11,571,244 B2 | 2/2023 | Loftis et al. |
| 2003/0004512 A1 * | 1/2003 | Farris ................. A61B 17/7055 606/328 |
| 2003/0153911 A1 | 8/2003 | Shluzas |
| 2005/0261687 A1 | 11/2005 | Garamszegi et al. |
| 2006/0036252 A1 * | 2/2006 | Baynham ........... A61B 17/7035 606/328 |
| 2006/0161152 A1 | 7/2006 | Ensign et al. |
| 2006/0161153 A1 | 7/2006 | Hawkes et al. |
| 2006/0241603 A1 * | 10/2006 | Jackson ............. A61B 17/7037 606/304 |
| 2006/0276791 A1 * | 12/2006 | Shluzas ............. A61B 17/7002 606/301 |
| 2007/0270813 A1 | 11/2007 | Garamszegi |
| 2007/0270831 A1 | 11/2007 | Dewey et al. |
| 2008/0147129 A1 | 6/2008 | Biedermann et al. |
| 2010/0152787 A1 * | 6/2010 | Walsh ................ A61B 17/7037 606/305 |
| 2010/0331887 A1 | 12/2010 | Jackson et al. |
| 2011/0040338 A1 * | 2/2011 | Jackson ............. A61B 17/7032 606/305 |
| 2011/0178558 A1 * | 7/2011 | Barry ................ A61B 17/7037 606/302 |
| 2011/0178559 A1 * | 7/2011 | Barry ................ A61B 17/8605 606/305 |
| 2012/0310284 A1 | 12/2012 | Gerchow |
| 2013/0096621 A1 * | 4/2013 | Biedermann ...... A61B 17/7037 606/279 |
| 2013/0103098 A1 | 4/2013 | Jackson et al. |
| 2013/0144346 A1 | 6/2013 | Jackson et al. |
| 2014/0025119 A1 | 1/2014 | Biedermann et al. |
| 2014/0188173 A1 * | 7/2014 | Mishra ............... A61B 17/7038 606/278 |
| 2014/0214084 A1 * | 7/2014 | Jackson ............. A61B 17/7037 606/267 |
| 2014/0343617 A1 * | 11/2014 | Hannen ............. A61B 17/8605 606/306 |
| 2015/0112390 A1 * | 4/2015 | Fang .................. A61B 17/7037 606/279 |
| 2015/0320465 A1 * | 11/2015 | Butler ............... A61B 17/8605 29/428 |
| 2016/0317206 A1 | 11/2016 | Rezach et al. |
| 2017/0333085 A1 * | 11/2017 | Jackson ............. A61B 17/7038 |
| 2018/0125535 A1 * | 5/2018 | Faulhaber .......... A61B 17/7032 |
| 2018/0263665 A1 * | 9/2018 | Yacoub .............. A61B 17/8615 |
| 2018/0325569 A1 * | 11/2018 | Ramsay ............. A61B 17/7037 |
| 2021/0015521 A1 * | 1/2021 | Biedermann ...... A61B 17/7032 |
| 2022/0039837 A1 * | 2/2022 | Biedermann ...... A61B 17/7032 |
| 2023/0225768 A1 * | 7/2023 | Jackson ............. A61B 17/7038 606/266 |

* cited by examiner

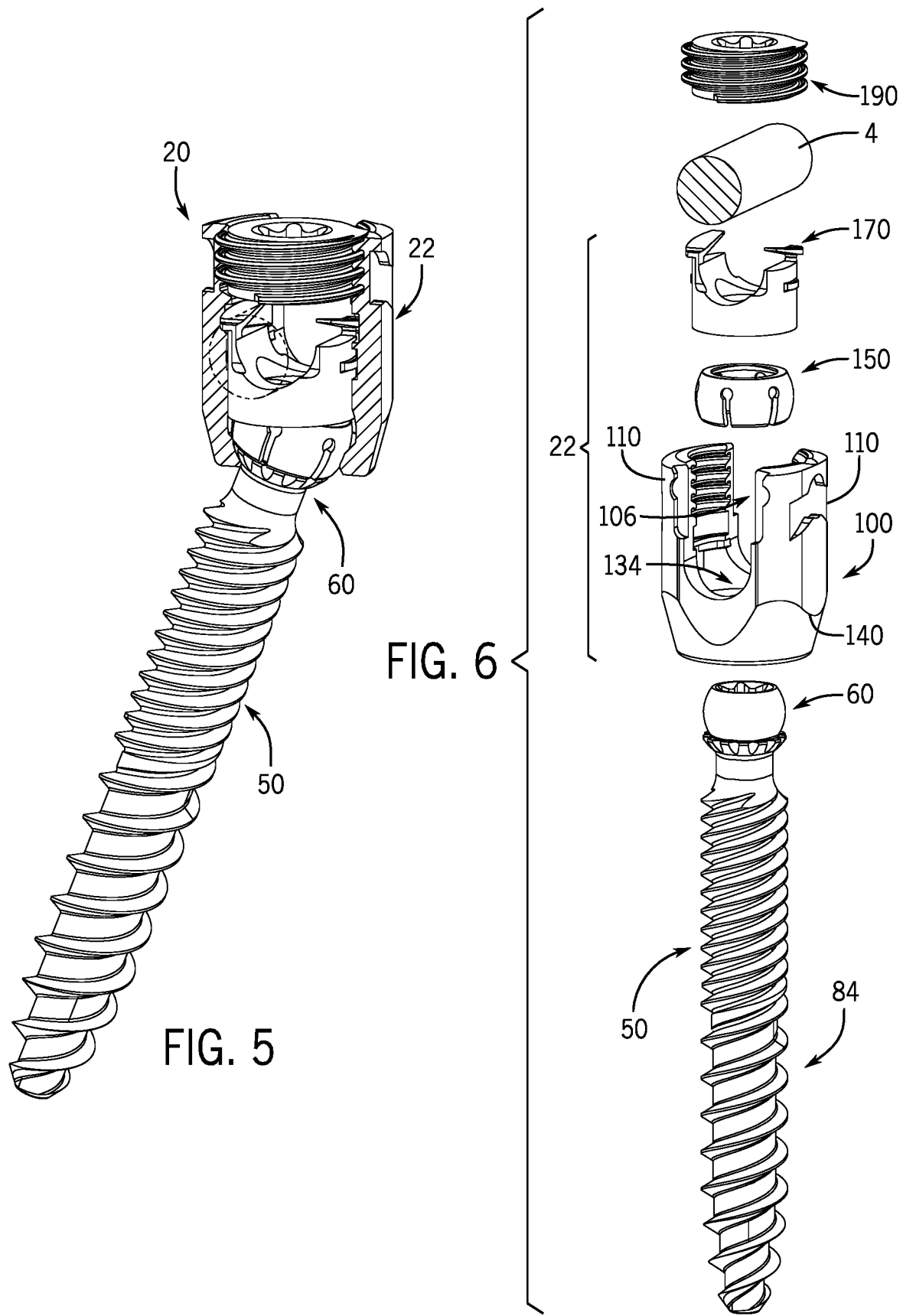

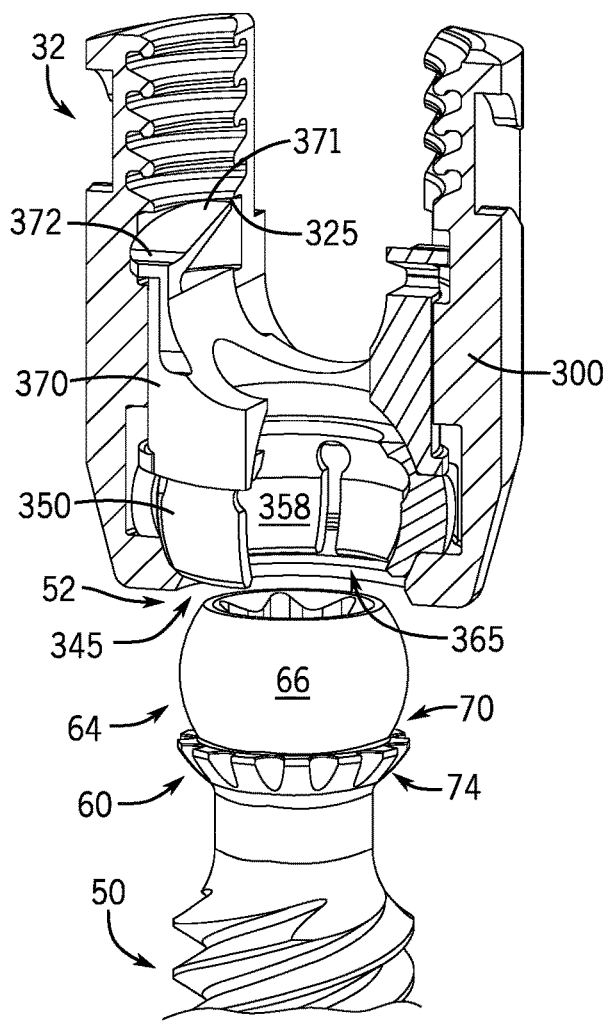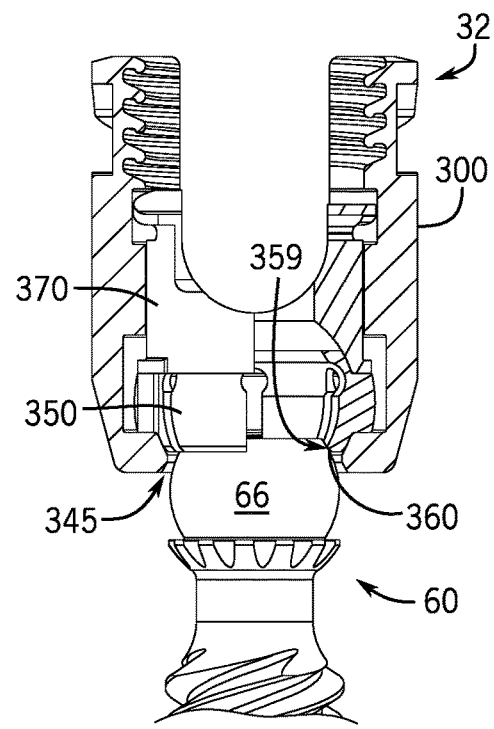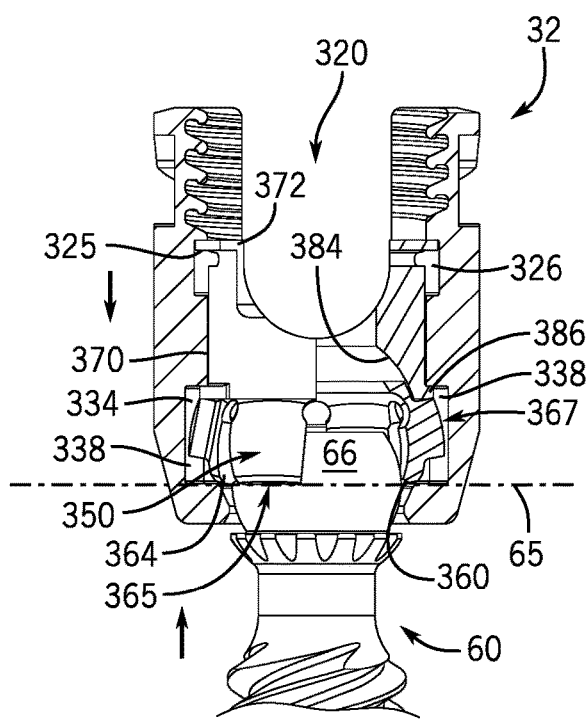
FIG. 84
FIG. 85
FIG. 86

SPINAL FIXATION SYSTEM WITH MODULAR RECEIVER SUB-ASSEMBLIES FOR CONNECTING WITH BI-SPHERICAL UNIVERSAL SHANK HEADS

CROSS-REFERENCE TO RELATED APPLICATIONS

This application claims the benefit of U.S. Provisional Application No. 63/382,277, filed Nov. 3, 2022, which is incorporated by reference in its entirety herein and for all purposes.

FIELD

The present disclosure relates generally to modular spinal implant assemblies utilizing universal shank heads that are configured for connection with a collection or array of pivoting and non-pivoting but axially rotatable (e.g. monoaxial) receiver sub-assemblies having different functionalities, and their use in surgery involving vertebral body stabilizations with spinal fixation systems.

BACKGROUND

Spinal implants in general, and bone anchors or screws in particular, are used in many types of spinal surgery in order to secure various implants to vertebrae along the spinal column for the purposes of treating spinal disorders, such as degenerative conditions and deformities, and also for stabilizing and/or adjusting spinal alignment. A common mechanism for providing vertebral support is to implant the bone screws into certain bones which then, in turn, support a longitudinal structure such as an elongate rod, or are supported by such a rod. Although both closed-ended and open-ended spinal implants, such as bone screws and hooks, are known, the open-ended spinal implants can be particularly well suited for connections to rods and connector arms because such rods or arms do not need to be passed through a closed bore, but rather can be laid or urged into an open channel within the head or receiver of such a screw, hook, or connector. For example, open-ended bone screws generally comprise an anchor portion, such as a threaded shank, connected to a head or receiver having a pair of upwardly-projecting branches or arms which form a yoke that defines a slot or channel configured to receive the rod. The slot or channel could have different shapes, such as, a U-shape or a square shape. Moreover, the threaded shanks of the bone screws can also be replaced with hooks or other types of bone anchors or connectors to form a variety of different types of spinal implants, also having open ends for receiving rods or portions of other structures, and wherein such implants can facilitate surgical techniques performed with different spinal fixation systems.

Early bone screws used in spinal surgery generally had a yoke-shaped 'head' that was integrally formed or "fixed" with the threaded shank, and therefore immovable. Because the fixed head could not be moved relative to the shank, these fixed bone screws needed to be favorably positioned in the spine. Otherwise, the elongate rod would need to be bent in order for it to be placed within the rod-receiving channels of multiple implants due to their alignment. Given the highly curved shape of the spines of some patients, however, this is sometimes very difficult or impossible to do. Therefore, polyaxial (i.e. multiplanar), uni-planar (i.e. monoplanar), and/or translatable pivotal bone screws or bone anchor assemblies, were developed and are now commonly preferred. Open-ended polyaxial bone screw assemblies typically allow for pivoting and rotation of the connected but completely separate yoke-shaped receiver or receiver sub-assembly about an enlarged spherical 'head' or upper capture portion of the threaded shank or bone anchor in one or more planes, until a desired rotational and pivotal position of the receiver is achieved relative to the shank. This can be accomplished by manipulating the position of the receiver relative to the shank during a final stage of a medical procedure when the elongate rod or other longitudinal connecting member is inserted into the receiver or receiver sub-assembly, followed by a locking set screw, a plug, a closure, or other type of locking mechanism known in the art.

It is understood that spinal fixation systems generally include a variety of components that require some assembly, such as the various types of bone anchors, the rods or connector arms, and the closures or plugs with the receivers or receiver sub-assemblies, with each component having specific features with respect to structure and function. Moreover, the receiver sub-assemblies can further include components in addition to the receiver itself, such as pressure inserts, spring rings, separate retainers, and other components of different types that are operable to connect these receiver sub-assemblies with the heads of the bone anchors. The pressure inserts, rings, retainers, and other components can be pre-assembled together within the receivers to form the receiver sub-assemblies that are ready for further assemblage with the bone anchors, and eventually with the rods or connector arms and the closures or plugs.

Some designs provide for the threaded shanks or other types of bone anchor to be bottom loaded into the receiver sub-assemblies. With bottom loaded bone anchor assemblies, for example, some designs known in the art require a separate retainer to hold the shank within the receiver, with the receiver having a bottom opening large enough to allow for the head or upper capture portion of the threaded shank or bone anchor to be uploaded into the central bore or cavity of the receiver. Other types of bottom loaded bone anchor assemblies do not include the separate retainer, however, and instead include a receiver having a lower portion with a bottom opening that is configured to directly threadably mate with the head or upper capture portion of the shank that can be configured as a threaded spherical head to provide for polyaxial or multiplanar motion.

Further to the above, bottom loaded bone anchor assemblies can also be fully assembled by the spinal company or distributor before being shipped to a hospital, so as to help with inventory management, or can be shipped as a modular array of multiple separate and different shanks and a fewer number of pre-assembled receiver sub-assemblies that can then be fully assembled, for example, at the hospital or surgical center during a surgery, thereby saving costs. Additionally, the modular spinal implants can be fully assembled at the hospital either before insertion into the patient, or after the threaded shank or bone anchor has been inserted into the patient, such as with robotic assistance or directly by a robot. The different techniques or approaches for the insertion and assembly of the modular parts of the bone anchor assemblies can be described as ex-vivo and in-vivo, respectively.

SUMMARY

The present disclosure is generally directed to modular spinal fixation systems with bone anchors comprising a certain type of common or universal shank head configured to connect with a wide array of receiver sub-assemblies having different functionalities to form pivotal and non-pivotal bone anchor assemblies with different capabilities. To that purpose, one embodiment of the present disclosure comprises a spinal fixation system for securing an elongate rod to a spine of a patient.

The spinal fixation system includes a plurality of bone anchors, with each bone anchor having a longitudinal axis, a shank head at a proximal end devoid of outer parallel planar side surfaces, an anchor portion opposite the shank head configured for fixation to the bone, and a neck portion extending between the shank head and the anchor portion. Each shank head includes an upper partial spherical portion comprising an upper spherical surface having a first diameter extending downward from an upper end, out and around the hemisphere plane of the upper spherical surface, to a circular inner edge of upward-facing shelf surface of a lower shelf or ledge structure that is spaced below the hemisphere plane, and a lower partial spherical portion comprising a lower spherical surface having a second diameter that is greater than the first diameter and which extends downward from the circular outer edge of the upward-facing shelf surface toward the neck portion that connects the shank head to the anchor portion. In one aspect the upward-facing shelf surface is an annular planar surface extending perpendicular to the longitudinal axis of the bone anchor.

The spinal fixation system also includes an array of receiver sub-assemblies, with each receiver sub-assembly including a receiver with a base portion that defines a lower section of a central bore centered around a vertical centerline axis and communicating with a bottom of the receiver through a bottom opening, and an upper portion having a channel configured to receive the elongate rod describe above. The central bore includes a seating surface adjacent or proximate the bottom opening, and extends upward through the channel to a top of the receiver. Each receiver sub-assembly also includes one of a multiplanar pivoting retaining structure (also known as a cap retainer), a monoplanar pivoting retaining structure or cap retainer, or a non-pivoting or monoaxial retaining structure or cap retainer positioned therein and configured to slidably engage the seating surface after capturing the upper partial spherical portion of a shank head upon its uploading through the bottom opening of the receiver.

Each receiver sub-assembly further includes a pressure insert positionable within the central bore above the retaining structure and having an upper surface configured to engage the elongate rod and a lower end configured to engage the retaining structure. In one aspect the pressure inserts can include a resilient, axially-biasing capability automatically establish a pre-lock friction fit without any further manipulation or deployment of the bone anchor assembly with tooling. In other aspects the pressure inserts can be configured for downward deployment with tooling to the pre-lock friction fit configuration.

After the shank head of the bone anchor is captured by the retaining structure or cap retainer of one of the retainer sub-assemblies, ex-vivo or in-vivo, and to form a bone anchor assembly, the bone anchor is further configured to have frictional axial independent rotation with respect to the receiver sub-assembly, together with one of multiplanar motion or monoplanar motion with respect to the receiver sub-assembly for the pivotal bone anchor assemblies.

At least one additional embodiment of the present disclosure includes non-pivoting receiver sub-assemblies in which the upper ends of the retaining structures and the lower ends of the pressure inserts are configured to form a stepped cylindrical joint when engaged together, with the retaining structures being rotatable about the vertical centerline axis of the receiver relative to the pressure inserts prior to locking the receiver assemblies to the shank heads.

Other additional embodiments of the present disclosure will be better understood upon review of the detailed description set forth below taken in conjunction with the accompanying drawing figures, which are briefly described as follows.

BRIEF DESCRIPTION OF THE DRAWINGS

FIG. 5 is a perspective view of a multiplanar embodiment of a bone anchor assembly in an articulated position or configuration, in accordance with the representative embodiment of the multi-component spinal fixation system shown in FIG. 1.

FIG. 6 is an exploded perspective view of the multiplanar embodiment of the bone anchor assembly shown in FIG. 5.

FIG. 84 is a partially cut-away front perspective view of the monoplanar receiver sub-assembly positioned above the bi-spheric shank head of the universal bone anchor.

FIG. 85 is a partially cut-away front view of the monoplanar receiver sub-assembly moving downward until the bi-spheric shank head engages the cap retainer secured within the receiver by the pressure insert.

FIG. 86 is a partially cut-away front view of the monoplanar receiver sub-assembly continuing to move downward and the cap retainer and pressure insert being pushed upward to their uppermost positions, and the bi-spheric shank head continuing to drive upward as it expands the cap retainer within the internal cavity until reaching the maximum expansion of the cap retainer.

Figure 1:
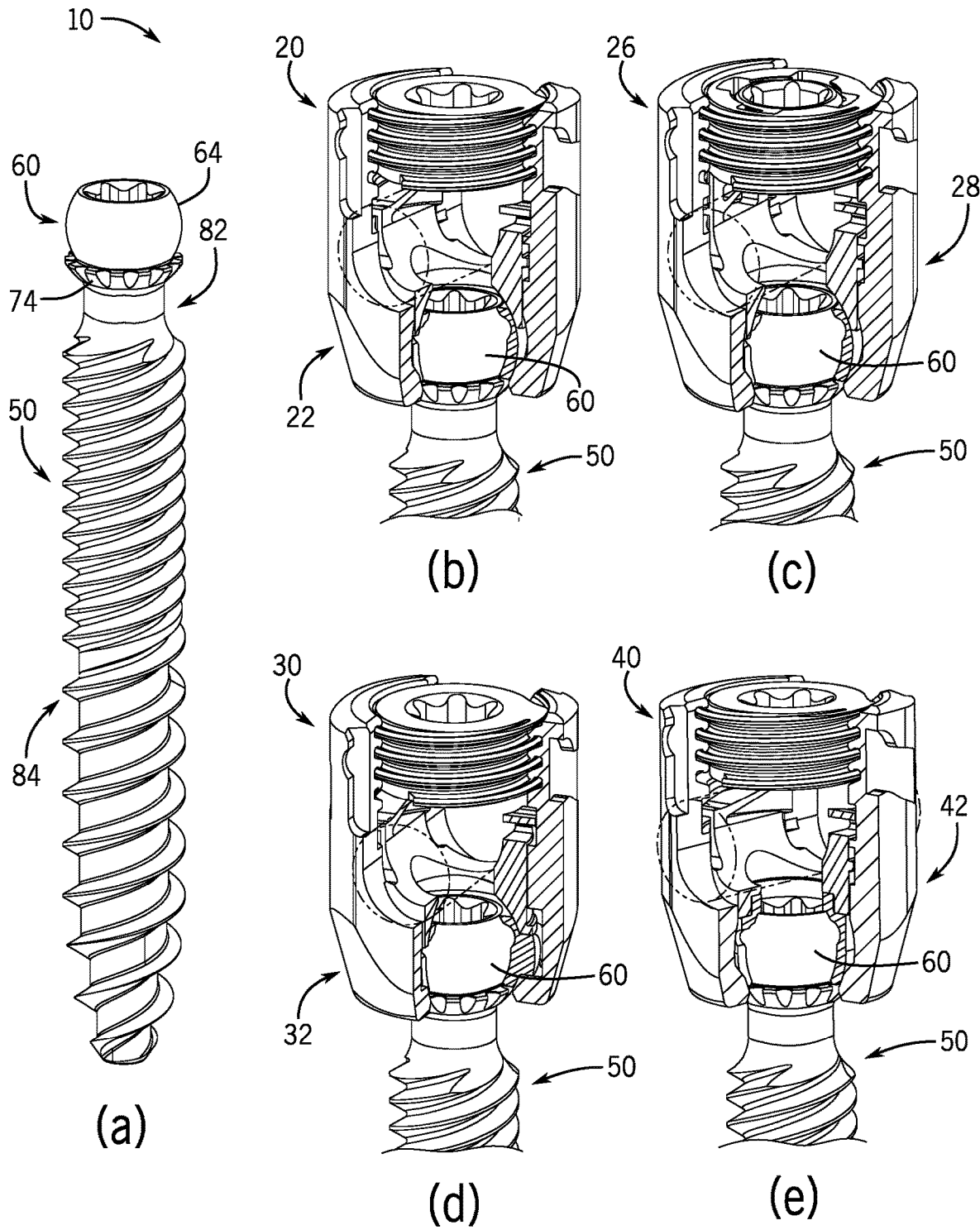
FIG. 1 is a partially cut-away front perspective view of a multi-component spinal fixation system showing four major types of receiver sub-assemblies and a universal bone anchor having a bi-spheric universal shank head, with each receiver sub-assembly having different functionalities and being attachable to the defined common geometry on the upper capture portion of the bone anchor, in accordance with a representative embodiment of the present disclosure.

Those skilled in the art will appreciate and understand that the various features and structures or components of the bone anchor assemblies shown in the drawings described above, together with their relative relationships, interconnections and functions, can be interpreted as being drawn to scale. Nevertheless, it is also understood that the representative embodiments of the present disclosure disclosed and claimed herein are not limited to the precise structures and interrelationships of the features and components shown in the drawing figures, and that the dimensions, relative positions, and interconnections between the illustrated features and components may also be expanded, reduced, re-shaped, or otherwise revised or altered as needed to more clearly illustrate the structure of the embodiments depicted therein or the functions of the various features and components, as described below. Again, it is foreseen that some parts and features are interchangeable in their arrangement between the different embodiments disclosed.

DETAILED DESCRIPTION OF EXEMPLARY EMBODIMENTS

The following description, in conjunction with the accompanying drawings, is provided as an enabling teaching of bone anchors having a representative type of universal shank head, specifically a bi-spheric shank head or capture structure, configured for use with a collection or array of complementary pivotal and non-pivotal receiver sub-assemblies in a modular spinal fixation system. The collection can include different types of receiver sub-assemblies that can be coupled to the universal shank head to form bone anchors having a variety of modes of movement, degrees of freedom, or modalities (with the terms 'mode, 'modality', and 'multi-modal', etc., being used herein to describe the way in which something or somethings move), including but not limited to pivoting and non-pivoting but axially rotatable (e.g. monoaxial) movement. The description also includes one or more methods for assembling and employing the bone anchors having bi-spheric capture structures with the multi-modal collection of receiver sub-assemblies as an advanced modular spinal fixation system for securing elongate rods to patient bone in spinal surgery. As described below, the individual bone anchor assemblies, systems, and/or methods of the present disclosure for this representative type of bi-spherical universal shank head can provide several significant advantages and benefits over other pivotal and/or non-pivotal bone anchors and spinal fixation systems known in the art due to, in one aspect, the degree of versatility and adaptability provided by the shank head universality (i.e. all of the shank heads having a common bi-spherical geometry that is connectable with each type of receiver sub-assembly that has its own predetermined combination degrees of freedom and operational functionalities) that is incorporated into the disclosed modular spinal fixation system. The recited advantages are not meant to be limiting in any way, however, as one skilled in the art will appreciate that other advantages and benefits may also be realized upon practicing the present disclosure.

Furthermore, those skilled in the relevant art will recognize that changes can be made to the disclosed embodiments for shank head universality, beyond those described, while still obtaining the beneficial results. It will also be understood and appreciated that some of the advantages and benefits of the described embodiment for the invention can be obtained by selecting some of the features (e.g. the structures or components) of the disclosed receiver sub-assemblies without utilizing other features, and that features from one sub-assembly embodiment may be interchanged or combined with features from other sub-assemblies in any appropriate combination. For example, any individual feature or collective features of method embodiments may be applied to apparatus, product or system embodiments, and vice versa. Likewise, structural elements or functional features from one embodiment may also be combined with or replaced by structural elements or functional features from one or more additional embodiments in any suitable manner. Those who work in the art will therefore recognize that many modifications and adaptations to the representative embodiments described herein are possible and may even be desirable in certain circumstances, and are to be considered part of the present disclosure. Thus, it will be appreciated that the present disclosure is provided as an illustration of the principles for the representative modular spinal fixation system incorporating the bi-spherical universal shank head that are shown and discussed therein, since the scope of each invention disclosed herein is to be defined by their respective claims.

As shown in FIG. 1, the present disclosure generally relates to a modular spinal fixation system 10 and associated methods for performing spinal fixation surgeries with the use of bone anchor assemblies having bone anchors (a.k.a. bone attachment structures such as screws, hooks, shanks, and other known anchor components) attached to longitudinal connecting members (such as rods, cords, connectors, and other known longitudinal connecting members) with bi-spherical universal shank heads 60 that can be bottom loaded into receiver sub-assemblies (i.e. housings or heads), and wherein the receiver sub-assemblies 22, 28, 32, 42 and at least some of their associated internal components can pivot and/or rotate axially in different selected directions relative to their bone anchors. More specifically, receiver sub-assemblies that are configured to provide the bone anchors with different modes of movement or degrees of freedom, such as multiplanar pivotal movement, monoplanar pivotal movement, and monoaxial movement (non-pivotal but axial rotatable), together with a variety of operational functionalities such as pre-lock friction fit with tool deployment of the pressure insert, pre-lock friction fit without tool deployment, provisional independent locking, open top receivers, closed top receivers, and the like, can be pre-assembled with their internal components into receiver sub-assemblies 22, 28, 32, 42 that are configured to be snapped onto or otherwise connected to the bi-spheric shank head 60 or upper end capture structure, of one or more shanks or bone anchors 50 (which may or may not be cannulated). This allows for the bone anchors to be affixed to the bony anatomy either before or after being connected with their respective pivoting or non-pivoting receiver sub-assemblies. For instance, in some cases it may be desirable to implant or attach the shanks or bone anchors into or on the spine of the patient independent of their larger and somewhat bulky receiver sub-assemblies, and decide later on in the surgical procedure where each of the multiplanar receiver sub-assemblies 22, 28, monoplanar receiver sub-assemblies 32, or monoaxial receiver sub-assemblies 42 should be placed and utilized on the implanted spinal construct. This type of multi-modal modular capability can be advantageous for both midline and pedicle screw placement trajectories into the vertebral bodies and to provide for enhanced procedural solutions in certain cases, including robotic assisted surgeries.

The spinal fixation system 10 shown in FIG. 1 is directed toward eliminating or at least improving upon shortcomings of the prior art through the introduction of a bone anchor, such as the shank 50 shown in FIG. 1(a), having an upper end capture structure comprising a bi-spherical "universal" shank head, or bi-spheric shank head 60, with both modularity and bone debris clearance capabilities (and that is inherently free of flat side surfaces). In particular, the bi-spheric shank head 60 of the present disclosure is configured to be cleared of bone debris and soft tissue simultaneous with the process or motion of being "snapped" into, or otherwise connected, and captured by either a multiplanar pivotal and independently axially rotatable receiver sub-assembly 22, 28, a monoplanar pivotal and independently axially rotatable receiver sub-assembly 32, an independently axially rotatable but non-pivotal receiver sub-assembly 42, or any other type of receiver sub-assembly having an alternative mode of movement. In one aspect, each type of receiver sub-assembly can further include an automatic or self-engaging pre-lock friction fit feature that can be established while avoiding the use of insert tool deployment or additional tooling, such as the tooling needed for alignment when connecting shank heads with flat side surfaces to a uniplanar or monoplanar receiver sub-assembly.

Figure 65:
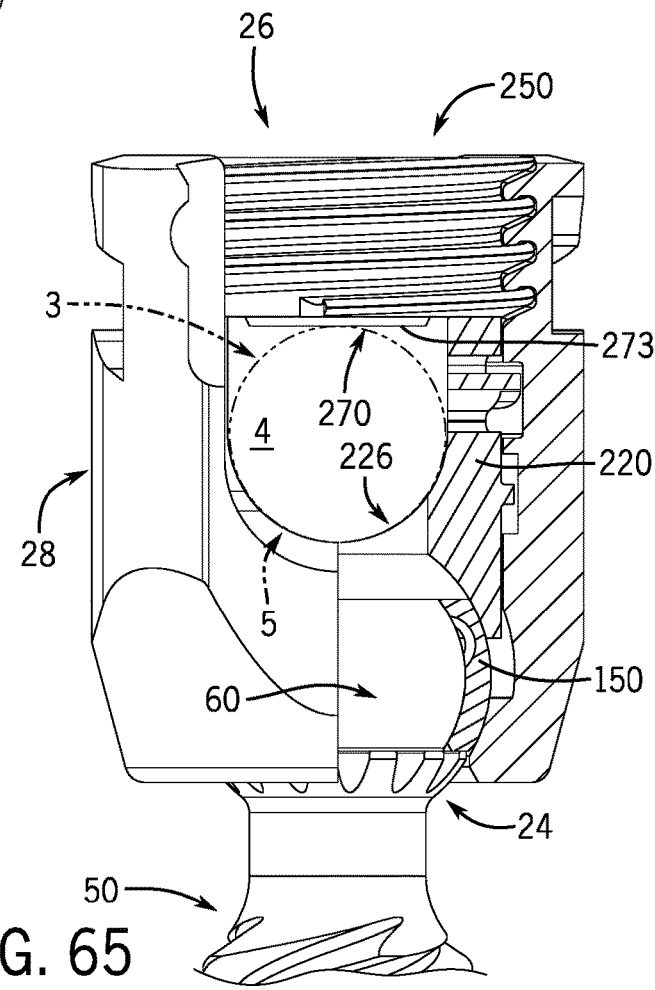
FIG. 65 is a partially cut-away front view of the multiplanar IL bone anchor assembly fully assembled with the elongate rod and with the center screw of the two-piece closure further engaging the upper surface of the elongate rod in the fully locked and secured configuration.

With continued reference to FIGS. 1(b) and 1(c), the representative embodiments of the multiplanar pivotal and axially rotatable receiver sub-assemblies 22, 28 with bone debris clearance can be combined with a bone screw 50 having the bi-spheric shank head 60 to form a multiplanar bone anchor assemblies 20, 26 further described in reference to FIGS. 5-65. The multiplanar bone anchor assemblies 20, 26 can include components having features or aspects configured to provide for continuous pivotal motion of the bone anchor relative 50 to the receiver sub-assembly 22, 28 around a 360-degree range, and also to provide for independent pre-lock frictional axial rotation relative to a longitudinal axis of the bone anchor around a 360-degree range, and is hereinafter interchangeably referred to as a polyaxial, multi-axial, or 'multiplanar' bone anchor assembly.

Similarly, the representative embodiment of the monoplanar pivotal and independently axially rotatable receiver sub-assembly 32 shown in FIG. 1(d) can be combined with a bone screw 50 having the bi-spheric shank head 60 to form a monoplanar bone anchor assembly 30 further described in reference to FIGS. 66-94. The monoplanar pivotal bone anchor assembly 30 can include alternative components having features or aspects configured to limit the pivotal motion of the bone anchor relative to the receiver sub-assembly 32 (or vice versa) to a single plane (i.e. sagittal, medial-lateral) while still providing for independent pre-lock frictional axial rotation around a 360-degree range, and is hereinafter interchangeably referred to as a uni-planar or 'monoplanar' bone anchor assembly 30. As shown in the drawings, the bi-spheric shank head 60 can be included into this monoplanar functionality without the use of parallel flat or planar side surfaces formed into the outer surfaces of the bi-spheric shank head.

Likewise, the representative embodiment of the non-pivotal but axially rotatable receiver sub-assembly 42 shown in FIG. 1(e) can be combined with the same bi-spheric shank head 60, or upper end capture portion geometry, to form a monoaxial bone anchor assembly 40 further described in reference to FIGS. 95-122. The monoaxial bone anchor assembly 40 can also include alternative components having features or aspects configured to prevent or inhibit pivotal motion of the bone anchor 50 relative to the receiver sub-assembly 42 (or vice versa) with some possible limited toggle, while still providing for independent pre-lock frictional axial rotation around a 360-degree range, and is hereinafter interchangeably referred to as a non-pivotal, fixed, or 'monoaxial' bone anchor assembly 40. Again, as shown in the drawings, the bi-spheric shank head 60 can be included into this non-pivotal monoaxial functionality without the use of parallel flat or planar side surfaces formed into the outer surfaces of the bi-spheric shank head.

Thus, regardless of the type, degree or amount of pivotal motion, the three major modes of movement or modality embodiments of the bone anchor assembly 20, 26, 30, 40 are together configured to provide the multi-modal modular spinal fixation system 10 wherein the bone anchor 50 can axially rotate around its longitudinal or spin axis relative to the receiver sub-assembly 22, 28, 32, 42 (or vice versa) at least prior to locking the bone anchor assembly 20, 28, 30, 40 with the closure in the final locked position and with at least some degree of a pre-lock friction fit. It will be appreciated that this feature can allow for the rotatable implantation, or screwing in, of only the anchor portion 84 of a pre-assembled bone anchor assembly 20, 26, 30, 40 to a desired depth in the bone of a patient without rotation of its respective receiver sub-assembly 22, 28, 32, 42, thereby allowing the receiver sub-assembly to be secured by separate tooling, or maintained in a desired alignment, throughout the rotatable implantation of the bone anchor. This feature can also allow for the height of the receiver sub-assembly 22, 28, 32, 42 above the bone, or the length of the anchor portion 84 of the bone anchor 50 that is implanted in the bone, to be more precisely controlled and independently adjusted, and wherein more aggressive thread forms having larger pitches for faster insertions with fewer rotations can also be utilized, especially with robot assisted surgeries. In addition, the geometry of the upper end capture portion 60 of the screw 50 can further provide for a very strong and secure connection with a driving tool for navigated manual or robotic assisted screw insertions, or even direct robotic screw insertions.

Bi-Spheric Universal Bone Anchor

Referring now in more detail to the drawing figures, specifically FIGS. 1(a) and 2-4, the bone anchor 50 of the spinal fixation system 10 (including but not limited to the shank shown in the drawings) includes the bi-spheric shank head or capture structure 60 at an upper or proximal end 51, and a body 80 extending distally from the bi-spheric shank head 60 with an attachment or anchor portion 84 at a distal end 99 configured for fixation to the bone of a patient. The body of the shank 80 can be integral with the bi-spheric shank head 60 and can include a neck portion or neck 82 that extends between the bi-spheric shank head 60 and the anchor portion 84. In one aspect the neck 82 can have a cross-sectional diameter that is less than both the diameter(s) of the bi-spheric shank head 60 and the cross-sectional diameter of the anchor portion 84 immediately below the neck 82, and can be configured to pivot against an inner edge of the lower opening of the receiver of a bone anchor assembly 22, 28, 32, 42 so as to provide an increased angle of articulation between the receiver and the bone anchor 50.

The bi-spheric shank head 60 at the upper end of the shank 50 generally comprises an upper partial spherical portion 64 defining an upper spherical surface 66 that extends above and below a hemisphere plane 64 of the bi-spheric shank head 60, and a lower partial spherical portion 74 defining a lower spherical surface 76 that begins at a lower offset plane 73 that is spaced below the hemisphere plane 65 to extend downward and merge with the neck 82 of the shank body 80. A lower upward-facing shelf or annular ledge 70 extends between the upper inner partial spherical portion 64 and the lower partial spherical portion 74, and can be considered the portion of the lower partial spherical portion 74 that extends radially outward beyond the upper spherical surface 66. As shown in the drawings, in one aspect the annular lower ledge 70 can define an upward-facing planar ledge surface 72 that extends perpendicular to the longitudinal axis 51 of the shank along the lower offset plane 73 between the upper and lower partial spherical portions. It is foreseen, nevertheless, that the lower ledge may not extend along the lower offset plane and may instead intersect the lower offset plane and the upper edge of the lower partial spherical portion at an acute angle, thereby defining a generally upward-facing ledge surface that is frusto-conical rather than planar, whether extending upwardly and outwardly, or downwardly and outwardly, from the upper partial spherical portion 64 to the lower partial spherical portion 74.

It is further foreseen that the generally upward-facing shelf surface 72 can provide an abutment face for the lower end of a driving tool, with the shelf surface being advantageously located well above the neck 82 of the shank body 80 so as to provide a shortened engagement profile for the driving tool that can reduce or substantially eliminate interferences between the driving tool and the bone of the patient.

Also shown in the drawings, the upper partial spherical portion 64 and upper spherical surface 66 have a minor diameter 67 that is less than the major diameter 77 defined by the lower partial spherical portion 74 and lower spherical surface 76. In one aspect the two outer spherical surfaces can be concentric, having their centers located together at the intersection between the hemisphere plane 65 and the longitudinal axis 51 of the shank. However, it is foreseen that the lower spherical surface 76 can have a center on the longitudinal axis that is offset above or below the hemisphere plane 65 defined by the upper spherical surface 66.

Also shown in the drawings, the lower spherical surface 76 may not be a continuous surface, with the lower partial spherical portion 74 optionally including a plurality of open, vertically aligned flutes 78 arranged circumferentially around the bi-spheric shank head 60 and extending downwardly through and below the lower ledge 70. As described in more detail below, the flutes 78 can serve as passages and/or storage pockets for bone debris and soft tissue being pushed off the upper spherical surface 66 of the bi-spheric shank head 60 by the cap retainer during assembly of the bone anchor 50 with a receiver sub-assembly. In one aspect the lower spherical surface 76 may also be considered a discontinuous lower spherical surface due to the interruptions to the spherical surface created by the flutes 78 formed into the structure of the annular lower ledge 70 and the lower partial spherical portion 74.

Figure 2:
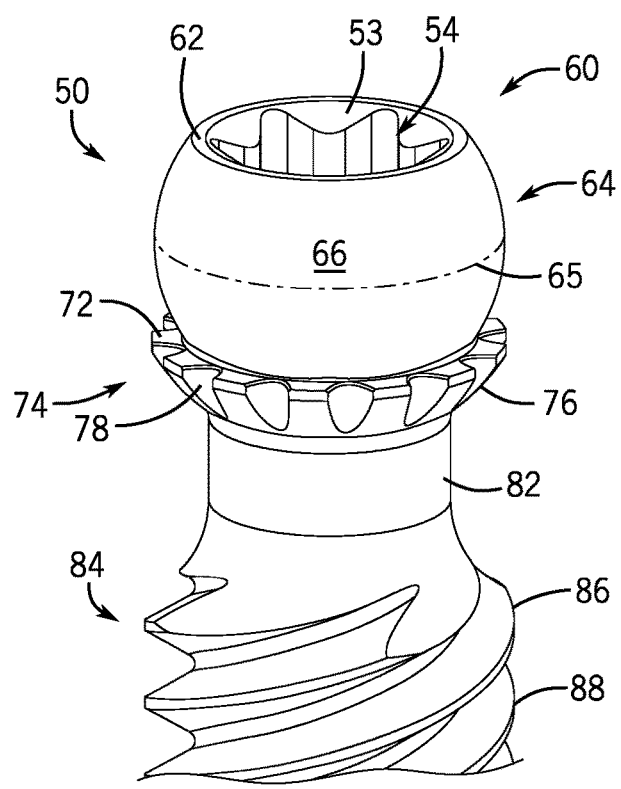
FIG. 2 is a perspective view of the bi-spheric shank head or capture portion of the universal bone anchor of FIG. 1.
Figure 3:
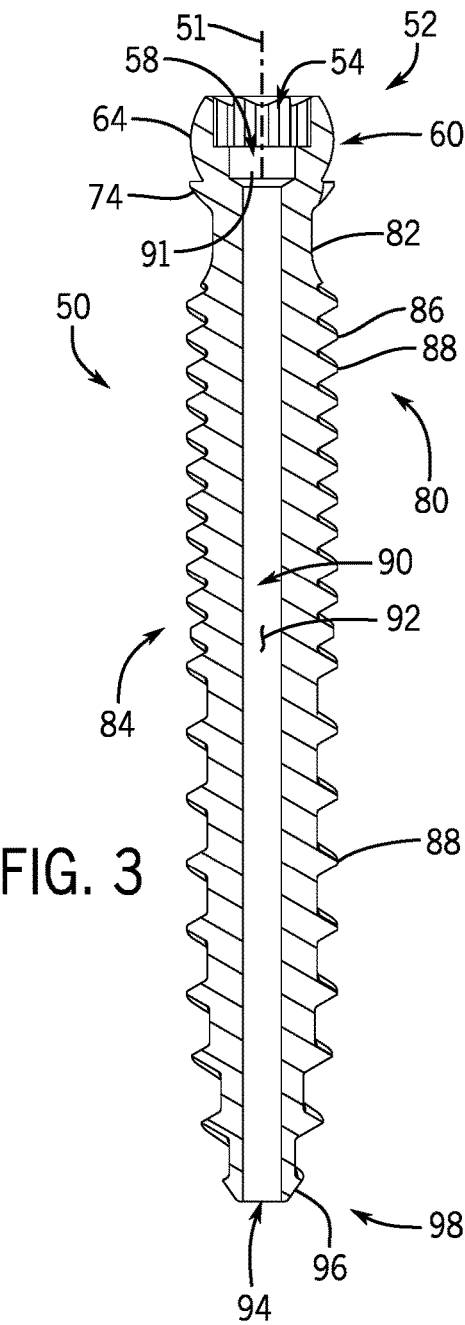
FIG. 3 is a cross-sectional side view of the universal bone anchor of FIG. 1.
Figure 4:
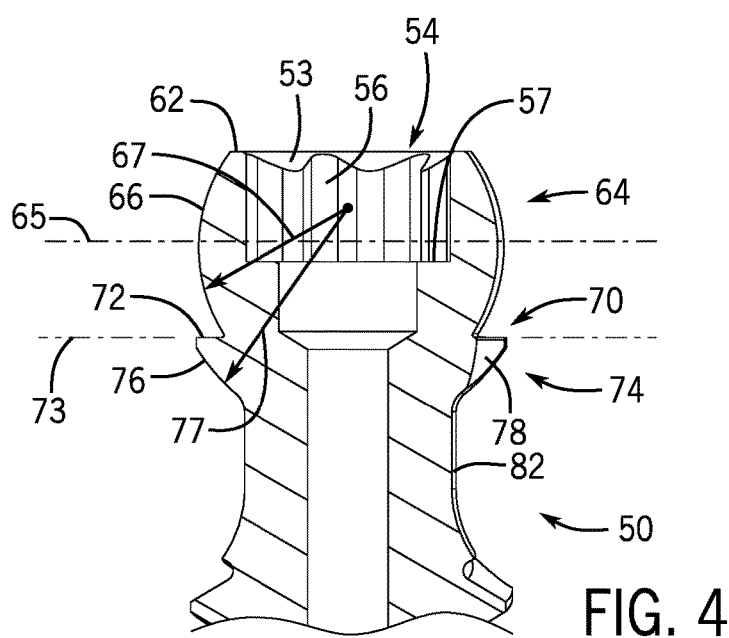
FIG. 4 is a cross-sectional side view of the bi-spheric shank head or capture portion of the universal bone anchor of FIG. 1.
Figure 7:
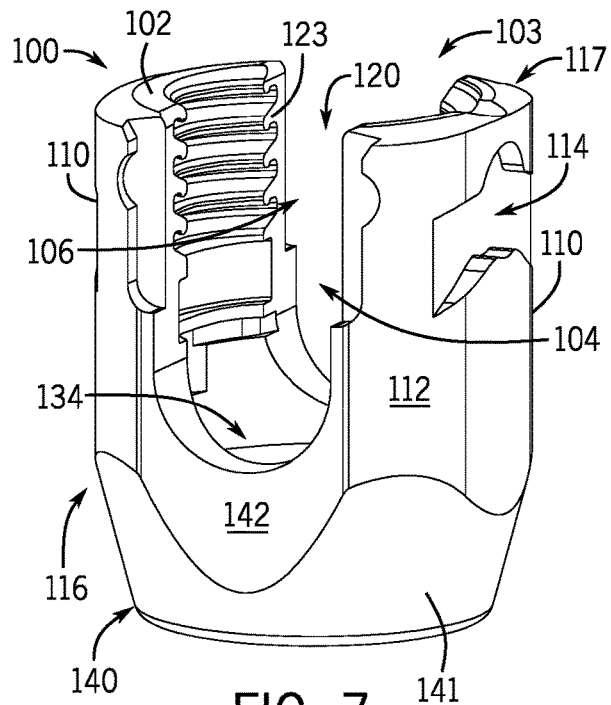
FIG. 7 is a perspective view of the receiver of the multiplanar bone anchor assembly of FIGS. 5-6.
Figure 8:
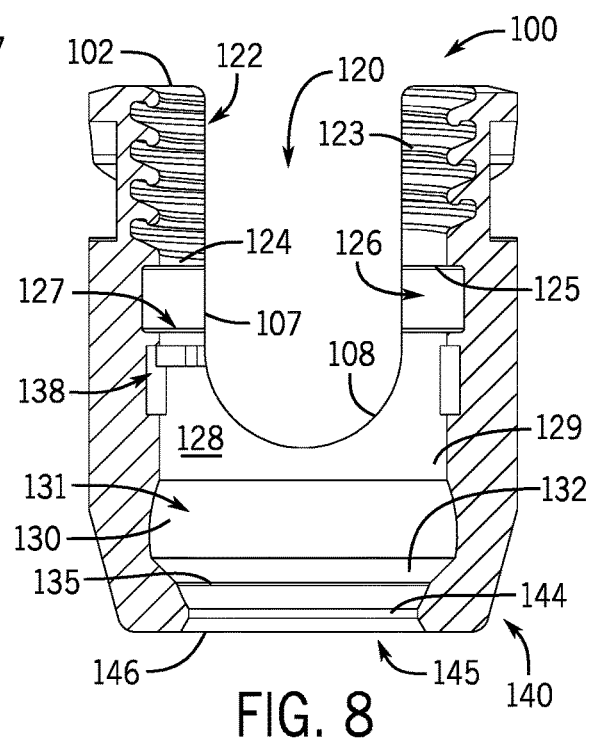
FIG. 8 is a cross-sectional side view of the receiver of FIG. 7.

With continued reference to FIGS. 2-4, the bi-spheric shank head can have an annular planar top surface 62 that surrounds an internal drive feature or drive socket 54. For example, the internal drive feature 54 of the bone anchor 50 illustrated in the figures is an aperture formed in an inwardly-tapered upper surface 55 that is surrounded by the annular planar top surface 62. In one aspect the internal drive feature 54 may be a multi-lobular or star-shaped aperture, such as those sold under the trademark TORX, or the like, having vertically-aligned sidewalls or internal faces 56 designed to receive a multi-lobular or star-shaped tool for rotating and driving the shank body 80 into the vertebra. It is foreseen that such an internal drive feature 54 may take a variety of tool-engaging forms and may include one or more apertures of various shapes, such as a pair of spaced apart apertures or a hex shape designed to receive a hex tool (not shown) of an Allen wrench type. A seat or base surface 57 of the internal drive feature 54 can be disposed perpendicular to the shank longitudinal axis 51, with the internal drive feature 54 otherwise being coaxial with the shank longitudinal axis. In operation, a driving tool is received in the internal drive feature 54, being seated at the base surface 55 and engaging the internal faces 56 of the internal drive feature 54 for both driving and rotating the anchor portion 84 of the shank body 80 into the vertebra, either before or after the shank 50 is attached or coupled to a multiplanar receiver sub-assembly. If attached, the threaded anchor portion 84 of the shank body 80 can be driven into the vertebra with the driving tool extending into and through the receiver.

Also shown in the drawings, in some embodiments the shank 50 can be cannulated with an axial bore 90 extending through the entire length thereof and centered about the longitudinal axis 51 of the shank 50. The axial bore 90 can be defined by an inner cylindrical wall 92 of the shank having a circular opening 94 at the distal tip 96 and an upper opening 58 communicating, in one aspect, with the internal aperture of the drive socket 54 at the base surface 57 (FIGS. 3-4). The axial bore 90 is generally coaxial with the shank body 80 and the bi-spheric shank head 60, and can provide a passage through the shank interior for a length of wire (not shown) to provide a guide for insertion of the shank body 80 into the vertebra. The axial bore 90 of the cannulated shank can also provide for a pin to extend therethrough and beyond the shank tip, the pin being associated with a tool to facilitate insertion of the anchor portion 84 of the shank body 80 into the vertebra.

Multiplanar Bone Anchor Assembly

FIG. 5 is partially-sectioned perspective view of one representative embodiment of the multiplanar bone anchor assembly 20 illustrated in FIG. 1(b), with the multiplanar receiver sub-assembly 22 and an elongate rod 4 being connected to the bi-spheric shank head 60 of the bone anchor 50 described above, and with the bone anchor 50 being pivoted and locked at an angle with respect to the receiver of the receiver sub-assembly 22. FIG. 6 is an exploded perspective view of the same multiplanar bone anchor assembly 20 and rod 4. As described above, the bone anchor 50 or shank of the multiplanar bone anchor assembly 20 includes the bi-spheric shank head or capture structure 60 at an upper or proximal end of the shank, and an anchor portion 84 opposite the bi-spheric shank head that is configured for securement within or attachment to the bone of a patient (not shown). The multiplanar receiver sub-assembly 22 generally includes a multiplanar receiver 100 or housing having a base portion 140 defining an internal cavity 134 or lower portion of a central bore, and a pair of upright arms 100 extending upwardly from the base portion 140 to define a rod channel 106 that is configured to receive the elongate rod 4. As discussed in more detail below, the central bore communicates with a bottom surface of the base of the receiver through a bottom opening, and extends upwards through the channel 106 to the top of the receiver (or tops of the upright of the arms 110 when the channel 106 is an open channel, as shown in the drawings).

The receiver 100 can be initially pivotably secured to the bi-spheric shank head 60 with a number of separate internal components that have been pre-assembled into the central bore and the rod channel to form the multiplanar receiver sub-assembly 22. These internal components can include, but are not limited to, a pivoting or articulating multiplanar cap retainer 150 that can be positioned in the internal cavity 134 or lower portion of the central bore, and which attaches to the bi-spheric shank head 60 to pivotably couple the shank 50 to the receiver sub-assembly 22. The receiver sub-assembly 22 further includes a multiplanar pressure insert 170, also known as a saddle, crown, cap, bushing, spacer or compression element, which can be positioned above the cap retainer 150 in a middle portion of the central bore where the central bore intersects with the channel 106. The pressure insert 170 is operable to engage with the cap retainer 150 below and to be engaged by the elongate rod 4 from above when the rod is positioned in the channel 106, and in one aspect can be an axially biasing insert, as described in more detail below. After the elongate rod 4 has been positioned within a lower portion of the rod channel 106 and into engagement with the pressure insert 170, a closure 190 can be threadably or otherwise secured into an upper portion of the central bore or rod channel to apply pressure to an upper surface of the rod 4, such as by direct contact, thereby locking both the elongate rod 4 and the multiplanar bone anchor assembly 20 into a final locked configuration or position, such as that shown in FIG. 5.

Illustrated in FIGS. 7-10 is the multiplanar receiver 100 having a generally U-shaped appearance with a partially discontinuous substantially cylindrical inner profile and a partially cylindrical and partially faceted outer profile, although other profiles are contemplated. For example, it is foreseen that this type of receiver can also be configured with planar lateral side surfaces. The receiver 100 generally comprises the base portion 140 defining the internal cavity 134 or lower portion of a generally cylindrical central bore 120 that is centered around the receiver's vertical centerline axis 101, and the pair of upright arms 110 extending upwardly from the base 140 to form the upper portion of the receiver and to define the upwardly-open channel 106 that is configured for receiving the elongate rod. Each of the upright arms 110 has an interior face 104 that includes a discontinuous upper portion of the central bore 120, which may be bounded on either side by opposed vertically-aligned planar end surfaces 107 that curve downwardly into U-shaped lower saddle surfaces 108. In one aspect the opposed planar end surfaces 107 and the curved saddle surfaces 108 can together define the front and back ends of the upwardly open channel 106 that also opens laterally onto a front face 116 and a back face 117 of the receiver 100, respectively. From top surfaces 102 of the upright arms 110 at the proximal end 103 of the receiver, the central bore 120 can extend downwardly through both the open channel 106 and the internal cavity 134 to communicate with a bottom surface 148 of the receiver through a bottom opening 145 at the distal end 147 of the receiver.

The upper or channel portion of the central bore 120 further includes a discontinuous guide and advancement structure 122 formed into the interior faces 104 of the upright arms 110, which guide and advancement structure 122 is configured to engage with a complementary structure formed into the outer side surfaces of the closure 190 (see FIG. 6), as described more fully below. The guide and advancement structure 122 in the illustrated embodiment is a discontinuous helically wound interlocking flange form 123. It will be understood, however, that the guide and advancement structure 122 could alternatively comprise a square-shaped thread, a buttress thread, a modified buttress thread, a reverse angle thread, or other thread-like or non-thread-like closure mating structure for operably guiding the closure downward between the upright arms 110 under rotation until the closure directly engages and presses against the elongate rod positioned within the channel 106. Additionally, the various structures and surfaces forming a helically wound guide and advancement structure 122 can also be configured to resist, to inhibit, to limit, or to preferentially allow and control some limited amount of splay of the upright arms 110 of the receiver 100 while advancing the closure downward under rotation and when torquing the closure against the elongate rod to generate a downwardly-directed thrust that locks the completely assembled multiplanar bone anchor assembly into position (see FIG. 5).

Moving downward along the interior faces 104 of the upright arms 110, the portion of the central bore 120 located between the vertical end surfaces 107 that define the channel 106 can include a discontinuous inner recess 126 that is defined at an upper end by the downward-facing upper arcuate surface 125 of a discontinuous upper ledge structure 124 located immediately below the guide and advancement structure 122, and at a lower end by an upward-facing lower arcuate surface 127 that also delineates the upper limit of a partially discontinuous cylindrical surface 128. In one aspect the discontinuous inner recess 126 can further comprise a runout groove for the guide and advancement structure 122. As can be seen in the drawings, the discontinuous portion of the cylindrical surface 128 can extend downwardly from the inner recess 126 to below and around the lower saddle surfaces 108 to form the continuous portion of the cylindrical surface 128 that defines the upper end of the internal cavity 134.

The discontinuous portion of the cylindrical surface 128 can further include opposed vertically-elongate side pockets 138 located below the discontinuous inner recess 126 formed into the interior faces 104 of the upright arms 110, with each side pocket 138 being defined by a vertically-aligned, inwardly-facing sidewall surface that can be bounded above and below by upper and lower planar surfaces, respectively. The sidewall surface can be sized and shaped to generally match the profile of indexing structures or nubs protruding from the side surfaces of the pressure insert, as described in more detail below. As disclosed in the present embodiment of the multiplanar receiver sub-assembly 22 illustrated in the drawing figures, for example, both the indexing nubs and the side pockets can have an arc-shaped profile.

Each side pocket 138 can also include one or more horizontal access recesses 139 extending from an upper portion of the side pocket 138 to an opposed vertical planar end surface 107 of the upright arm 110, so as to provide access to the side pockets 138 for the indexing nubs. In one aspect the depth of the horizontal access recesses 139 relative to the interior faces of the uprights arms can vary, and in particular can become slightly reduced or shallower, ramped, or increasingly-inwardly-sloped as moving from the opposed vertical planar end surfaces 107 toward the side pockets 138. This slight reduction in depth can create a resistance to the movement of the indexing nubs through the access recesses, and correspondingly a resistance to the rotation of the pressure insert 170 about the centerline axis 101 of the receiver, and which resistance can be released as soon as the indexing nubs pass completely through the horizontal access recesses 139 and into the vertical side pockets 138. It will be appreciated that the reduced depth of the horizontal access recess 139 as it merges with the side pocket 138 can also serve to inhibit the indexing nubs from accidentally or unintentionally re-entering the horizontal access recesses 139 from within the side pocket after the pressure insert 170 has been rotated into its aligned position with the channel 106 of the receiver 100.

With continued reference to FIGS. 7-10, the internal cavity 134 of the base portion 140 of the receiver 100 generally includes an upper expansion chamber portion 131 and a lower seating surface portion 136 located proximate the bottom opening 145. The expansion chamber 131 is generally defined by circular edge 129 demarking the bottom of the continuous portion of the partially discontinuous cylindrical surface 128, a curvate surface 130 extending outwardly and downwardly toward an angled or tapered lower transition surface 132 that, in turn, extends downwardly and inwardly to the upper circumferential edge of the seating surface 135. As shown in the figures, in one aspect the expansion chamber 131 can have a round or circular shape as viewed from above, although other shapes are also contemplated, such as oblong, squared with rounded corners, and the like, and are considered to fall within the scope of the present disclosure.

The lower portion off the internal cavity 134 includes the spherical seating surface 136 that is slidably mateable with the spherically-shaped discontinuous outer surface of the cap retainer and, at high angles of articulation of the bone anchor with respect to the receiver, with the lower spherical surface of the bi-spheric shank head. As shown in the drawings, the spherical seating surface 136 can be a partially spherically-shaped seating surface that extends downwardly below the upper circumferential edge 135 to a lower circumferential edge 137 with a lowermost cylindrical surface 144 that can define the bottom opening 145 of the receiver 100. A lowermost tapered surface 146 of the central bore 120 can extend downwardly and outward from the lowermost cylindrical surface 144 to the bottom surface 148 of the receiver to provide a tapered approach to the bottom opening 145. It is foreseen that the other shapes or structures for the seating surface of the central bore, which are also slidably mateable with the multiplanar cap retainer that is configured to capture and hold the bi-spheric shank head or capture portion 60 of the bone anchor, are also possible, including but not limited to a non-spherical surface, a conical or tapered surface, a chamfered surface, a sharp edged or stepped lower structure, a cylindrical surface, and the like, and are considered to fall within the scope of the present disclosure. It is further foreseen that the seating surface could also be in a separate lower portion or part of the receiver that is subsequently attached to an upper part of the receiver.

The multiplanar receiver 100 can have a partially cylindrical and partially faceted outer profile. In the illustrated embodiment, for example, the partially cylindrical portions can include curvate side outer surfaces 112 of the upright arms 110 opposite the interior faces 104 that extend downward from the top surfaces 102 of the upright arms toward a lower outer tapered surface 141 of the base 140 that angles inwardly to the bottom surface 148 of the receiver 100. The receiver 100 can further include upper curvate-extending instrument engaging grooves 114 below the top surfaces 102 of the upright arms 110 that extend horizontally across the curvate side outer surfaces 112, and in one aspect (not shown) can extend to the front face 116 and the back face 117 of the receiver 100.

Likewise shown in the drawings, the faceted or planar portions of the receiver 100 may comprise front and back outer planar faces 142 on the receiver base 140 below the open channel 106, and which can extend upwardly as narrow flats or tool engagement features on the front and back faces 116, 117 of the upright arms. The faceted or planar portions of the multiplanar receiver 100 can further include side outer planar faces (not shown) and/or tool receiving and engaging recesses (also not shown) formed into the curvate side outer surfaces 112 below the upper instrument engaging grooves 114, and which can be parallel with each other and oriented perpendicular to the front and back outer planar faces 142. In one aspect the upper instrument engaging grooves 114, the front and back outer planar faces 142, the narrow flats or tool engagement features, and any other planar tool-engagement surface or recess can serve together as outer tool engagement surfaces that allow for tooling to more securely engage and hold the receiver 100 during an initial pre-assembly with the internal components to form the multiplanar receiver sub-assembly 22, during coupling of the receiver sub-assembly to the bone anchor 50, either after or before the implantation of the anchor portion 84 of the bone anchor into a vertebra, and also during further assembly of the multiplanar receiver sub-assembly 20 with the elongate rod and the closure so as to aid in torquing and counter-torquing to lock the assembly.

Furthermore, it will be appreciated that the receiver 100 can also include additional features and aspects not shown in the drawings, including but not limited to inwardly-threaded breakoff extensions extending upwardly from the tops of the upright arms for interfacing with tooling and for guiding the elongate rod and the outwardly-threaded closure into the receiver channel. It is also foreseen that other shapes and configurations for the interior and exterior surfaces of the receiver 100, different from those shown in the drawings while providing for similar interaction and functionality of the various components of the pivotal bone anchor assembly, are also possible and considered to fall within the scope of the present disclosure, including but not limited to receivers having bottom openings with cut-out sections or slanted bottom surfaces that form oblique or expanded bottom openings, and the like, that provide for increased pivotal motion for the shank in at least one direction.

It is also foreseen that in alternative embodiments of the present disclosure the receiver can be configured with a closed rod-receiving channel, in which case the top surfaces and upper portions of the upright arms can be connected together to form a solid ring surrounding the central bore, and in which case one or more of the internal components of the sub-assembly can be uploaded into the central bore of the receiver through its bottom opening. In one such a bottom-loaded embodiment, for instance, it will be appreciated that the seating surface of the internal cavity can be replaced with an internal recess located adjacent the bottom opening that is configured to receive a separate open retaining ring having a slit or slot to provide for the contraction and expansion thereof, with the open retainer ring having an upper inner edge or partially spherical inner surface that is configured, in turn, to engage and support the lower spherical surface of the bi-spheric shank head and the cap retainer coupled to the bi-spheric shank head. Other configurations for the closed-top receiver sub-assembly and/or for the bottom-loaded components are also possible and considered to fall within the scope of the present disclosure.

Illustrated in FIGS. 11-14 is the multiplanar embodiment of the cap retainer 150 having the form of a hollow, partial spherical shell with a solid or continuous upper ring portion 154 having an annular planar upper surface 152 with a continuous circular inner edge 151 that defines a central upper opening 155. As can be seen in the drawings, a discontinuous outer spherical surface 156 extends downward from the continuous circular outer edge 153 of the upper surface 152 toward a discontinuous annular bottom surface 160, and a discontinuous inner spherical surface 158 extends downward from the circular inner edge 151 of the upper surface 152 toward the discontinuous annular bottom surface 160. The distance between the discontinuous inner spherical surface 158 and the discontinuous outer spherical surface 156 can define the thickness of the partial spherical shell that forms the cap retainer. A plurality of slots 162 can be formed through the thickness of the cap retainer 150, from the discontinuous inner spherical surface 158 to the discontinuous outer spherical surface 156 and extending upward from the discontinuous annular bottom surface 160 toward the continuous circular upper flange portion. The slots 162 can be equally spaced around the circumference of the cap retainer 150 to form a plurality of flexible collet fingers 164 extending downward from the upper ring portion, and which collet fingers 164 can flex outwardly at their lower ends, so as to expand a central lower opening 165 of the cap retainer 150 to receive the bi-spheric shank head of the shank. It will be appreciated that the discontinuous outer spherical surface 156, the discontinuous inner spherical surface 158, and the discontinuous annular bottom surface 160 can be considered 'discontinuous' due to the interruptions in the surfaces created by plurality of slots extending upwardly through the lower edge and thickness of the lower portions of the shell forming the cap retainer 150, and that other terminology may also be applicable.

In addition, it is foreseen that alternative configurations, structures, or materials that provide the cap retainer with its expansion and contraction functionality are also possible and considered to fall within the scope of the present disclosure. For example, in one alternative embodiment the circular upper flange portion of the cap retainer may not be solid or continuous, and instead can include a through slot or gap extending from the discontinuous annular bottom surface or from one of the slots upwards through the upper flange portion to the annular planar upper surface 152, so as to make the cap retainer an open ring structure that is both compressible and expandable for uploading into the internal cavity receiver through the bottom opening.

As shown in the drawings, the cap retainer 150 can also include an inner beveled edge surfaces 159 between the discontinuous bottom annular surface 160 and the discontinuous inner spherical surface 158, which inner beveled edge surfaces 159 can define the expandable central lower opening 165 of the cap retainer. An outer beveled edge surface 161 can also be formed between the discontinuous bottom annular surface 160 and the discontinuous outer spherical surface 156. In addition, a rounded or curvate inner groove 166 can be formed into an upper portion of the discontinuous inner spherical surface 158 below the circular upper ring portion 154, which groove 166 can serve to reduce the thickness of cap retainer 150 near the roots of the downwardly-extending collet fingers 164 and thereby reduce stress in the material and facilitate the expansion of the collet fingers 164 during uploading of the bi-spheric shank head. In one aspect the upper ends of the slots 162 formed through the thickness of the cap retainer can also be formed as rounded apertures 163 or curved stress-relieving end passages.

Figure 9:
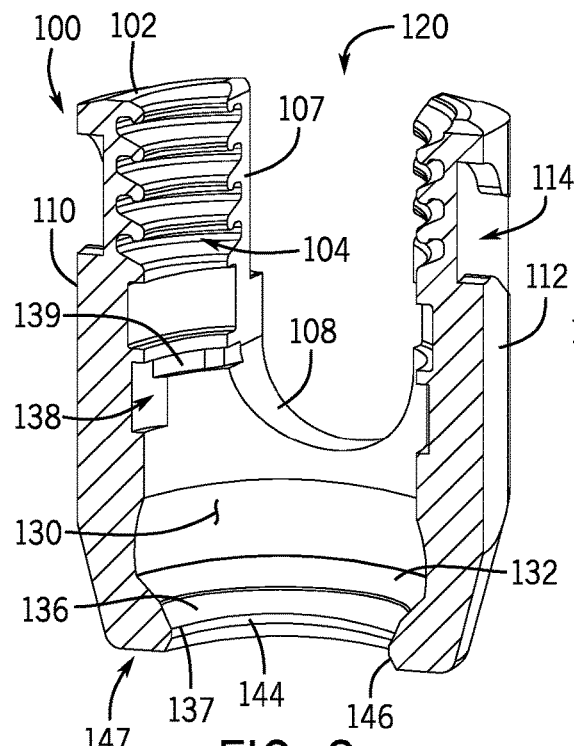
FIG. 9 is a cross-sectional perspective view of the receiver of FIG. 7.
Figure 10:
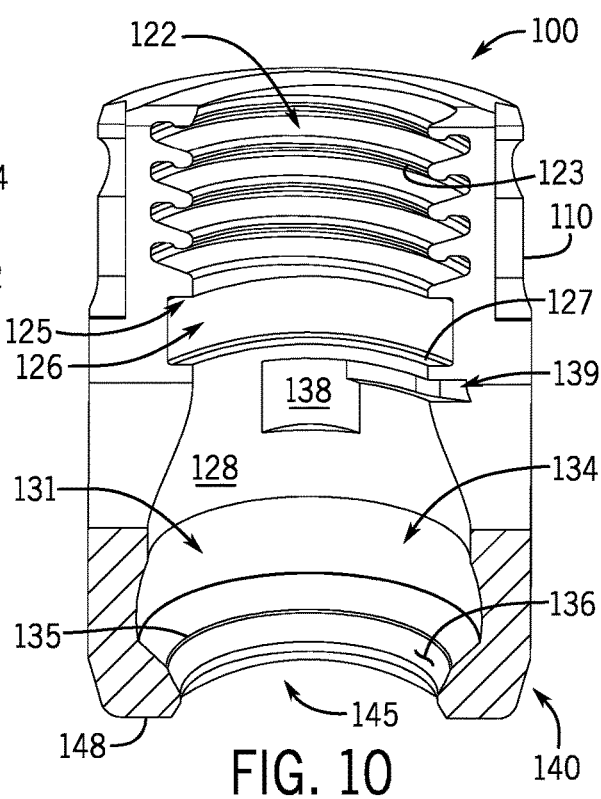
FIG. 10 is another cross-sectional perspective view of the receiver of FIG. 7.
Figure 11:
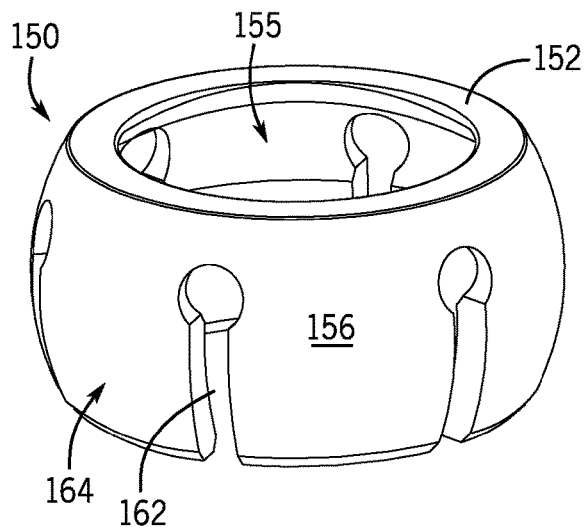
FIG. 11 is a perspective view of the cap retainer of the multiplanar bone anchor assembly of FIGS. 5-6.
Figure 12:
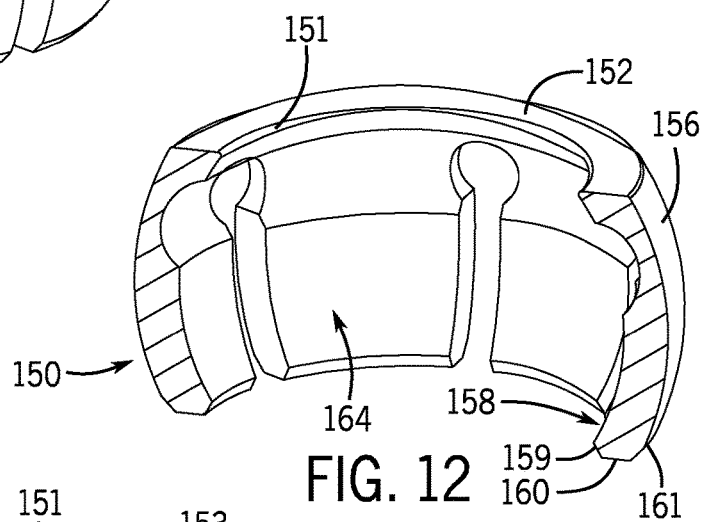
FIG. 12 is a cross-sectional perspective view of the cap retainer of FIG. 11.
Figure 13:
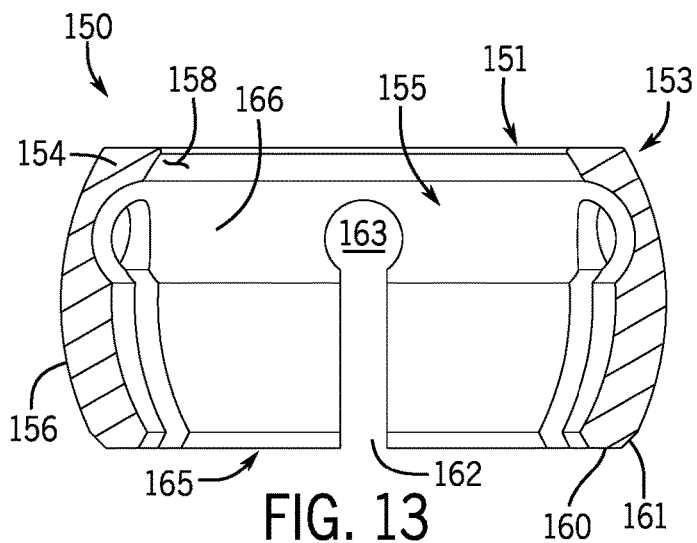
FIG. 13 is a cross-sectional side view of the cap retainer of FIG. 11.
Figure 14:
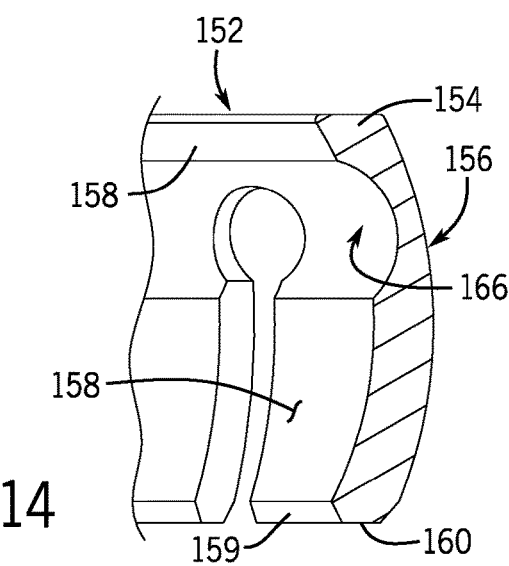
FIG. 14 is a close-up cross-sectional perspective view of a portion of the cap retainer of FIG. 11.
Figure 15:
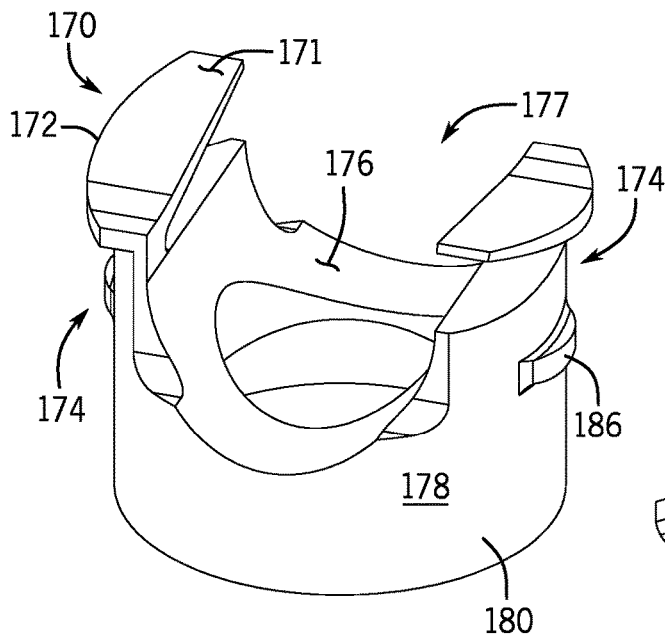
FIG. 15 is a top perspective view of the pressure insert of the multiplanar bone anchor assembly of FIGS. 5-6.
Figure 16:
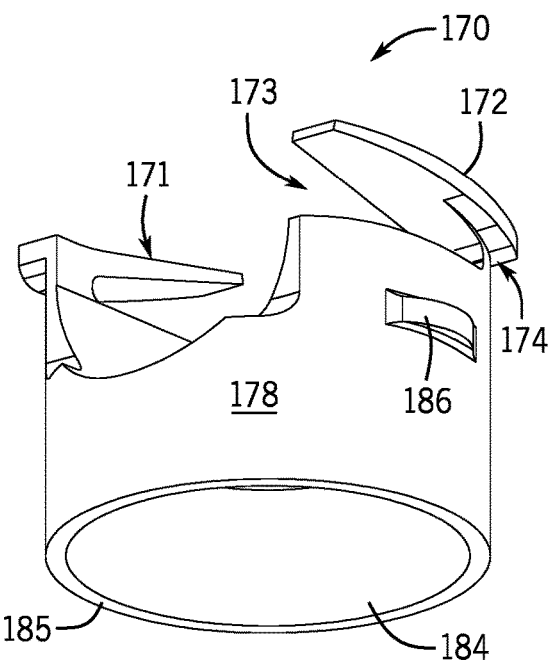
FIG. 16 is a bottom perspective view of the pressure insert of FIG. 15.
Figure 17:
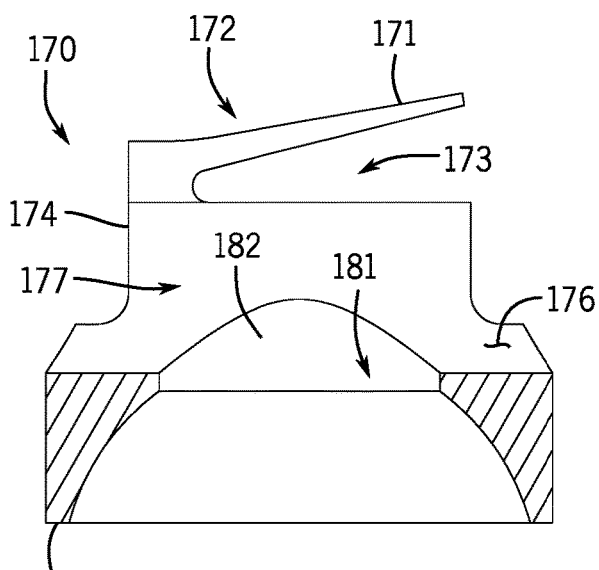
FIG. 17 is a cross-sectional side view of the pressure insert of FIG. 15.
Figure 18:
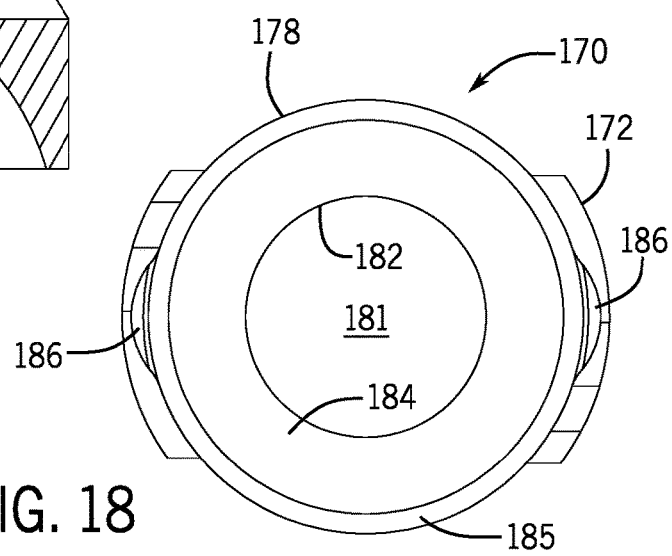
FIG. 18 is a bottom view of the pressure insert of FIG. 15.

The diameter of the discontinuous inner spherical surface 158 of the cap retainer 150 is substantially equal to the minor diameter 67 defined by the upper spherical surface 66 of the bi-spheric shank head 60 (see FIG. 4), while the diameter of the discontinuous outer spherical surface 156 is substantially equal to the major diameter 77 defined by both the lower spherical surface 76 of the bi-spheric shank head 60 and the spherical seating surface 136 of the receiver 100 (see FIGS. 9-10). As such, the cap retainer 150 can be sized and shaped so that once positioned on the bi-spheric shank head 60, as described in more detail below, the discontinuous inner spherical surface 158 can mate or engage with the upper spherical surface 66 while the discontinuous annular bottom surface 160 engages with the lower upward-facing shelf or ledge 72 of the bi-spheric shank head. In this coupled or captured configuration, in one aspect the annular planar upper surface 152 of the cap retainer 150 can be substantially flush or aligned with the annular planar top surface 62 of the bi-spheric shank head 60. It is nevertheless foreseen that in other embodiments the top surface of the bi-spheric shank head and/or the upper surface of the cap retainer may not be planar, and that the top surface of the bi-spheric shank head can also be proud or recessed relative to the upper surface of the cap retainer in the coupled or captured configuration.

Illustrated in FIGS. 15-18 is the multiplanar pressure insert 170 that generally includes a lower base portion 180 with a pair of insert arms 174 extending upward from the lower base portion 180, with the base portion 180 and the two insert arms 174 together defining a cylindrical outer surface that 178 is sized to be slidably received within the central bore of the multiplanar receiver. The insert arms 174 can form an insert channel 177 extending therebetween that is alignable with the channel of the receiver after the pressure insert has been positioned within the central bore, and which insert channel 177 can be further defined by an upward-facing rod seating surface 176 extending between the insert arms 174 that is engageable with the cylindrical elongate rod. The pressure insert can also include a spherical, downwardly-opening concave lower surface 184, extending upward and inward from an annular planar bottom edge surface 185, that is engageable with the discontinuous spherical outer surface of the cap retainer. The pressure insert 170 can further include a central tool-receiving aperture 181 defined by an inner cylindrical surface 182 that is configured to slidably receive a drive tool (not shown) that extends downwardly through the central bore of the multiplanar receiver to engage the internal drive socket formed into the top end of the bi-spheric shank head.

The insert arms 174 can include upper flanges 172 that project radially outward from the cylindrical outer surface that 178 so as to extend into the discontinuous recess 126 formed into the central bore 120 of the multiplanar receiver 100 (see FIGS. 8 and 10) when the pressure insert 170 is rotated about the vertical centerline axis of the receiver, with top surfaces 171 that are configured to rotate under the downward-facing upper arcuate surfaces 125. The pressure insert 170 can be an axially biasing pressure insert, in which the upper flanges 172 are formed as integral upwardly-angled resilient structures or spring tabs having top surfaces 171 configured to resiliently engage with the downward-facing upper arcuate surfaces 125 of the discontinuous recess 126 so as to provide a resilient downwardly-directed force that biases the pressure insert 170 against the discontinuous spherical outer surface of the cap retainer. In one aspect the integral spring tabs can be made by forming or machining slots 173 inward from the trailing edges of the insert upright arms 174 to define the flat flange structures, and then bending the trailing end of each flange structure upward to form the resilient upper flanges 172.

It is foreseen that other types of resilient upper flanges, including non-integral axially-biasing spring elements secured within complementary recesses formed into the upper ends of the upright insert arms, such as the variety of U-shaped axially-biasing clips disclosed in U.S. Patent Publication No. 2023/0225768 (for co-pending U.S. application Ser. No. 18/156,195), which is incorporated by reference in its entirety herein, are also possible and considered to fall within the scope of the present disclosure. It is further foreseen that additional features of the pressure inserts disclosed in U.S. patent Publication No. 2023/0225768, including but not limited to pressure inserts having a hybrid insert rod channel or upward-facing rod seating surface that is configured to receive elongate rods of differing size, as also considered to fall within the scope of the present disclosure.

The multiplanar pressure insert may additionally include an indexing structure configured to releasably engage with a complementary indexing structure formed into the central bore of the multiplanar receiver, upon rotation of the insert about the receiver vertical centerline axis, so as to inhibit further rotation of the insert out of its rotated position. For example, in one embodiment the indexing structure of the insert can comprise opposite outwardly-projecting indexing nubs 186 or protuberances located on the sides of the insert, under the resilient upper flanges 172, that can become positioned with the opposed vertical side pockets formed into the central bore of the multiplanar receiver upon rotation of the pressure insert 170 into its rotated position. It is foreseen that other structures can be used to hold the insert relative to the receiver, such as crimps, pegs, set screws or separate rings, to inhibit rotational movement and/or to control translational movement of the insert along the vertical axis of the receiver, and that the insert could be snapped in place, or otherwise positioned, within the receiver.

It is further foreseen that the multiplanar pressure insert may also be sized and shaped, or otherwise configured, for bottom loading into the internal cavity and central bore of the multiplanar receiver through the bottom opening, and then rotated into position or simply pressed into place. Such an alternative embodiment may also include changes to the multiplanar receiver and the multiplanar cap retainer and for the incorporation of one or more additional components, such as the separate open retaining ring described above. Moreover, it will also be appreciated that such changes are not limited to the multiplanar receiver sub-assembly, but can also be applied to the monoplanar and monoaxial receiver sub-assemblies described in more detail below.

Figure 19:
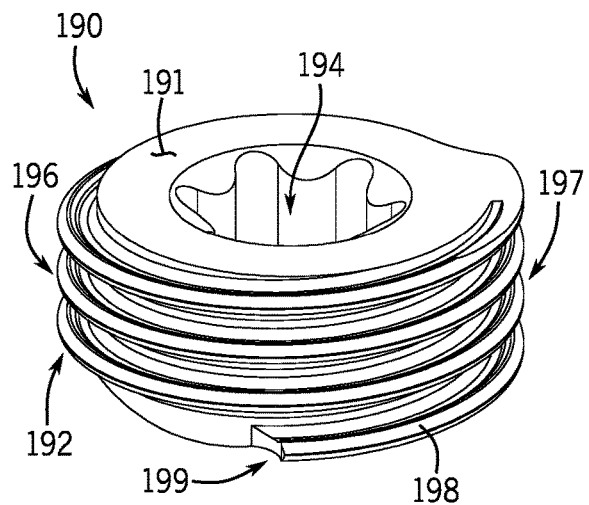
FIG. 19 is a top perspective view of the closure of the multiplanar bone anchor assembly of FIGS. 5-6.
Figure 20:
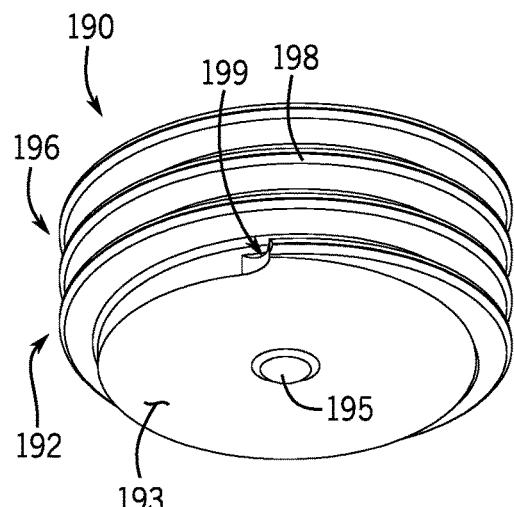
FIG. 20 is a bottom perspective view of the closure of FIG. 19.

With reference to FIGS. 19-20, in one embodiment the closure 190 can comprise a single-piece closure having a generally cylindrical closure body 192 with a top surface 191, a bottom surface 193, and an outer continuous guide and advancement structure 195 formed into the outer side surface 196 of the closure body 192 that operably joins with the discontinuous guide and advancement structure formed into the upright arms of the receiver. As illustrated, the outer continuous guide and advancement structure 196 can be a single flange/single lead-in guide and advancement structure having a single helically wound interlocking closure flange form 198 and a corresponding single start 199. In one aspect the closure flange form 198 can include a splay-resisting or splay-controlling flange profile for operably guiding under rotation and advancing the closure 190 downward between the upright arms and having such a nature so as to resist, inhibit, limit, or preferentially control the splaying of the upright arms when the closure is advanced into the rod channel. In other embodiments not shown, the outer continuous guide and advancement structure can be a dual flange/dual lead-in guide and advancement structure having first and second closure flange forms and corresponding first and second closure starts, or may have more than two closure flange forms and corresponding starts. In other aspects, the guide and advancement structure may take on a variety of alternative forms, including but not limited to single closure thread/single start, dual closure threads/dual starts, buttress threads, square threads, reverse angle threads, interlocking gripping or dovetail-like threads, or other thread-like or non-thread-like helically wound advancement structures.

As shown in the drawings, in one aspect the bottom surface 193 of the closure 190 can include a downwardly-projecting central point 195 for engaging and securing the elongate rod. In other embodiments the bottom surface can include an annular projection, a point ring (i.e. an annular ring surrounding a central point or projection), a downwardly-projecting stepped planar surface for controlling the closure torque to thrust ratio, a recessed surface surrounded by a low outer ridge, and the like. In yet other embodiments the bottom surface can be substantially planar across the extent thereof. In yet other embodiments the closure can have a through-and-through central opening.

The top surface 191 of the closure 190 can further include a driving tool engagement structure, such as a central internal drive socket 194, which extends downward or inward into the body of the closure. The internal drive socket 194 can be used for closure installation or removal. Similar to the internal drive feature formed into the shank head, the internal drive socket of the illustrated closure is an aperture formed in the top surface, and in one aspect can be a multi-lobular or star-shaped aperture, such as those sold under the trademark TORX, or the like, having internal faces designed to receive a multi-lobular or star-shaped tool for rotating and driving the closure. It is foreseen that such a driving tool engagement structure may take a variety of tool-engaging forms and may include one or more apertures of various shapes, such as a plurality of bores of different diameters, a pair of spaced apart apertures or a hex shape designed to receive a hex tool (not shown) of an Allen wrench type. In one aspect the seat or base surface of the internal drive socket can be disposed perpendicular to a closure axis, with the internal drive socket otherwise being coaxial with the axis. In yet other embodiments the internal drive socket can extend entirely through the closure.

In another aspect of the present disclosure, a break-off extension (not shown) can be attached the upper end or top surface of the closure, and extend upwardly away therefrom to provide an external tool engagement structure that can be used for rotatably advancing the closure downward between the upright arms of the receiver. In one aspect the break-off extension can be designed to allow the extension to break from the closure at a preselected torque, for example, 60 to 140 inch pounds. It is further foreseen that closures having other shapes, configurations, thread forms or non-threaded engagement alternatives, and the like, that are different from those shown in the drawings while providing for similar interaction and functionality of the various components of the bone anchor assembly, are also possible and considered to fall within the scope of the present disclosure. For example, the thread forms can have a thread depth, as measured from its root to its crest, which is equal to half or less than half of the thread pitch.

Figure 21:
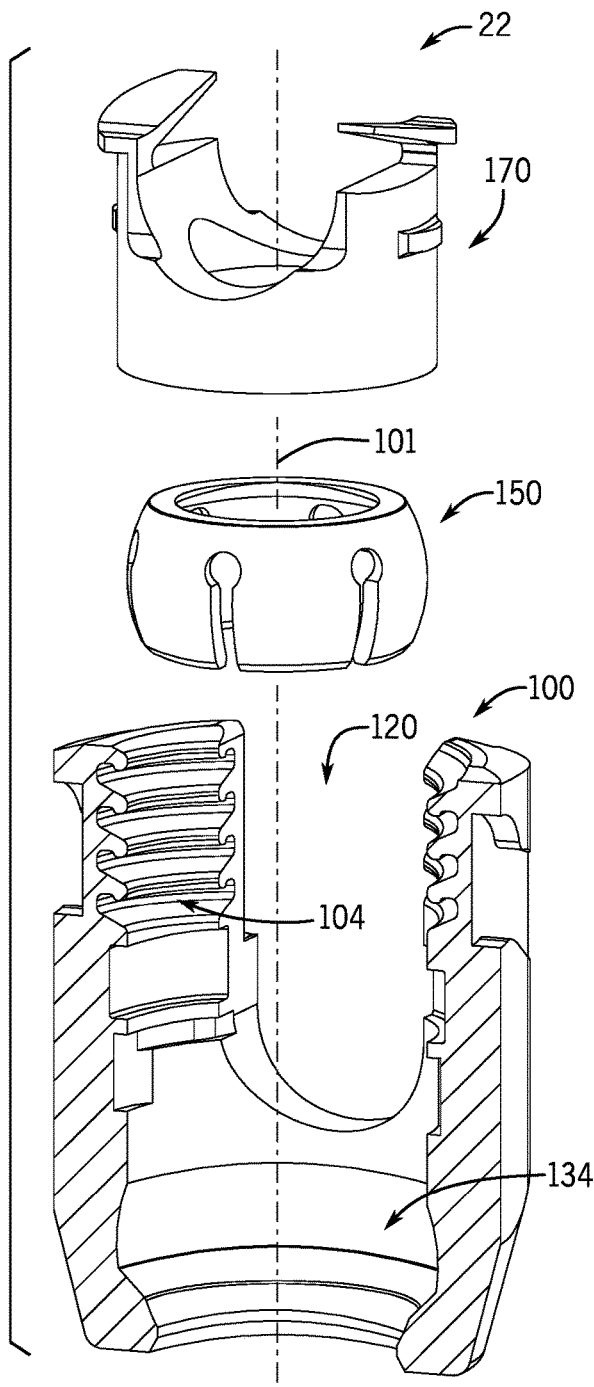
FIG. 21 is an exploded partially cut-away front perspective view of the components of the multiplanar receiver sub-assembly of FIG. 6 prior to their pre-assembly into a shipping configuration.

Illustrated in FIG. 21 are the individual components of the multiplanar bone anchor assembly 20 that, in many embodiments, can be pre-assembled together into a multiplanar receiver sub-assembly 22 at a factory or manufacturing facility, prior to shipping to a spine company or a hospital or surgery center and engagement with the bi-spheric shank head of the bone anchor in the surgical setting. As described above, these components generally include the multiplanar receiver 100, the multiplanar cap retainer 150, and the multiplanar pressure insert 170. In one aspect the multiplanar versions of the receiver 100, the cap retainer 150, and the pressure insert 170 being pre-assembled into a multiplanar receiver sub-assembly 22 can be further defined as the shipping state configuration for the 'modular' multiplanar bone anchor assembly 20, as described herein and commonly understood in the art. It will be appreciated, however, that in other embodiments the shipping state configuration can include the additional assembly of the multi-planar receiver sub-assembly together with the bone anchor or shank at the factory or manufacturing facility or the spine company. It will also be appreciated that in yet other embodiments the individual components described above can also be pre-assembled into the receiver sub-assembly at the hospital or surgery center prior to implantation in a patient.

Figure 22:
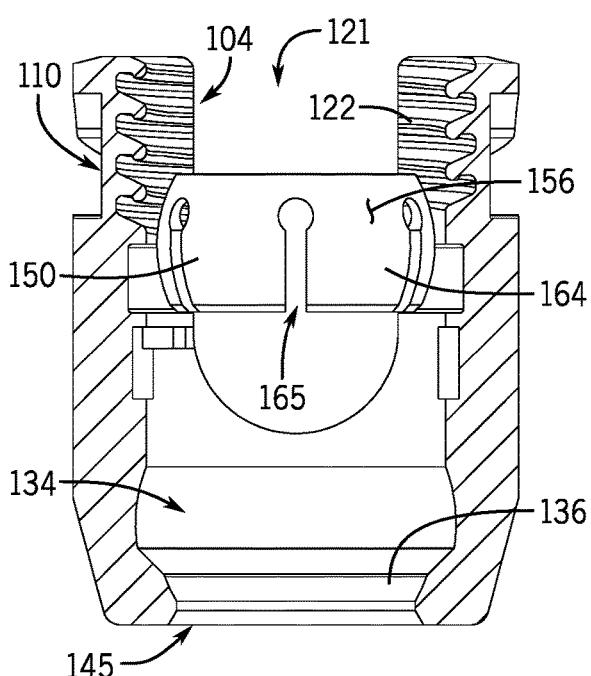
FIG. 22 is a partially cut-away front view of the receiver of FIG. 21 with the multiplanar cap retainer being downloaded through the open channel of the receiver.
Figure 23:
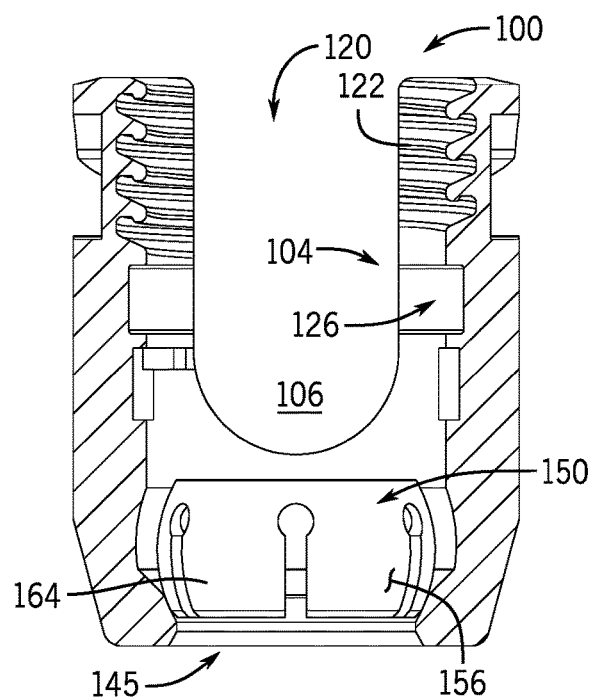
FIG. 23 is a partially cut-away front view of the receiver of FIG. 21 with the seated multiplanar cap retainer contacting the spherical seating surface of the receiver.

To begin the pre-assembly of the receiver sub-assembly, the cap retainer 150 can first be top-loaded into the receiver 100, as shown in FIGS. 22-23. With the cap retainer 150 having a major diameter that is less than the diameter of cylindrical outer surface of the insert and the upper portion of the central bore 120 of the receiver 100, and in particular less than the inner diameter of the guide and advancement structure 122 formed into the interior faces 104 of the upright arms 110 of the receiver 100, the cap retainer 150 can simply be downloaded through the central bore 120 in any orientation until the discontinuous outer spherical surface 156 engages with the spherical seating surface 136 at the lower end of the cavity 133 of the receiver 100. If needed, the cap retainer 150 can then be rotated to a horizontal position resting on the spherical seating surface 136, as shown in FIG. 23, with the central lower opening 165 defined by the inner beveled edge surfaces 159 of the collet fingers 164 being centered adjacent to and aligned with the bottom opening 145 of the receiver 100.

Figure 24:
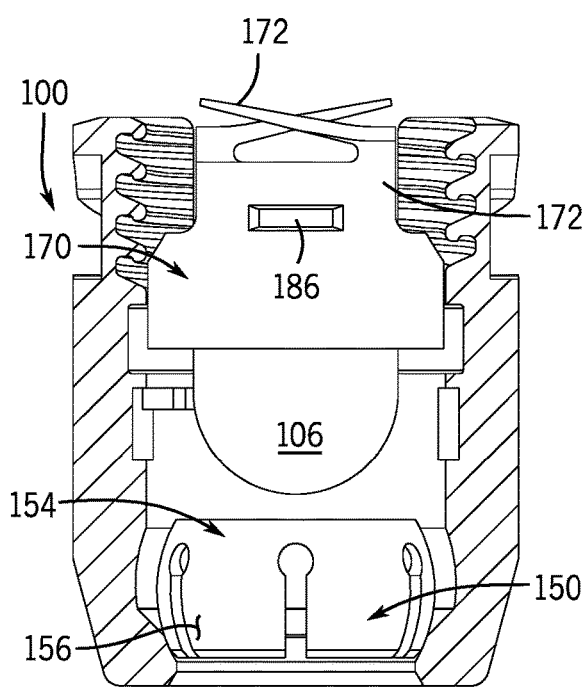
FIG. 24 is a partially cut-away front view of the receiver of FIG. 21, together with the seated multiplanar cap retainer and with the pressure insert being downloaded through the open channel of the receiver.
Figure 25:
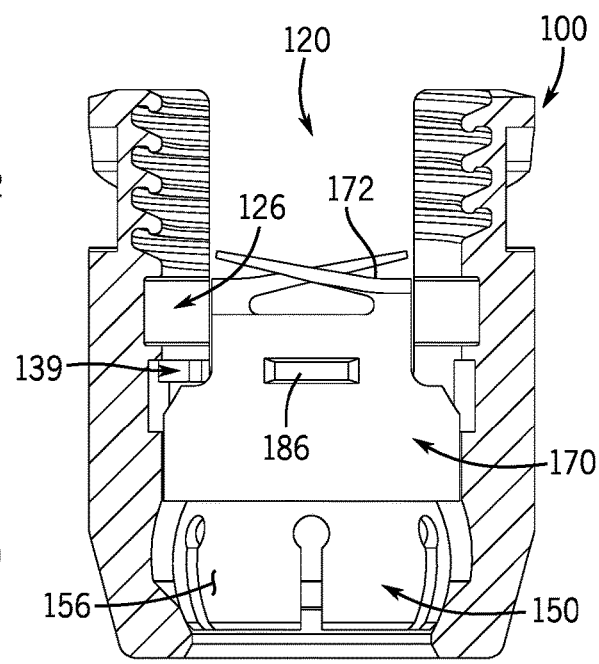
FIG. 25 is a partially cut-away front view of the receiver of FIG. 21, together with the seated multiplanar cap retainer and with the pressure insert being further downloaded into the internal cavity of the receiver.

After the cap retainer 150 is seated on the spherical seating surface 136 of the receiver 100, the pressure insert 170 may then be top-loaded or down-loaded into the central bore 120 and installed into its the shipping state position above the cap retainer 150. As shown in FIGS. 24-25, this can be achieved by positioning the pressure insert 170 above the central bore 120 with the insert arms 174 and upper flanges 172 being aligned with the open channel 106, and then downloading the pressure insert 170 through the channel 106 (FIG. 24) until the leading edges of the upper flanges 172 reach the level of the discontinuous inner recess 126 formed into the central bore 120 for this type of twist-in-place axially biasing pressure insert, and the outwardly-projecting indexing nubs 186 reach the level of the horizontal access recesses 139 (FIG. 25). In this initial pre-rotation position the concave lower surface 184 of the pressure insert 170 is still spaced above the upper ring portion 154 and discontinuous outer spherical surface 156 of the cap retainer 150.

Figure 26:
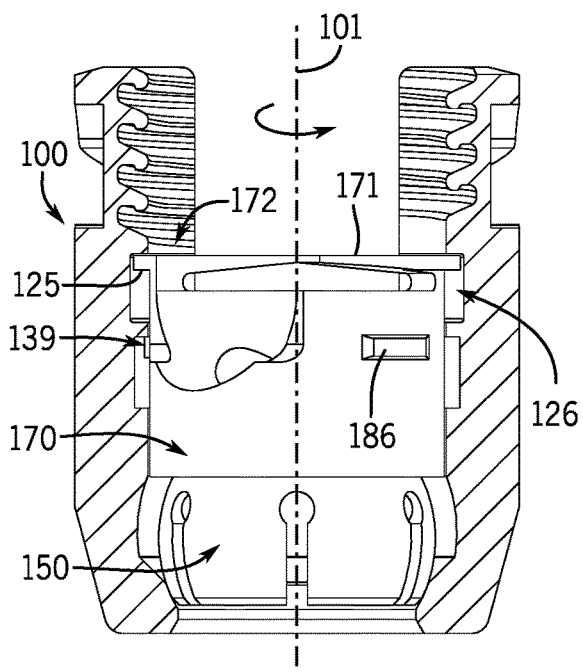
FIG. 26 is a partially cut-away front view of the receiver of FIG. 21, together with the seated multiplanar cap retainer and the downloaded and partially rotated pressure insert.
Figure 27:
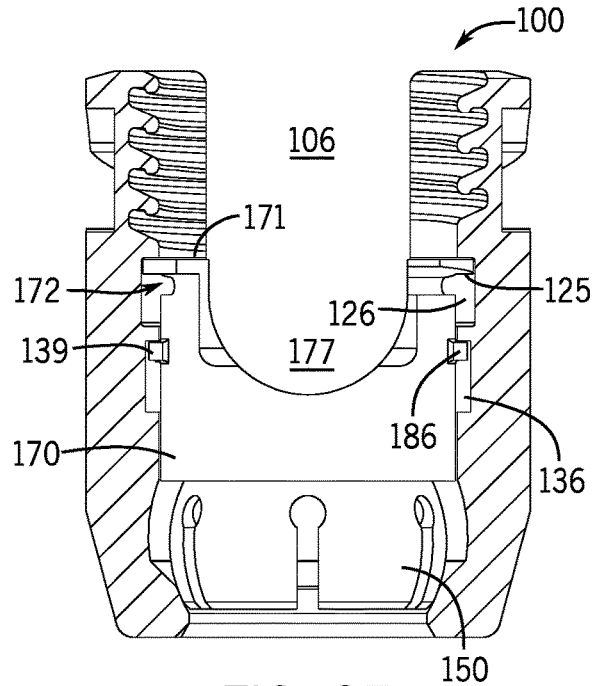
FIG. 27 is a partially cut-away front view of the receiver of FIG. 21, together with the seated multiplanar cap retainer and the downloaded and almost completely rotated pressure insert.

After reaching the initial downloaded position shown in FIG. 25, the pressure insert 170 may then be rotated around its longitudinal axis (which is co-axial with the vertical centerline axis 101 of the receiver 100) so that the leading edges of the radially or outwardly-projecting and upwardly-angled upper flanges 172 begin to enter into the discontinuous inner recess 126 of the upright arms 110 and the outwardly-projecting indexing nubs 186 enter the horizontal access recesses 139. Continued rotation of the pressure insert 170 can cause the top surfaces 171 of the upper flanges 172 to slidably resiliently engage with the downward-facing upper arcuate surfaces 125 of the discontinuous recess 126. Because the vertical location of the pressure insert 170 within the central bore 120 is temporarily fixed by the location of the indexing nubs 186 within the horizontal access recesses 139, this slidable engagement will cause the resilient upper flanges 172 to deflect downward under compression in order to enter the discontinuous recess 126, as shown in FIG. 26. The rotation of the pressure insert 170 can continue for a full 90 degrees or quarter turn, until the rod channel 176 of the insert 170 becomes aligned with the open channel 106 of the receiver 100, the compressed upper flanges 172 become fully positioned within the discontinuous inner recess 126 of the interior faces 104 of the upright arms the 104, and the indexing nubs 186 almost completely slide into the opposed vertical side pockets 138 of the central bore 120, as shown in FIG. 27.

Figure 28:
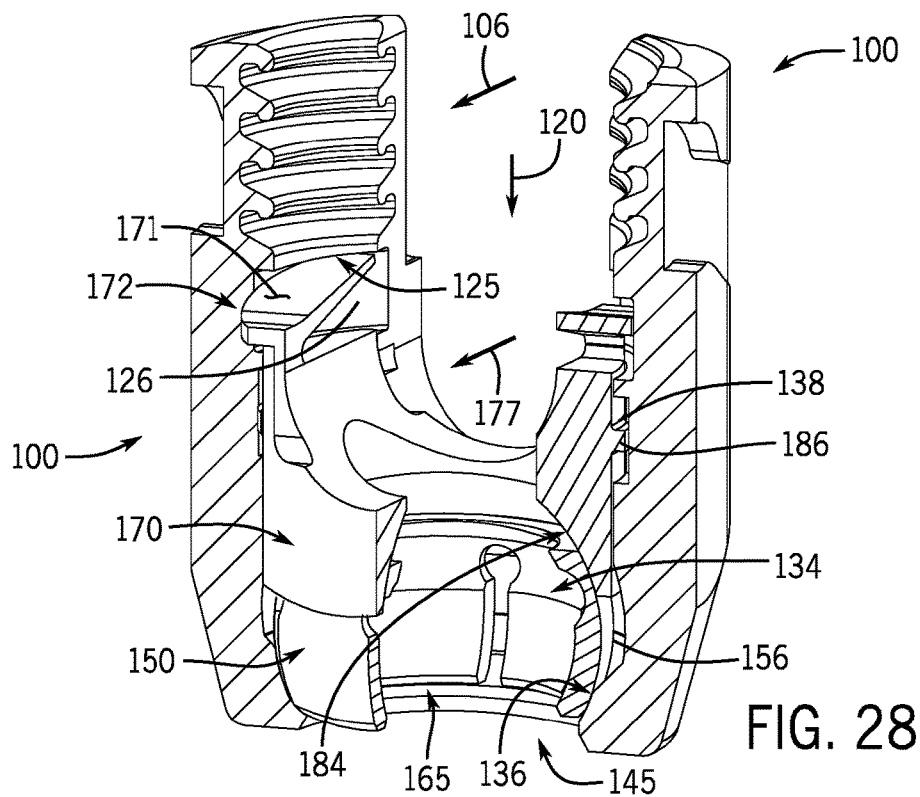
FIG. 28 is a partially cut-away front perspective view of the receiver of FIG. 21, together with the seated multiplanar cap retainer and the pressure insert being fully rotated therein and automatically deployed to form a pre-assembled multiplanar receiver sub-assembly in the shipping state configuration.
Figure 29:
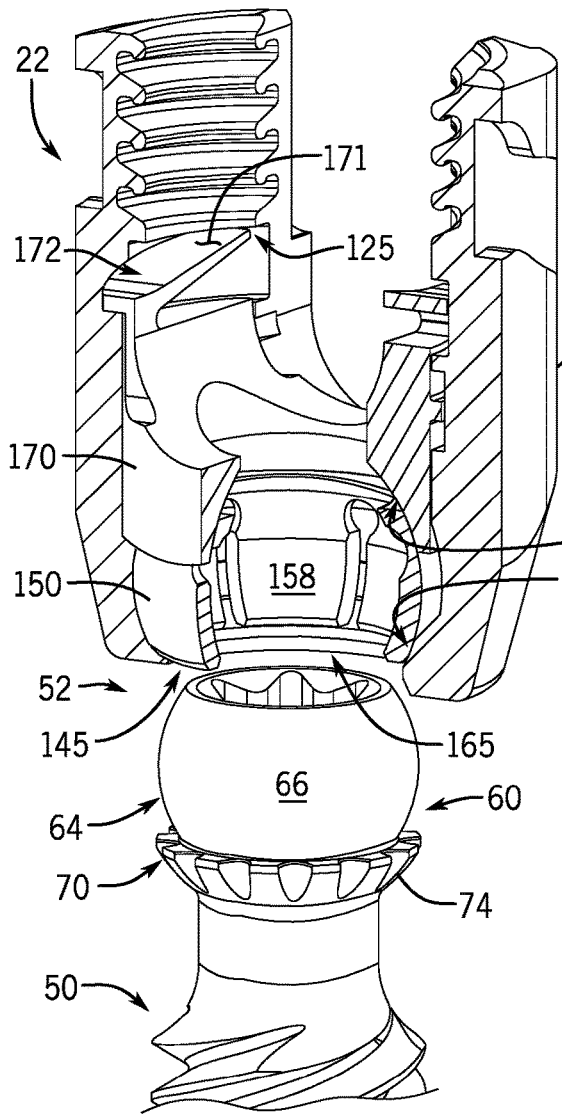
FIG. 29 is a partially cut-away front perspective view of the multiplanar receiver sub-assembly positioned above the bi-spheric shank head of the universal bone anchor.

As soon as the indexing nubs 186 exit the horizontal access recesses 139 and completely enter into the opposed vertical side pockets 138, the compressed upper flanges 172 can release to drive the pressure insert 170 downward until the concave lower surface 184 of the pressure insert engages an upper portion of the discontinuous outer spherical surface 156 of the cap retainer, as shown in FIG. 28. The downward movement of the pressure insert 170 also causes the indexing nubs 186 to move downward within the side pockets 138 and below the horizontal access recesses 139, so that further engagement between the indexing nubs 186 and the sides of the vertically-aligned side pockets 138 can inhibit rotation of the pressure insert 170, either clockwise or counter-clockwise, out of its rotated and aligned position in which the rod channel 176 of the insert 170 is aligned with the open channel 106 of the receiver 100. At same time, the continued compressive engagement between the upward-facing top surfaces 171 of the upper flanges 172 and the downward-facing upper arcuate surfaces 125 of the discontinuous inner recess 126 can allow for a limited amount of vertical travel, under load, while preventing the pressure insert 170 from moving back up to the upper end of the central bore or from exiting the receiver. The same compressive engagement between the upper flanges 172 and the downward-facing upper arcuate surfaces 125 can also bias the pressure insert 170 downwardly to engage and drive the cap retainer 150 downward against the spherical seating surface 136, so as to establish a frictional engagement between the upper portion of the discontinuous outer spherical surface 156 of the cap retainer 150 and the concave lower surface 184 of the pressure insert 170, and between the lower portion of the discontinuous outer spherical surface 156 and the spherical seating surface 136 of the internal cavity 136 of the receiver. This frictional engagement, or pre-lock friction fit, can stabilize and inhibit motion of the cap retainer 150 within the internal cavity 134 of the receiver 100 to prevent any subsequent rotation or misalignment of the cap retainer 150 relative to the bottom opening 145 that would impede the uploading of the bi-spheric shank head of the shank during assembly.

It is foreseen that other structures for holding the pressure insert 170 in alignment with the central bore 120 of the receiver 100 are also possible and considered to fall within the scope of the present disclosure, including but not limited to a reversal of the male/female relationship with an inwardly-protruding projection being formed on an inner surface of the central bore and a recess or notch being formed into the outer surface of the pressure insert. It is also foreseen that other structures or configurations for the axially biasing pressure insert, including but not limited to a multi-part pressure insert that replaces the integral flanges with separate, non-integral spring-like elements attached to upper end portions of the insert arms, are also possible and considered to fall within the scope of the present disclosure.

Thus, upon the resiliently axially-biased pressure insert 170 being rotated into its fully installed position within the receiver above the cap retainer 150, as shown in FIG. 28, the receiver sub-assembly 22 of the multiplanar bone anchor assembly 20 is now in its biased shipping state position or configuration that is configured to prevent both the pressure insert 170 and the cap retainer 150 from exiting the central bore 120 of the receiver 100 and/or from moving out of alignment. With the pre-assembly of the multiplanar receiver sub-assembly 22 now complete, moreover, the receiver sub-assembly 22 is ready for storage and/or shipping and handling, and for eventual attachment to the bi-spheric shank head of a bone anchor or shank either prior to or during spinal surgery.

One representative embodiment or method for assembling the multiplanar receiver sub-assembly 22 to the bi-spheric shank head 60 of the bone anchor 50 is illustrated in FIGS. 29-34. For instance, and with initial reference to FIG. 29, the receiver sub-assembly 22 can be first positioned above the proximal end 52 of the bone anchor 50 with the expandable central lower opening 165 of the cap retainer 150, which is centered within the bottom opening 145 of the receiver 100, being generally aligned with an upper portion of the upper partial spherical portion 64 of the bi-spheric shank head 60.

Figure 30:
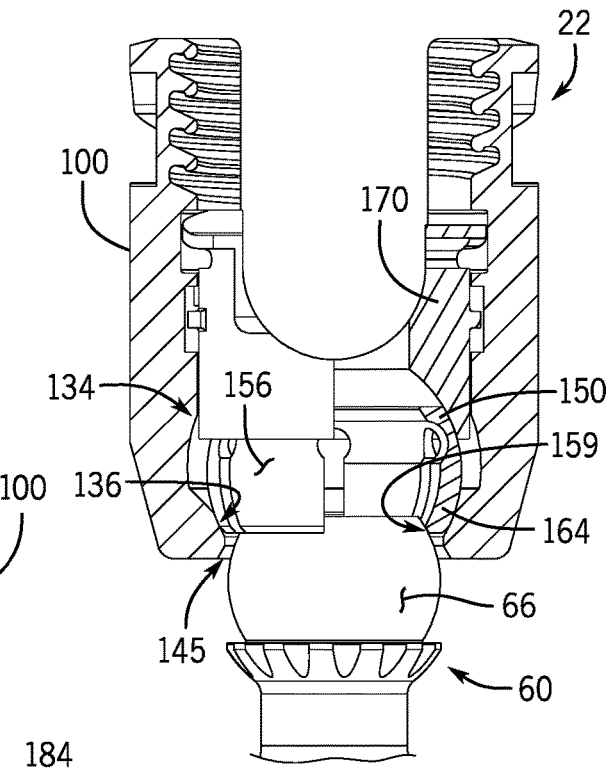
FIG. 30 is a partially cut-away front view of the multiplanar receiver sub-assembly moving downward until the bi-spheric shank head engages the cap retainer secured within the receiver by the pressure insert.

With reference to FIG. 30, the receiver sub-assembly 22 is then dropped downward (or the bone anchor is moved upward, depending on the frame of reference of the reader) until the upper spherical surface 66 of the bi-spheric shank head 60 passes upward through the bottom opening 145 of the receiver 100 to engage the inner beveled edge surfaces 159 of the collet fingers 164 that define the central lower opening 165. Because the lower portion of the discontinuous outer spherical surface 156 of the cap retainer 150 is received by and engaged with the spherical seating surface 136 of the internal cavity 134, the lower portion of the cap retainer 150 cannot expand or open upon the initial contact with the bi-spheric shank head 60, and the cap retainer 150 is only free to move upwards within the internal cavity 134.

As the receiver sub-assembly 22 continues to move downward (or the bone anchor moves upward), the bi-spheric shank head 60 begins to push both the cap retainer 150 and the pressure insert 170 upwards within the internal cavity 134 and the central bore 120 of the receiver 100, respectively, thereby compressing the radially-projecting and upwardly-angled upper flanges 172 of the pressure insert against the immovable upper arcuate surfaces 125 of the discontinuous recess 126. At the same time, the central lower opening 165 of the cap retainer 150 begins to expand as the cap retainer 150 enters the upper expansion portion 131 of the internal cavity 134, thereby allowing the inner beveled edge surfaces 159 of the collet fingers 164 that are adjacent to the discontinuous annular bottom surface 160 of the cap retainer 150 to spread apart as they scrape downwards across the upper spherical surface 66 of the bi-spheric shank head 60, pushing any bone debris and/or soft tissue located on the outer surface downwards before them.

Figure 31:
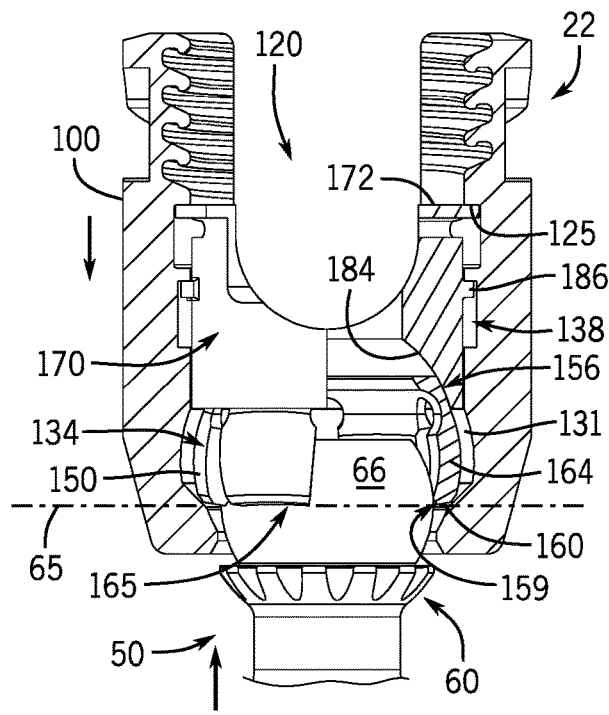
FIG. 31 is a partially cut-away front view of the multiplanar receiver sub-assembly continuing to move downward and the cap retainer and pressure insert being pushed upward to their uppermost positions, and the bi-spheric shank head continuing to drive upward as it expands the cap retainer within the internal cavity until reaching the maximum expansion of the cap retainer.

In one aspect the upwardly-directed axial force applied by the bone anchor 50 during the uploading of the bi-spheric shank head 60 may be only partially counter-balanced by the downwardly-directed resilient axial biasing provide by the resilient upper flanges 172 of the pressure insert, so that the pressure insert 170 quickly reaches its uppermost position within the central bore 120 defined by the upper surfaces of the indexing nubs 186 abutting against the downward-facing upper surfaces of the vertical side pockets 138. With the pressure insert 170 now being fixed relative to the receiver 100, and the upper portions of the cap retainer 150 being engaged against the concave lower surface 184 of the pressure insert 170, the collet fingers 164 of the cap retainer 150 continue to be expanded within the expansion portion 131 of the internal cavity 134 by the upward movement of the bi-spheric shank head 60 into the receiver 100. The expansion of the cap retainer 150 can continue, with the inner beveled edge surfaces 159 and/or the discontinuous annular bottom surface 160 pushing any bone debris and/or soft tissue located on the upper spherical surface 66 downwards before it, until the discontinuous annular bottom surface 160 reaches the level of the hemisphere plane 65 of the bi-spheric shank head 60 and the collet fingers 164 of the cap retainer 150 are at their point of maximum expansion, as shown in FIG. 31.

Figure 32:
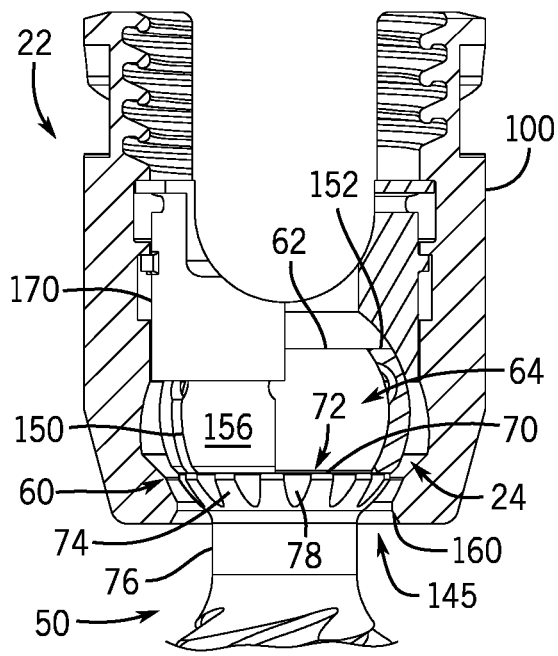
FIG. 32 is a partially cut-away front view of the multiplanar receiver sub-assembly continuing to move downward and the bi-spheric shank head continuing to drive upward until the bi-spheric shank head is completely captured by the cap retainer.

With reference to FIG. 32, the receiver sub-assembly 22 continues to move downward (or the bone anchor moves upward) as the upper partial spherical portion 64 of the bi-spheric shank head 60 becomes fully captured by the cap retainer 150 as it contracts to close around the upper spherical surface 66. During this motion, the discontinuous annular bottom surface 160 continues to push any bone debris and/or soft tissue downward toward the annular lower ledge 70 as the lower partial spherical portion 74 now moves upward into and through the bottom opening 145 of the receiver 100. Any bone debris and/or soft tissue that has been removed from the upper spherical surface 66 of the bi-spheric shank head 60 can pass through the plurality of open, vertically aligned flutes 78 that extend downwardly through and below the lower ledge 70 as the discontinuous annular bottom surface 160 engages the upward-facing planar surface 72 of the lower ledge 70.

The discontinuous inner spherical surface 158 of the cap retainer 150 is now secured around the upper partial spherical portion 64 of the bi-spheric shank head 60. Furthermore, with the simultaneous engagement of the discontinuous bottom annular surface 160 against the lower ledge 70 of the lower partial spherical portion 74, the cap retainer 150 is also now aligned on the bi-spheric shank head 60 so that the annular planar upper surface 152 of the cap retainer 150 can be aligned or flush with the annular top surface 62 of the bi-spheric shank head 60. In addition, the discontinuous outer spherical surface 156 of the cap retainer 150 can also be aligned with the lower spherical surface 76 of the lower partial spherical portion 74 so as to create a single diameter, articulating, multiplanar shank head sub-assembly 24 having the major diameter 77 that is greater than the diameter of the bottom opening 145 of the receiver 100, thereby preventing the bottom loaded shank 50 from exiting the receiver 100 back out through the same bottom opening 145 through which it was initially loaded. It will be appreciated that the cap retainer 150 can still remain a member of the receiver sub-assembly 22 even after its coupling to the bi-spheric shank head 60 to form the shank head sub-assembly 24, and as such may be considered the linking mechanism that connects the two sub-assemblies together.

Figure 33:
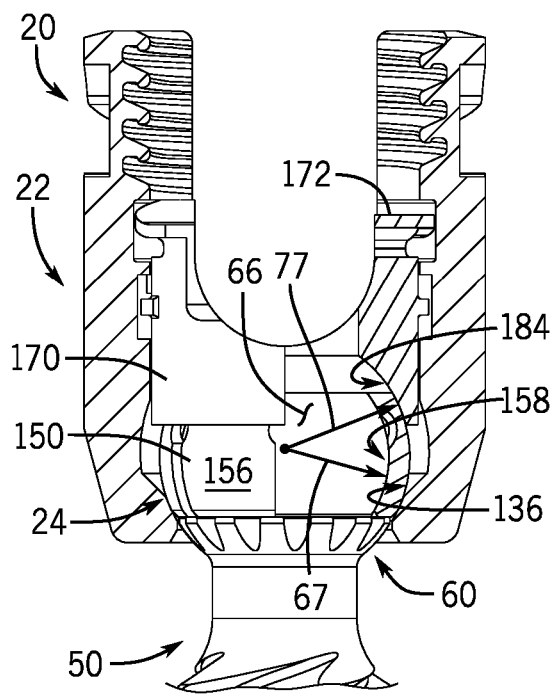
FIG. 33 is a partially cut-away front view of the multiplanar receiver sub-assembly with the uploading force being released and pressure insert being automatically downwardly deployed to push the multiplanar shank head sub-assembly back downward against the seating surface of the receiver to establish the initial configuration of the multiplanar bone anchor assembly in a pre-lock friction fit.
Figure 34:
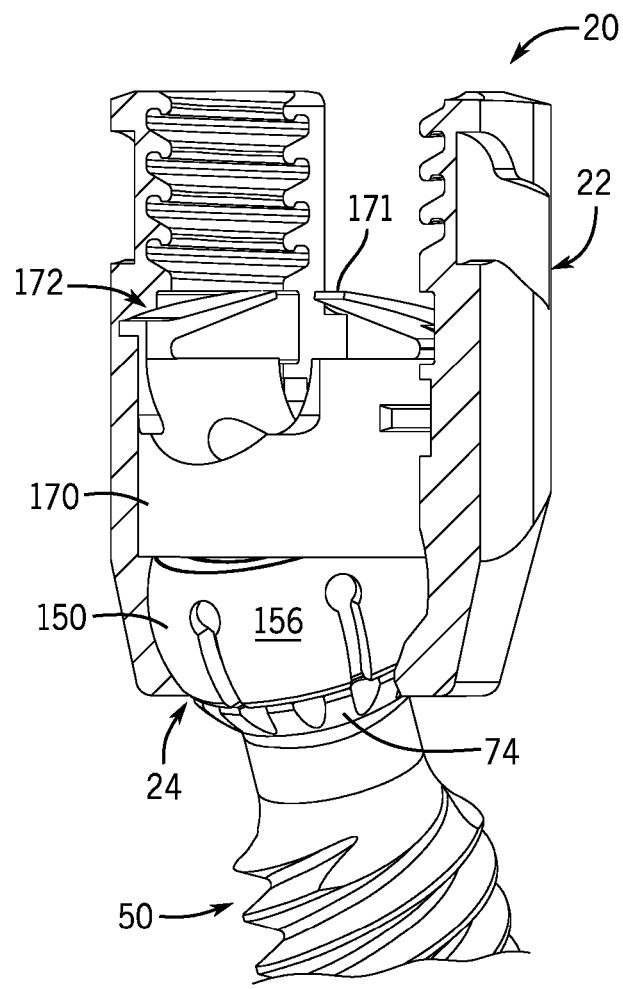
FIG. 34 is a partially cut-away front perspective view of the assembled multiplanar bone anchor assembly with the pre-lock friction fit and the shank head sub-assembly being pivoted to an articulated position.

With reference to FIGS. 33-34, the axially-directed forces used to upload the shank 50 into the receiver sub-assembly 22 can now be released, which in turn releases the compressive load on the resilient upper flanges 172 of the pressure insert 170 and allows them to automatically push the pressure insert 170 and the multiplanar shank head sub-assembly 24 downwardly until the cap retainer 150 (and the bi-spheric shank head 60) are re-secured against the spherical seating surface 136 of the receiver cavity with a frictional engagement, or pre-lock friction fit, without any further manipulation or deployment of the multiplanar pressure insert 170 with tooling. It will be appreciated that the resistance or axially biasing force, and thereby the strength of the pre-lock friction fit, can be controlled by adjusting the shape, thickness, and upward curvature of the resilient upper flanges 172 of the pressure insert 170. The coupling of the universal bi-spheric shank head 60 of the bone anchor or shank 50 with the multiplanar receiver sub-assembly 22 can complete the formation of the multiplanar bone anchor assembly 20 in its initial configuration, one in which the multiplanar bone anchor assembly 20 is ready to be implanted into the vertebrae of a patient or to receive the elongate rod and the closure.

It will be appreciated that the frictional engagement at the interface at the minor diameter 67 between the discontinuous inner spherical surface 158 of the cap retainer 150 and the upper spherical surface 66 of the bi-spheric shank head 60 can be stronger than any frictional engagement at the interface at the major diameter 77 between the spherical outer surface of the cap retainer 156, the concave lower surface 184 of the pressure insert 170, and the spherical seating surface 136 of the receiver 100 that may be provided by the axially-biasing pressure insert 170. As such, any rotational forces or moments created between the bi-spheric shank head 60 and the receiver sub-assembly 22 will cause the entire multiplanar shank head sub-assembly 24 to slide along the interface at the major diameter 77 with the spherical seating surface 136 and the concave lower surface 184 of the pressure insert 170, even when the axially-biasing insert 170 is providing the pre-lock friction fit. Thus, in one aspect, this can advantageously allow for the rotatable implantation, or screwing in, of the anchor portion 84 of a pre-assembled multiplanar bone anchor assembly to a desired depth in the bone of a patient without a corresponding rotation of the multiplanar receiver sub-assembly 22 that is coupled to the bi-spheric shank head 60. This can also advantageously allow for the multiplanar receiver sub-assembly 22 to be secured to the bi-spheric shank head 60 by separate tooling and to be maintained in a desired alignment relative to other elements in a spinal construct throughout both the implantation and rod reduction procedures.

Figure 41:
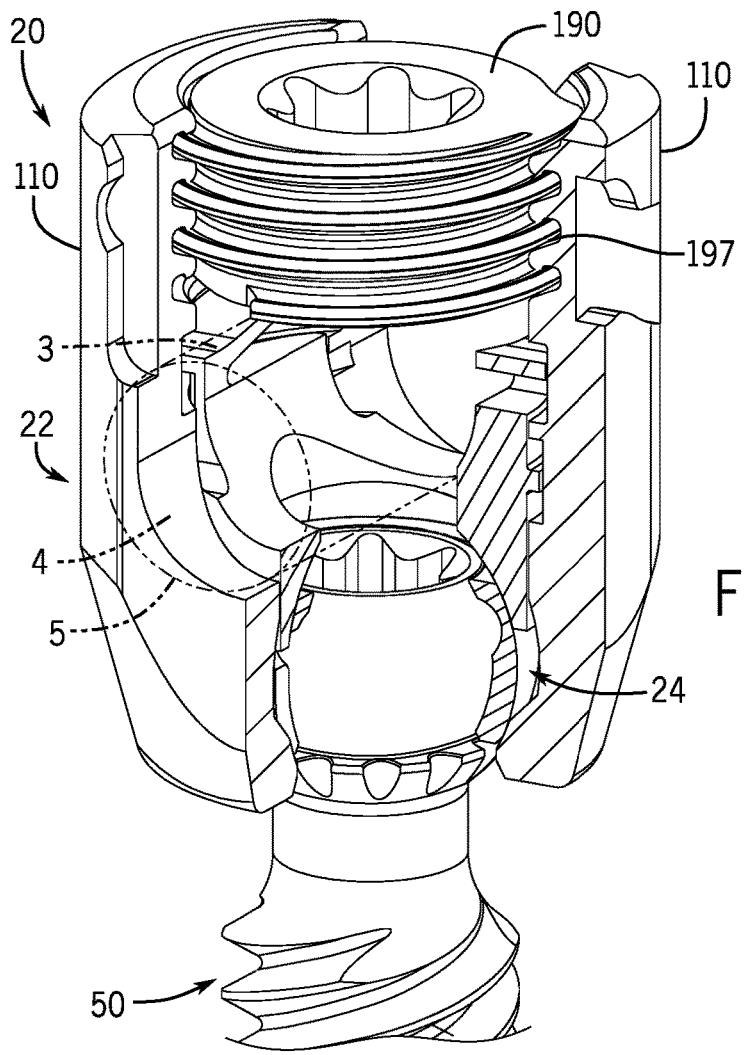
FIG. 41 is a partially cut-away front perspective view of the multiplanar bone anchor assembly, fully assembled with the elongate rod and closure and with the bone anchor in a non-articulated position relative to the receiver.
Figure 42:
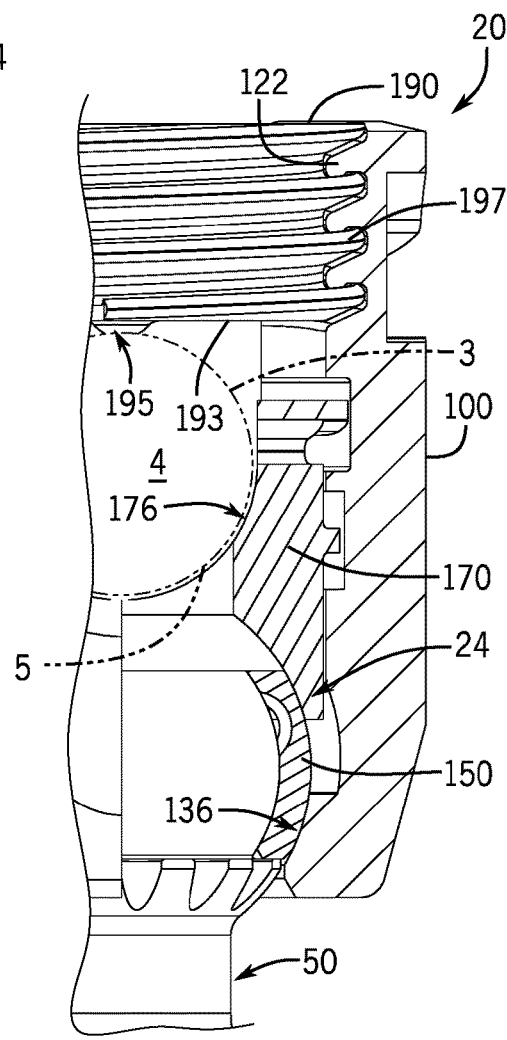
FIG. 42 is a close-up partially cut-away front view of a portion of the fully-assembled multiplanar bone anchor assembly of FIG. 41.

As discussed above in reference to FIGS. 27 and 28, the frictional engagements between the upper portion of the discontinuous outer spherical surface 156 of the cap retainer 150 and the concave lower surface 184 of the pressure insert 170, and between the lower portion of the discontinuous outer spherical surface 156 and the spherical seating surface 136 of the receiver 100, can be sufficient to frictionally secure the cap retainer 150 in the shipping state position, with the central lower opening 165 defined by the inner beveled edge surfaces 159 of the collet fingers 164 being centered adjacent to and aligned with the bottom opening 145 of the receiver 100, prior to coupling with the bone anchor 50. In one aspect this same frictional engagement can also be sufficient to inhibit any pivotal or rotational motion of the articulating, multiplanar shank head sub-assembly 24 (i.e. the combined bi-spherical shank and multiplanar cap retainer after their coupling together) relative to the receiver 100, except by an applied force such as manual manipulation. In other words, once coupled together and prior to downloading the elongate rod 4 into the of the channel 106 and the locking the assembly with the closure 190 (as shown in FIGS. 5 and 41-42), the cap retainer 150 and bone anchor 50 can be pivotably frictionally secured to the receiver 100 with a non-floppy friction fit at the interface at the major diameter 77 between the discontinuous outer spherical surface 156 of the cap retainer 150, the concave bottom surface 184 of the pressure insert 170, and the spherical seating surface 136 of the receiver 100 that will maintain the receiver 100 in position relative to the bone anchor or shank 50 unless moved by the applied force.

In one alternative embodiment of the present disclosure described in more detail below, it is foreseen that both the multiplanar receiver and the multiplanar pressure insert can be reconfigured for manual downwardly deployment of the multiplanar pressure insert using tooling after the bi-spheric shank head has been captured by the multiplanar cap retainer, so as to provide the pre-lock friction fit. For example, the multiplanar pressure insert can be provided with opposite outwardly-projecting flanges that can be positioned with opposed upper recesses formed into the central bore of the receiver, and then the multiplanar pressure insert can be pressed downward or deployed by the tooling while the opposite flanges slide out of the opposed upper recess and move downward to become engaged within opposed lower recesses. Other mechanical interactions between the multiplanar pressure insert and the multiplanar receiver are also possible. In addition, the multiplanar pressure insert can be pressed or rotated into the initial position in which the opposite outwardly-projecting flanges are positioned with opposed upper recesses.

In yet another alternative embodiment of the present disclosure, it is foreseen that both the multiplanar receiver and the multiplanar pressure insert can be reconfigured so that tooling may be used to temporarily hold the multiplanar pressure insert down in a biased or even in a temporarily locked position within the multiplanar receiver sub-assembly, until there is a final locking of the multiplanar bone anchor assembly with the elongate rod and via the closure.

Figure 35:
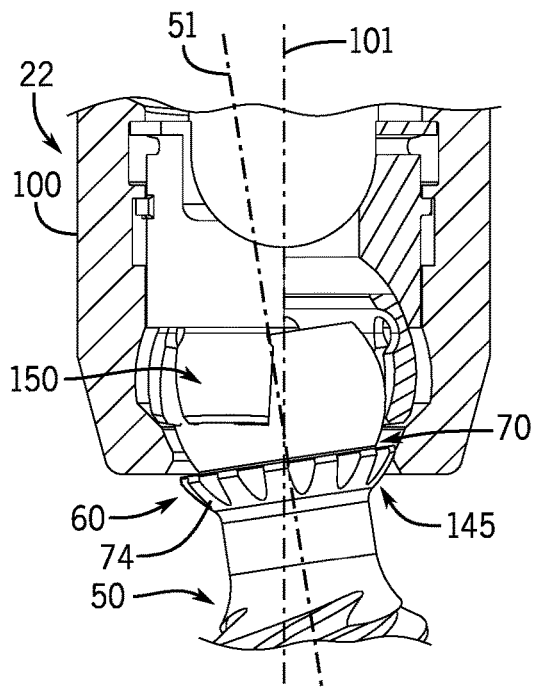
FIG. 35 is a partially cut-away front view of the bi-spheric shank head being uploaded into the multiplanar receiver sub-assembly in a mis-aligned orientation, showing the range of available misalignment as the outer lip of the lower ledge passes through the bottom opening of the receiver.
Figure 36:
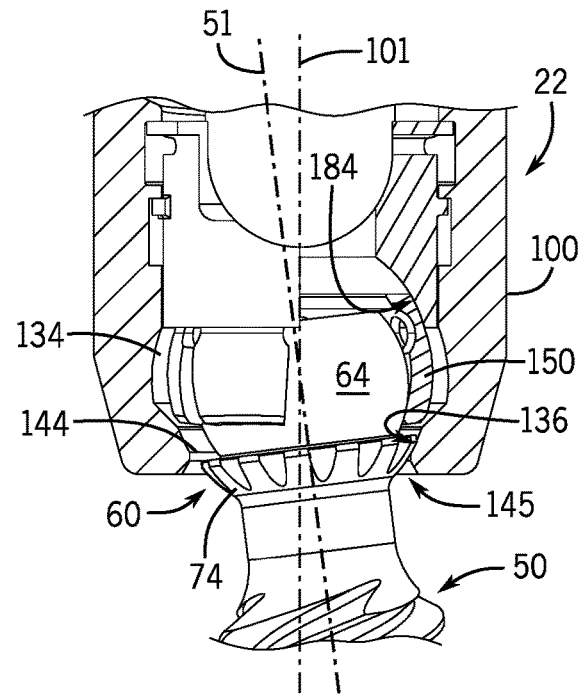
FIG. 36 is another partially cut-away front view of the bi-spheric shank head being uploaded into the multiplanar receiver sub-assembly in a mis-aligned orientation, showing the range of available misalignment as the outer lip of the lower ledge passes moves onto the seating surface of the receiver.
Figure 37:
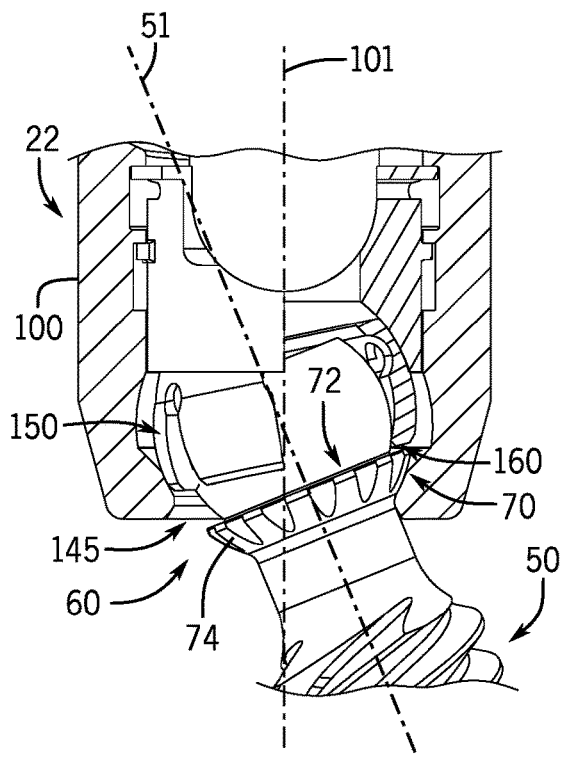
FIG. 37 is another partially cut-away front view of the bi-spheric shank head being uploaded into the multiplanar receiver sub-assembly in a mis-aligned orientation, showing the range of available misalignment as the lower ledge of the shank head begins to engage the discontinuous annular bottom surface of the cap retainer.
Figure 38:
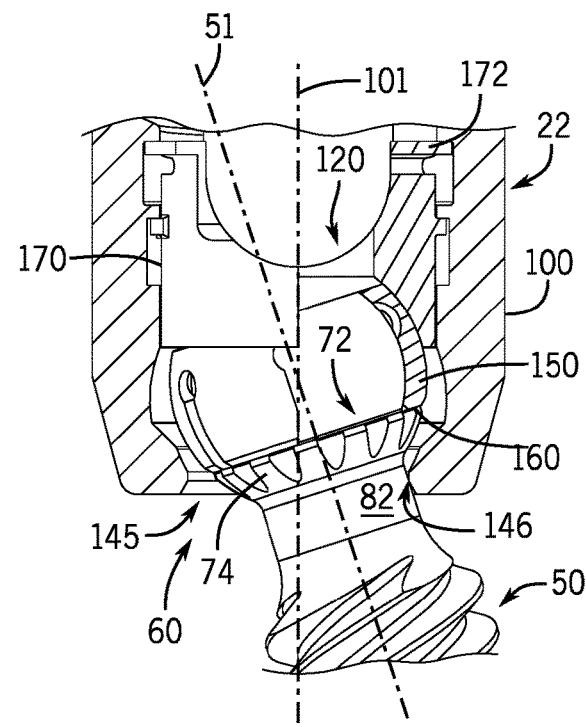
FIG. 38 is another partially cut-away front view of the bi-spheric shank head being uploaded into the multiplanar receiver sub-assembly in a mis-aligned orientation, showing the range of available misalignment as the lower ledge of the shank head becomes fully engaged with the discontinuous annular bottom surface of the cap retainer.

Illustrated in FIGS. 35-38 is the range of misalignments between the longitudinal axis 51 of the shank 50 and the vertical centerline axis 101 of the receiver 100 of the multiplanar receiver sub-assembly 22 that can be accommodated during the assembly of the receiver sub-assembly 22 to the bi-spheric shank head 60. For example, during the process of uploading the bi-spheric shank head 60 into the multiplanar receiver sub-assembly 22 described above, the degree of misalignment between the two axes can be most limited as the outer lip of the annular lower ledge 70 of the lower partial spherical portion 74 passes through the bottom opening 145 of the receiver 100, as shown in FIG. 35. However, and with reference to FIG. 36, the degree of misalignment can increase as soon as a substantial portion of the outer lip passes through the lowermost cylindrical surface 144 that defines the bottom opening 145 and moves upward onto the spherical seating surface 136 of the internal cavity 134. At the same time, the upper partial spherical portion 64 continues to be engaged and captured by cap retainer 150 that remains centered against the concave lower surface 184 of the pressure insert 170. Upon the leading portion of the lower ledge 70 of the lower partial spherical portion 74 engaging with the discontinuous annular bottom surface 160 of the cap retainer 150, as shown in FIG. 37, the cap retainer 150 can slidably tilt or rotate against the concave lower surface 184 until the discontinuous annular bottom surface 160 becomes fully engaged with the upward facing planar surface 72 of the lower ledge around the entire circumference of the bi-spheric shank head 60, as shown in FIG. 38. Also shown in FIG. 38, in one aspect the neck 82 of the shank 50 can contact the lowermost tapered surface 146 of the central bore 120 toward the end of the assembly sequence to provide the maximum degree of misalignment defined by the dimensions of the receiver 100.

Figure 39:
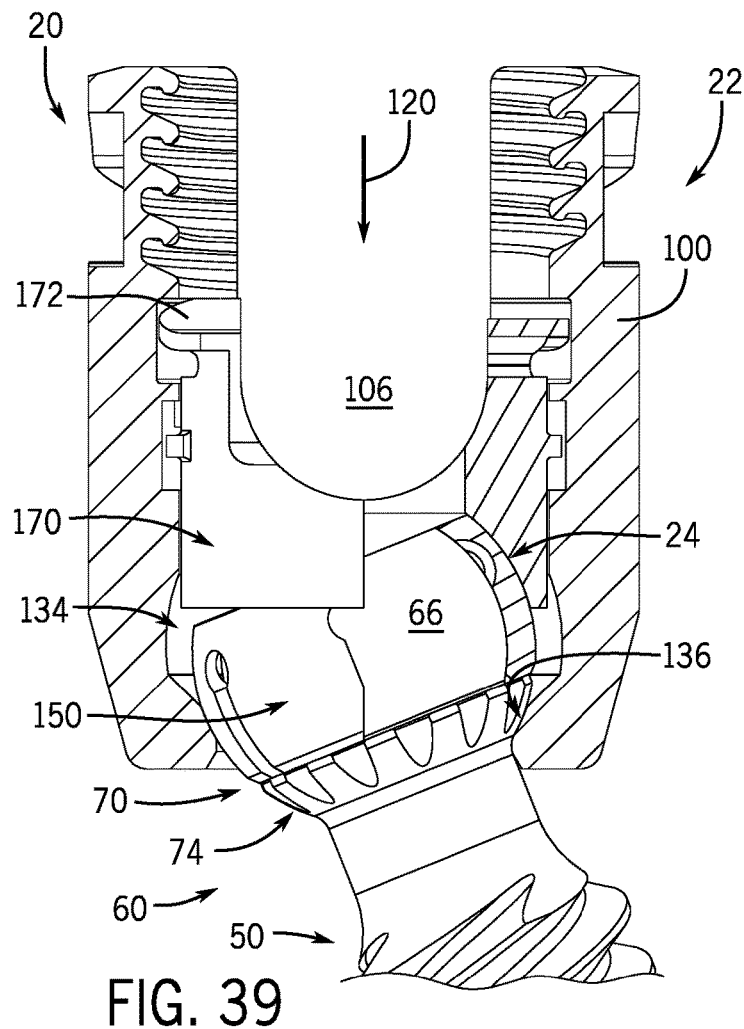
FIG. 39 is a partially cut-away front view of the multiplanar bone anchor assembly prior to complete assembly with the elongate rod and closure and with the bone anchor secured in an articulated position relative to the receiver by the pre-lock friction fit.
Figure 40:
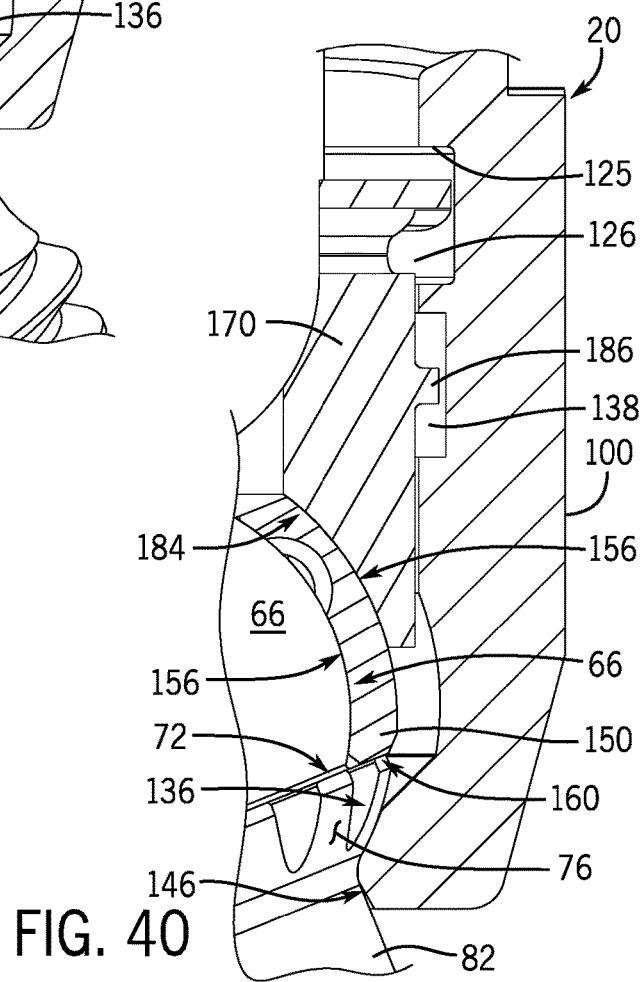
FIG. 40 is a close-up cross-sectional side view of the multiplanar bone anchor assembly of FIG. 39.

Once the cap retainer 150 is fully engaged with the bi-spheric shank head 60, the compressed upper flanges 172 of the pressure insert 170 can resiliently expand back downward toward their neutral position to create the downwardly-directed resistance or axially biasing force that presses back downward on the upper portions of the articulated cap retainer 150, as shown in FIGS. 39-40. As described above, this biasing force can drive the lower portions of the discontinuous outer spherical surface 156 of the cap retainer 150 and the lower spherical surface 76 of the bi-spheric shank head 60 downward against the spherical seating surface 136 of the internal cavity 134 to automatically establish the pre-lock friction fit without any further manipulation or deployment of the multiplanar bone anchor assembly with tooling.

Illustrated in FIGS. 41-44 is the multiplanar bone anchor assembly 20 after final assembly with the elongate rod 4 and the single-piece closure 190 into the locked configuration. For instance, after a desired alignment of the rod channel 106 of the receiver 100 has been achieved via manipulation of the multiplanar receiver sub-assembly 22 relative to the multiplanar shank head sub-assembly 24, with the axially-biased multiplanar pressure insert 170 providing a pre-lock friction fit, the elongate rod 4 can be installed (i.e. reduced) into the rod channel 106, such as with instruments and/or breakoff extensions on the upright arms 110 of the receiver 100, until the lowermost or underside surface 5 of the elongate rod approaches the upward-facing rod seating surface 176 of the pressure insert 170. The closure 190 can then be installed into the upper portion of the central bore 120 of the receiver (or breakoff extensions), in which the continuous outer guide and advancement structure 197 of the closure 190 rotatably engages the discontinuous guide and advancement structure 122 formed into the interior faces of the upright arms 110 of the receiver 100 (and breakoff extensions). The closure 190 can be threaded downwardly until the bottom surface 193 of the closure 190, or the downwardly-projecting central projection 195 protruding therefrom, engages the upper surface 3 of the elongate rod. Further rotation and torquing of the closure 190 can then be used to drive the elongate rod 4 downward onto the multiplanar pressure insert 170, which in turn further drives the multiplanar shank head sub-assembly 24 downward onto the spherical seating surface 136 of the internal cavity 134 of the receiver 100 to achieve a final locking of the multiplanar bone anchor assembly 20, in which the multiplanar receiver sub-assembly 22 can no longer pivot or rotate relative to the shank or bone anchor 50.

Independent Lock Bone Anchor Assembly

Figure 43:
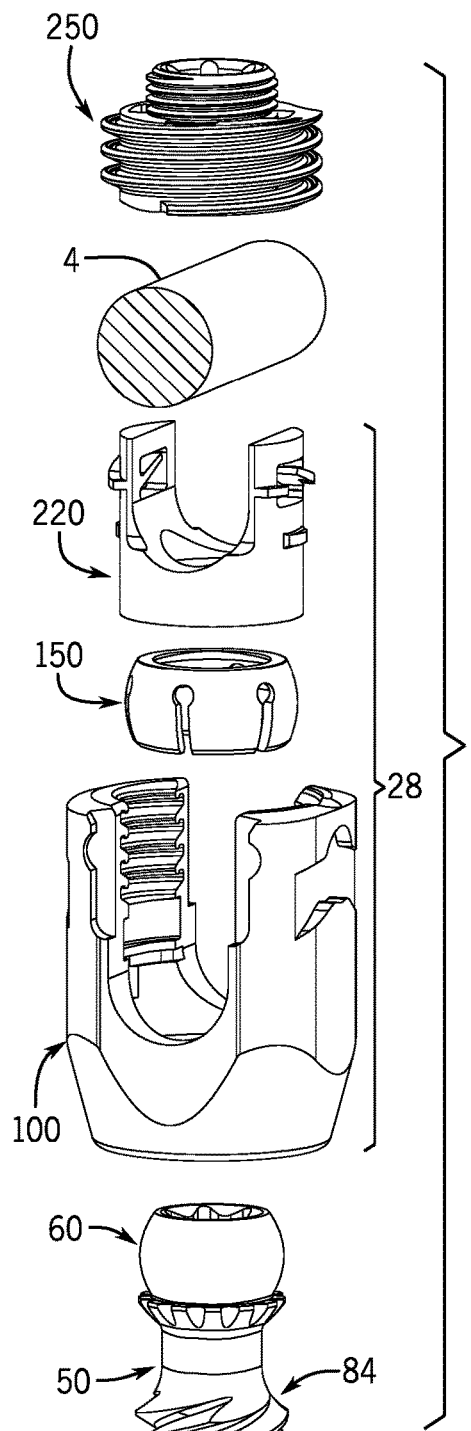
FIG. 43 is an exploded perspective view of a multiplanar IL ("Independent Lock") embodiment of a bone anchor assembly, in accordance with the representative embodiment of the multi-component spinal fixation system shown in FIG. 1.
Figure 44:
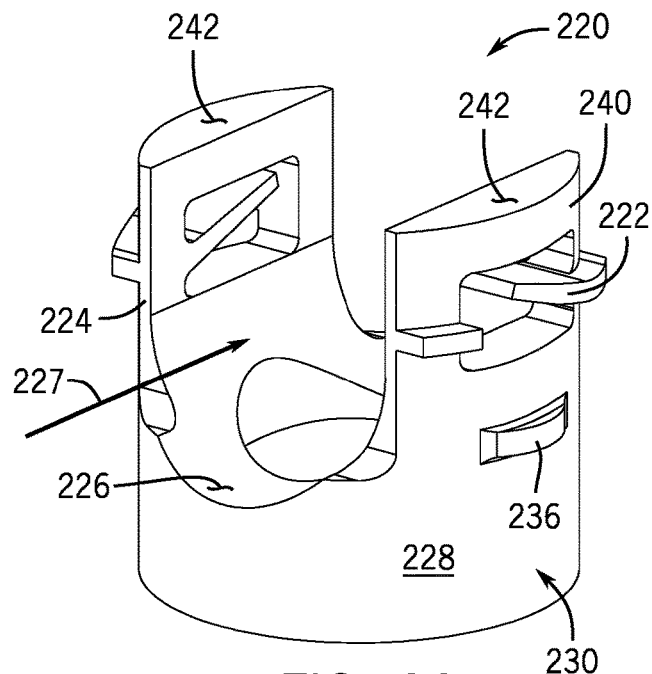
FIG. 44 is a top perspective view of the IL pressure insert of the multiplanar IL bone anchor assembly of FIG. 43.
Figure 45:
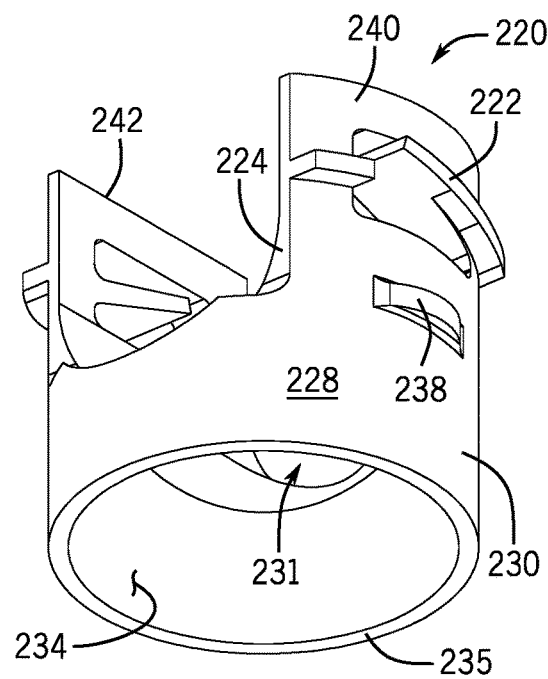
FIG. 45 is a bottom perspective view of the IL pressure insert of FIG. 44.
Figure 46:
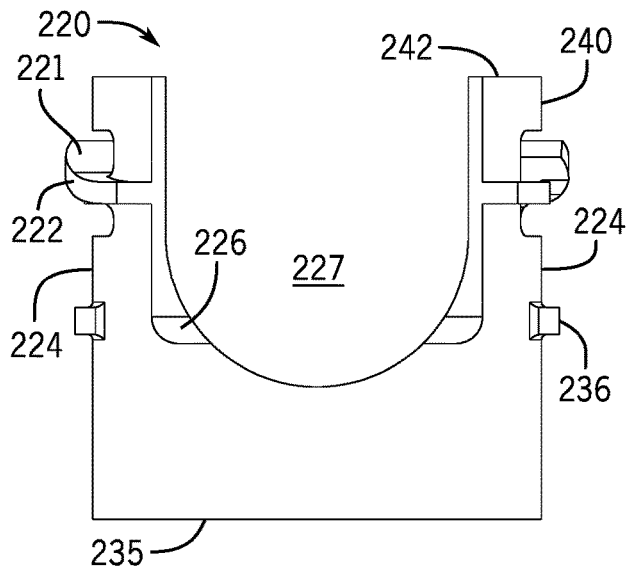
FIG. 46 is a front side view of the IL pressure insert of FIG. 44.
Figure 47:
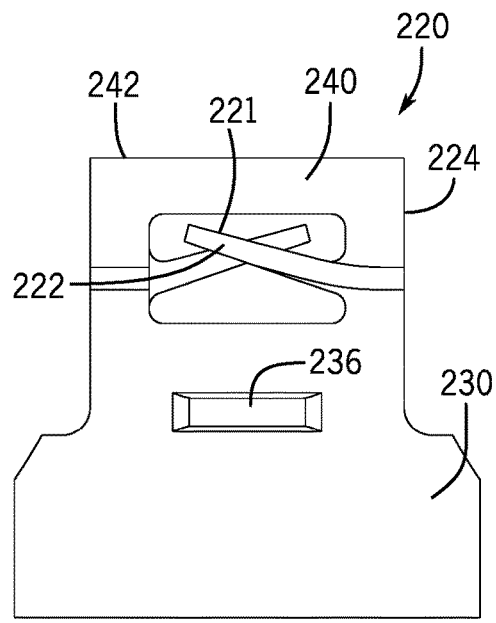
FIG. 47 is a side view of the IL pressure insert of FIG. 44.
Figure 48:
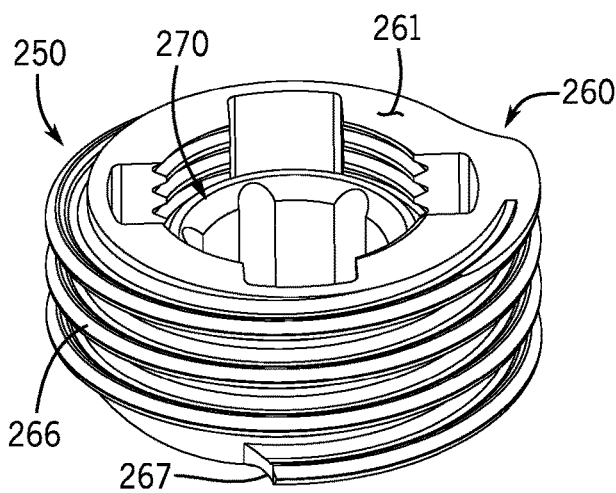
FIG. 48 is a top perspective view of the two-piece closure of the multiplanar IL bone anchor assembly of FIG. 43.
Figure 49:
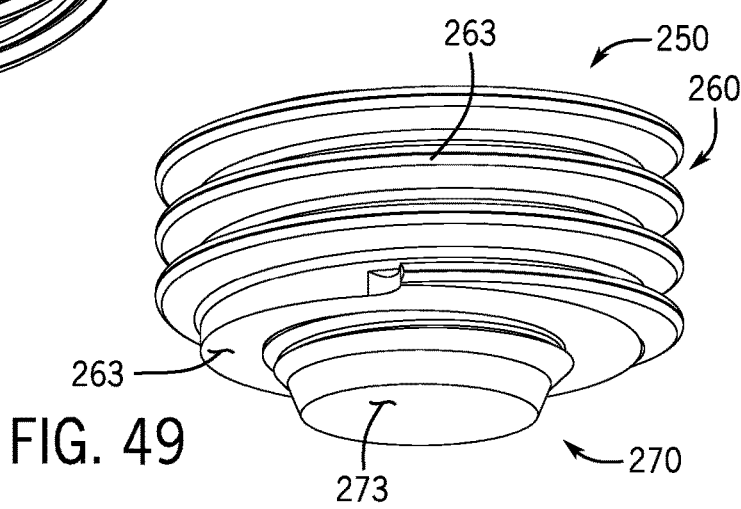
FIG. 49 is a bottom perspective view of the two-piece closure of FIG. 48.
Figure 50:
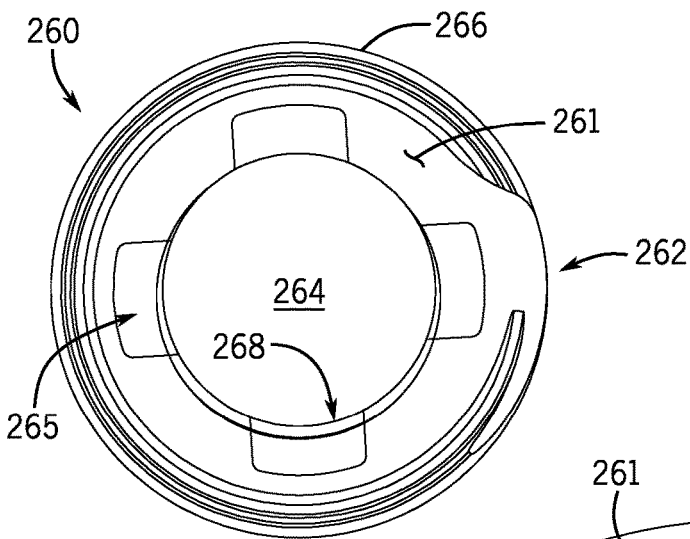
FIG. 50 is a top view of the outer ring of the two-piece closure of FIG. 48.
Figure 51:
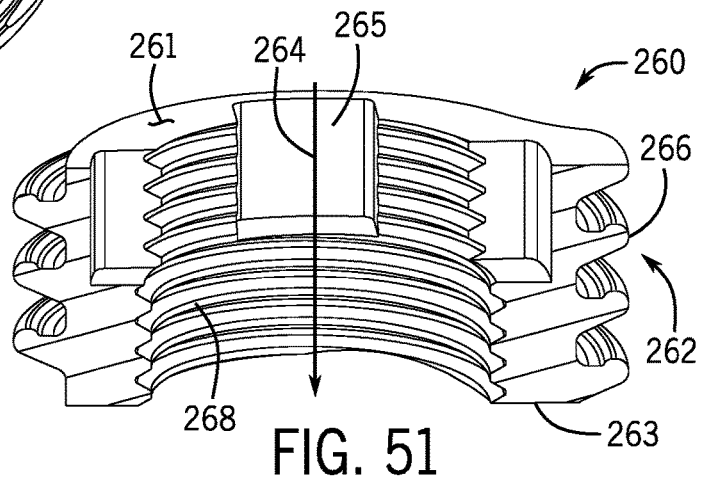
FIG. 51 is a cross-sectional front perspective view of the outer ring of the two-piece closure of FIG. 48.
Figure 52:
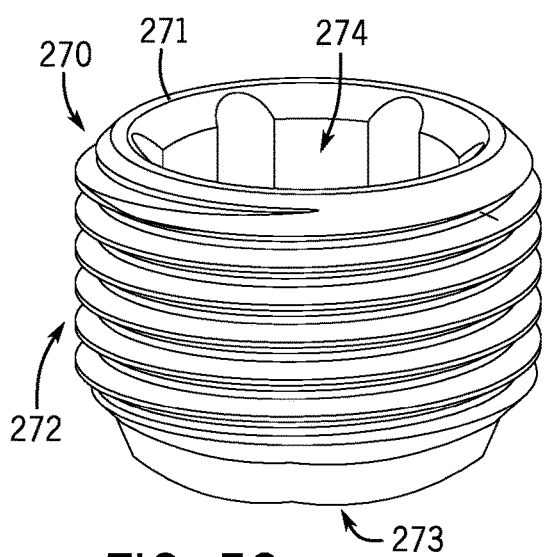
FIG. 52 is a front perspective view of the center screw of the two-piece closure of FIG. 48.
Figure 53:
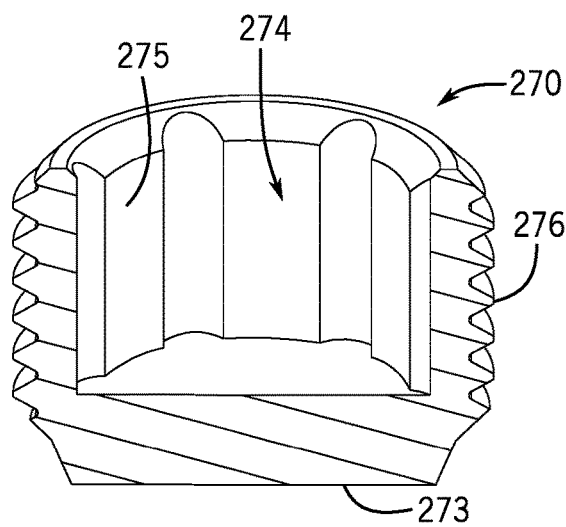
FIG. 53 is a cross-sectional front perspective view of the center ring of the two-piece closure of FIG. 48.

Referring now to FIG. 43, illustrated therein is an exploded perspective view of another representative embodiment 26 of the multiplanar bone anchor assembly illustrated in FIG. 1(c), but which is configured to provide an independent lock ("IL") functionality in which the position of an IL receiver sub-assembly 28 can be immovably locked to the bi-spheric shank head 60 of the bone anchor or shank 50 independent of the elongate rod 4 being locked within the channel 106 of the receiver 100. This multiplanar IL bone anchor assembly 26 can include the same bone anchor or shank 50 described above, having a bi-spheric shank head 60 and an anchor portion 84 opposite the bi-spheric shank head 60 for securement or attachment to the bone of a patient. The multiplanar IL bone anchor assembly 26 can also include a multiplanar receiver 100 that can be initially pivotably secured to the bi-spheric shank head 60 with a number of separate internal components that have been pre-assembled into the internal cavity 134 and the rod channel 106 of the receiver 100 to form the multiplanar IL receiver sub-assembly 28. These internal components can include, but are not limited to, the pivoting or articulating multiplanar cap retainer 150 and a multiplanar IL pressure insert 220. Before or after the elongate rod 4 has been positioned within the lower portion of the rod channel 106, a two-piece closure 250 can be threadably or otherwise secured into an upper portion of the rod channel 106 to separately apply pressure to upper surfaces of the IL pressure insert 220 and to the upper surface 3 of the elongate rod 4, eventually locking both the elongate rod 4 and the IL receiver sub-assembly 28 into a final locked position relative to the bone anchor or shank 50.

The primary difference between the multiplanar IL bone anchor assembly 26 and the previous embodiment can be the alternative IL pressure insert 220 and the alternative two-piece closure 250 that function together to provide the independent lock functionality. Moreover, it will be appreciated that the receiver 100 and cap retainer 150 of the IL multiplanar bone anchor assembly 26 shown in FIG. 43 can be the same as or substantially similar to those included in the multiplanar bone anchor assembly 20 described above, hence providing an additional degree of component-type modularity that can reduce the number of different individual components required to manufacture and assemble a spinal construct using the spinal fixation system 10 (see FIG. 1) of the present disclosure.

With reference to FIGS. 44-47, the IL pressure insert 220 can have substantially the same construction and features of the pressure insert 170 described above, with the exception that the upper end 225 of each insert arm 224 can extend above and cross over the top of the integral, resilient upper flange 222 to form a crossover structures 240 having a top surface 242 that is configured to be engaged by the outer ring of the two-piece closure 250. As such, the top surfaces 242 of the crossover structure 240 can be positioned within the region of the discontinuous guide and advancement structure 122 formed into the interior faces 104 of the upright arms 110 of the receiver 100 (see FIGS. 7-10) upon the installation of the IL pressure insert into the central bore 120. While the upper flanges 222 of the insert arms 224 can still be configured to slide into the discontinuous inner recess 126 of the upright arms 110 of the multiplanar receiver 100, it is understood that the size and shape of the upper flanges 222 can also be modified or repositioned to better accommodate the crossover structures 240.

Other aspects of the IL pressure insert 220 can be identical or substantially similar to those of the pressure insert 170 described above, including the pair of insert arms 224 and the lower base portion 230 together defining a cylindrical outer surface 228 that is sized to be slidably received within the central bore of the multiplanar receiver. Similarly, the upward-facing rod seating surface 226 extending in between the insert arms 224 can form an insert channel 227 that is rotatably alignable with the channel of the receiver after the pressure insert has been downloaded into the central bore. The IL pressure insert 220 can also include the spherical, downwardly-opening concave lower surface 234, extending upward and inward from the annular planar bottom edge surface 235, and that is engageable with the discontinuous spherical outer surface of the cap retainer, as well as the central tool-receiving aperture 231 defined by the inner cylindrical surface 232 that is configured to slidably receive a drive tool (not shown). The IL pressure insert 220 can further include the opposite indexing nubs 236 or protuberances located on the sides of the insert, under the resilient upper flanges 22, that can become positioned with the opposed vertical side pockets 138 formed into the central bore 120 of the receiver 100 upon rotation of the pressure insert 170 into its rotated position.

With reference to FIGS. 48-53, the two-piece closure 250 can include an outer ring 260 comprising a generally cylindrical body 262 having an annular top surface 131, an annular bottom surface 263, and a central through-aperture 264. A continuous guide and advancement structure 266 with a start 267 can be formed into the side surfaces of the cylindrical body 262 and configured to rotatably mate with the discontinuous guide and advancement structure formed into interior faces of the upright arms of the receiver. As shown in the drawings, the guide and advancement structure 266 can be a helically-wound interlocking flange that is mateable with the complementary flange formed into the multiplanar receiver 100. Nevertheless, and as described above with reference to the receiver, other versions of the continuous guide and advancement structure 266 complementary with that formed into the multiplanar receiver are also possible and considered to fall within the scope of the present disclosure.

The central through-aperture 264 of the outer ring 260 includes an internal guide and advancement structure, in this case an internal thread 268, that is configured to threadably receive the center screw 270. As can be seen in the drawing figures, the center screw 270 also comprises a generally cylindrical body 272, but one that is much smaller and having an external or outer thread 276 that is complementary with the internal thread 268 of the central through aperture 264. The center screw 270 further includes an annular top surface 271, a solid or continuous bottom surface 273, and a central closed-off aperture 274 formed as a drive structure or internal drive socket 275 extending downwardly from the annular top surface 271 toward the bottom surface. The outer ring 260 can also have a drive structure, in this case a plurality of downward-extending recesses 265 formed into the upper portion of the central through-aperture 264, and which may interrupt the upper portions of the internal thread 268.

As discussed in more detail below, the annular bottom surface 263 of the outer ring 260 is configured to engage with the top surfaces 242 of the crossover structure 240 of the IL pressure insert 220, while the closed-off bottom surface 273 of the center screw 270 is configured to engage the elongate rod. Other aspects of the two-piece closure 250 will be apparent to one of skill in the art upon further review of the drawing figures.

Figure 54:
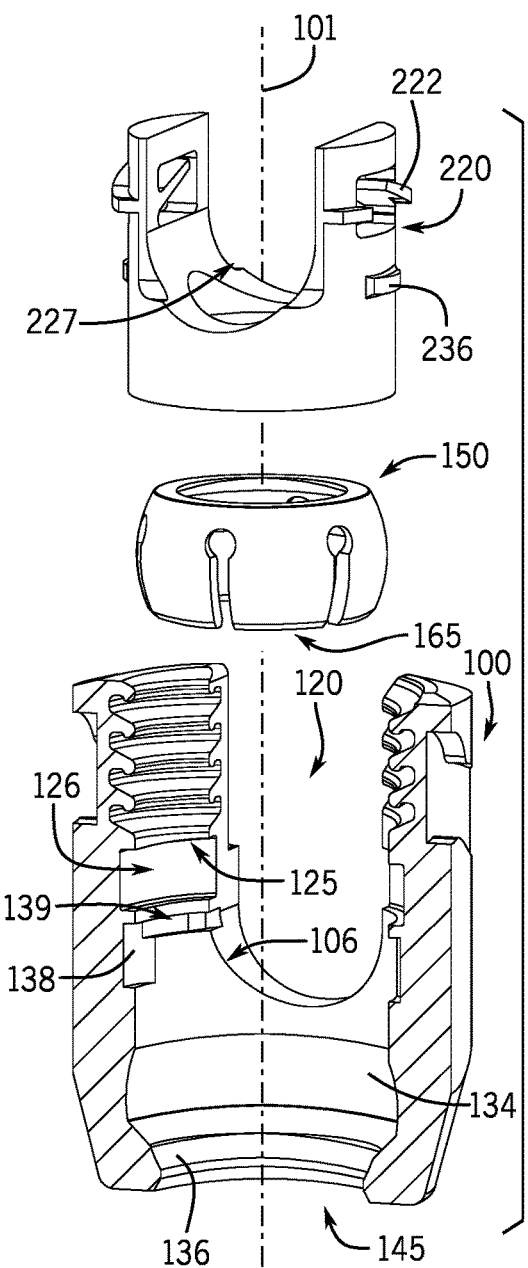
FIG. 54 is an exploded partially cut-away front perspective view of the components of the multiplanar IL receiver sub-assembly of FIG. 43 prior to their pre-assembly into a shipping configuration.
Figure 55:
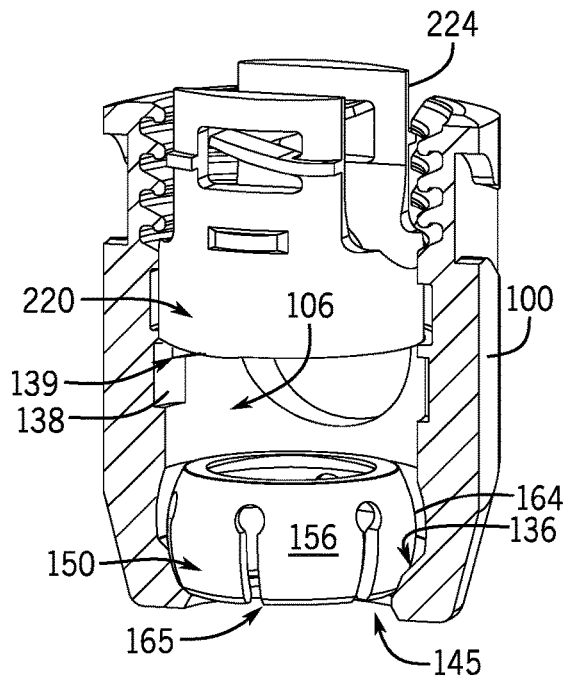
FIG. 55 is a partially cut-away front perspective view of the receiver of FIG. 54, together with the seated multiplanar cap retainer and with the IL pressure insert being downloaded through the open channel of the receiver.

FIGS. 54-59 illustrate the pre-assembly of the multiplanar versions of the receiver 100, the cap retainer 150, and IL pressure insert 222 together to form the multiplanar IL receiver sub-assembly 28 in a self-biased shipping state configuration, which method of assembly can be substantially the same as that described above with respect to the multiplanar, non-IL, single-piece closure embodiment. As shown in FIGS. 54-55, for example, the cap retainer 150 can be downloaded through the central bore 120 until the discontinuous outer spherical surface 156 engages with the spherical seating surface 136 at the lower end of the cavity 134 of the receiver 100. If needed, the cap retainer 150 can be rotated to a horizontal position resting on the spherical seating surface 136, as shown in FIG. 55, with the central lower opening 165 defined by the inner beveled edge surfaces 159 of the collet fingers 164 being centered adjacent to and aligned with the bottom opening 145 of the receiver 100.

Figure 56:
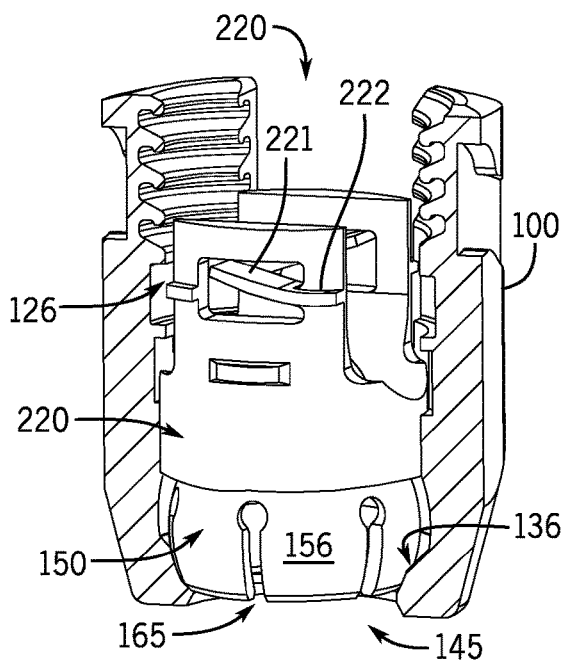
FIG. 56 is a partially cut-away front perspective view of the receiver of FIG. 54, together with the seated multiplanar cap retainer and with the IL pressure insert being further downloaded through the open channel of the receiver.

After the cap retainer 150 is seated on the spherical seating surface 136 of the receiver 100, the IL pressure insert 220 may then be top-loaded or down-loaded into the central bore 120 and installed into its the shipping state position above the cap retainer 150. This can be achieved by positioning the IL pressure insert 220 above the central bore 120 with the insert arms 224 and their radially-outwardly projecting upper flanges 222 being aligned with the open channel 106, and then downloading the IL pressure insert 220 through the channel 106 (also FIG. 55) until the leading edges of the upper flanges 222 reach the level of the discontinuous inner recess 126 formed into the central bore 120 and the outwardly-projecting indexing nubs 236 reach the level of the horizontal access recesses 139, as shown in FIG. 56. In this initial downloaded pre-rotation position, the concave lower surface 234 of the IL pressure insert 220 can still be spaced above the upper ring portion 154 and discontinuous outer spherical surface 156 of the cap retainer 150.

Figure 57:
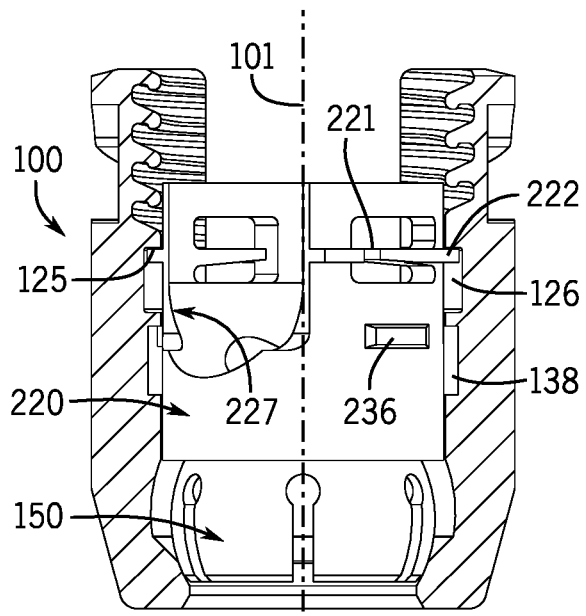
FIG. 57 is a partially cut-away front view of the receiver of FIG. 54, together with the seated multiplanar cap retainer and the downloaded and partially rotated IL pressure insert.
Figure 58:
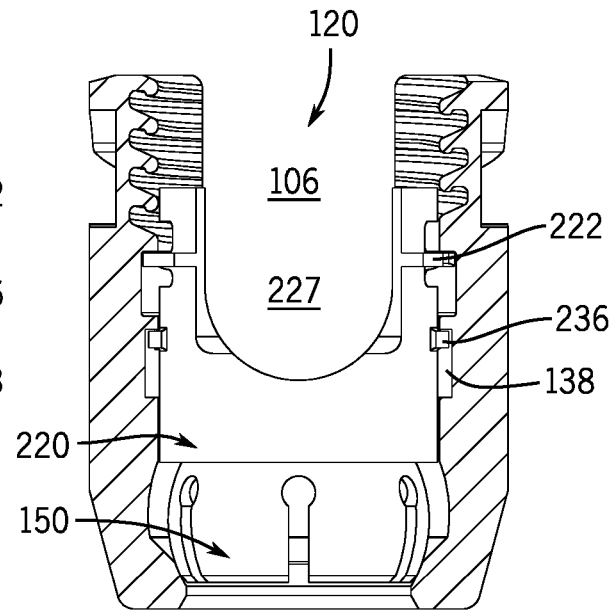
FIG. 58 is a partially cut-away front view of the receiver of FIG. 54, together with the seated multiplanar cap retainer and the downloaded and almost completely rotated IL pressure insert.

After reaching the initial downloaded pre-rotation position (FIG. 56), the IL pressure insert 220 may then be rotated around its longitudinal axis (which is co-axial with the vertical centerline axis 101 of the receiver 100) so that the leading edges of the radially or outwardly-projecting and upwardly-angled upper flanges 222 begin to enter into the discontinuous inner recess 126 of the upright arms 110 and the outwardly-projecting indexing nubs 236 enter the horizontal access recesses 139. Continued rotation of the IL pressure insert 220 can cause the top surfaces 221 of the upper flanges 222 to slidably resiliently engage with the downward-facing upper arcuate surfaces 125 of the discontinuous recess 126. Because the vertical location of the pressure insert 220 within the central bore 120 is temporarily fixed by the location of the indexing nubs 236 within the horizontal access recesses 139, this slidable engagement will cause the resilient upper flanges 222 to deflect downward under compression in order to enter the discontinuous recess 126, as shown in FIG. 57. The rotation of the IL pressure insert 220 can continue for a full 90 degrees or quarter turn, until the rod channel 227 of the insert 220 becomes aligned with the open channel 106 of the receiver 100, the compressed upper flanges 222 become fully positioned within the discontinuous inner recess 126 of the interior faces 104 of the upright arms 104, and the indexing nubs 236 almost completely slide into the opposed vertical side pockets 138 of the central bore 120, as shown in FIG. 58.

Figure 59:
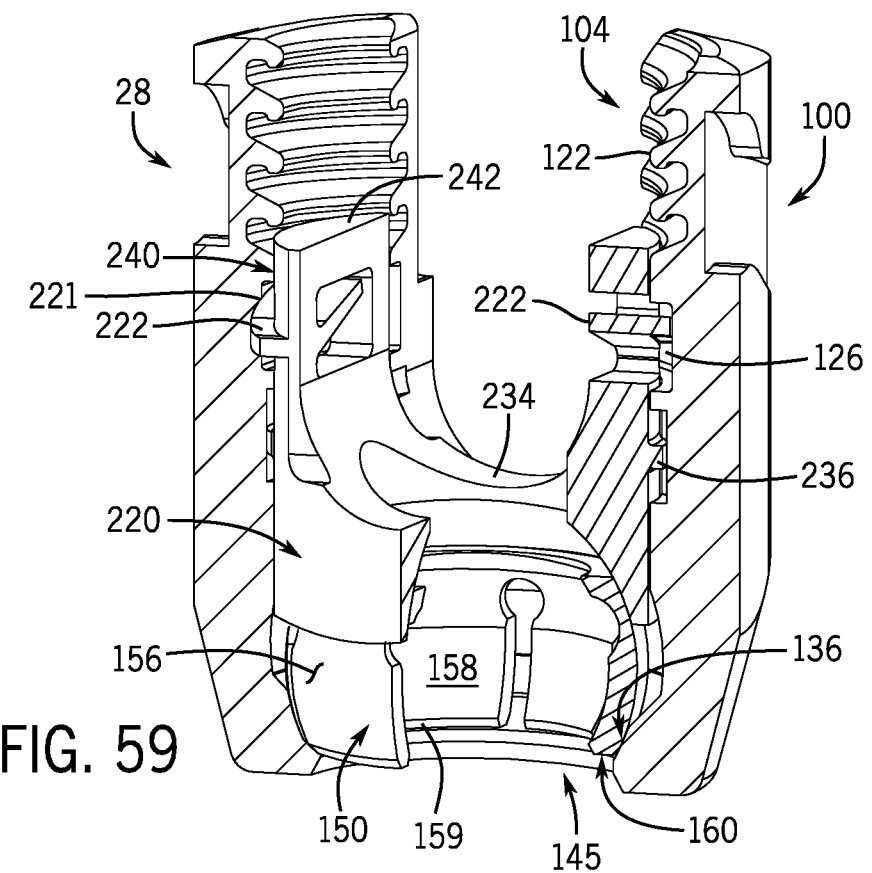
FIG. 59 is a partially cut-away front perspective view of the receiver of FIG. 54, together with the seated multiplanar cap retainer and the IL pressure insert being fully rotated therein and automatically deployed to form a pre-assembled multiplanar IL receiver sub-assembly in the shipping state configuration.
Figure 60:
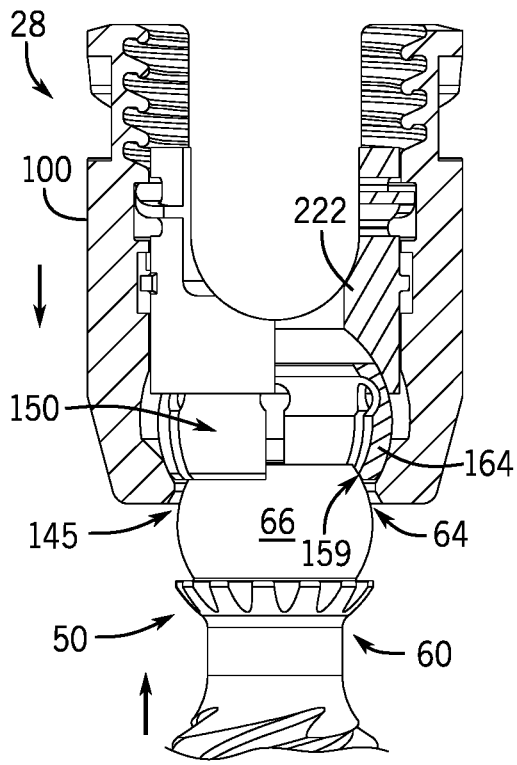
FIG. 60 is a partially cut-away front view of the multiplanar IL receiver sub-assembly moving downward until the bi-spheric shank head engages the cap retainer secured within the receiver by the IL pressure insert.

As soon as the indexing nubs 236 exit the horizontal access recesses 139 and completely enter into the opposed vertical side pockets 138, the compressed upper flanges 222 can release to drive the pressure insert 220 downward until the concave lower surface 234 of the IL pressure insert 220 engages an upper portion of the discontinuous outer spherical surface 156 of the cap retainer, as shown in FIG. 59, with the downward movement of the IL pressure insert 220 also causing the indexing nubs 236 to move downward within the side pockets 138 and below the horizontal access recesses 139 to inhibit rotation of the pressure insert 170, either clockwise or counter-clockwise, out of its rotated and aligned position in which the rod channel 227 of the insert 220 is aligned with the open channel 106 of the receiver 100. At same time, the continued compressive engagement between the trailing portion of the upward-facing top surfaces 221 of the upper flanges 222 and the downward-facing upper arcuate surfaces 125 of the discontinuous inner recess 126 can also bias the pressure insert 220 downwardly to engage and drive the cap retainer 150 downward against the spherical seating surface 136, so as to establish the frictional engagement between the concave lower surface 234 of the pressure insert 220, the discontinuous outer spherical surface 156 of the cap retainer 150, and the spherical seating surface 136 of the internal cavity 136 of the receiver. As described above, this frictional engagement, or pre-lock friction fit, can stabilize and inhibit motion of the cap retainer 150 within the internal cavity 134 of the receiver 100 to prevent any subsequent rotation or misalignment of the cap retainer 150 relative to the bottom opening 145 that would impede the uploading of the bi-spheric shank head of the shank during assembly.

Also shown in FIG. 59, the top surfaces 242 of the crossover structure 240 of the IL pressure insert 220 can extend upward into the region of the discontinuous guide and advancement structure 122 formed into the interior faces 104 of the upright arms 110 of the receiver 100, in preparation for providing the independent lock functionality. Upon the resiliently axially-biased pressure insert 170 being rotated into its fully installed position within the receiver above the cap retainer 150, the pre-assembly of the multiplanar IL receiver sub-assembly 28 now complete.

With reference to FIGS. 60-63 that illustrate the assembly of the IL receiver sub-assembly 28 to the bi-spheric shank head 60 of the shank or bone anchor 50, the method of assembly can also be substantially the same as that described above with respect to the multiplanar, non-IL single-piece closure embodiment, with the IL pressure insert 222 also providing the same automatic or self-engaging pre-lock friction fit feature that can be established while avoiding the use of insert tool deployment or additional tooling. In particular, and with initial reference to FIG. 60, the IL receiver sub-assembly 28 can be first positioned above the proximal end of the bone anchor 50 with the expandable central lower opening of the cap retainer 150, which is centered within the bottom opening 145 of the receiver 100, being generally aligned with the upper portion of the upper partial spherical portion 64 of the bi-spheric shank head 60. The IL receiver sub-assembly 28 is then dropped downward (or the bone anchor is moved upward, depending on the frame of reference of the reader) until the upper spherical surface 66 of the bi-spheric shank head 60 passes upward through the bottom opening 145 of the receiver 100 to engage the inner beveled edge surfaces 159 of the collet fingers 164 that define the central lower opening 165.

Figure 61:
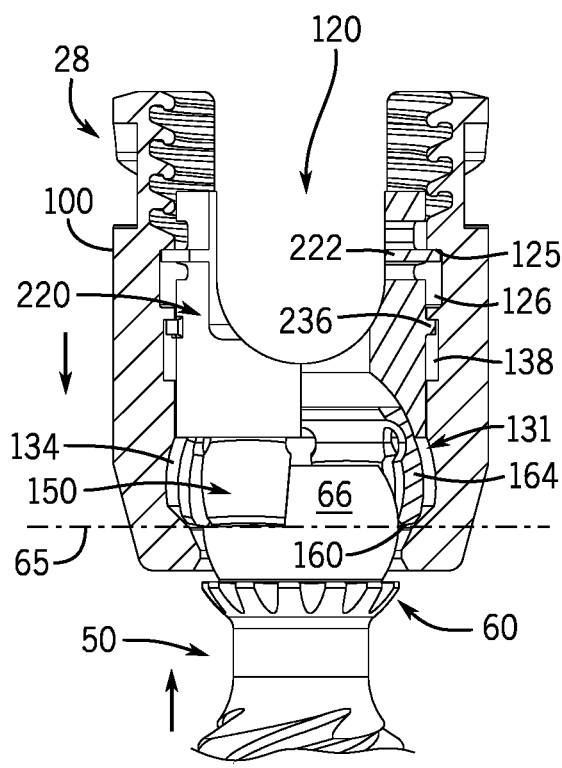
FIG. 61 is a partially cut-away front view of the multiplanar IL receiver sub-assembly continuing to move downward and the cap retainer and IL pressure insert being pushed upward to their uppermost positions, and the bi-spheric shank head continuing to drive upward as it expands the cap retainer within the internal cavity until reaching the maximum expansion of the cap retainer.

As the IL receiver sub-assembly 28 continues to move downward (or the bone anchor moves upward), as shown in FIG. 61, the bi-spheric shank head 60 begins to push both the cap retainer 150 and the IL pressure insert 220 upwards within the internal cavity 134 and the central bore 120 of the receiver 100, respectively, thereby compressing the radially-projecting and upwardly-angled upper flanges 222 of the IL pressure insert against the immovable upper arcuate surfaces 125 of the discontinuous recess 126. At the same time, the central lower opening of the cap retainer 150 begins to expand as the cap retainer 150 enters the upper expansion portion 131 of the internal cavity 134, thereby allowing the inner beveled edge surfaces of the collet fingers 164 that are adjacent to the discontinuous annular bottom surface 160 of the cap retainer 150 to spread apart as they scrape downwards across the upper spherical surface 66 of the bi-spheric shank head 60, pushing any bone debris and/or soft tissue located on the outer surface downwards before them. The IL pressure insert 220 quickly reaches its uppermost position within the central bore 120 defined by the upper surfaces of the indexing nubs 236 abutting against the downward-facing upper surfaces of the vertical side pockets 138, after which the collet fingers 164 of the cap retainer 150 continue to be expanded within the expansion portion 131 of the internal cavity 134 by the upward movement of the bi-spheric shank head 60, pushing any bone debris and/or soft tissue located on the upper spherical surface 66 downwards before it, until the discontinuous annular bottom surface 160 of the cap retainer 150 reaches the level of the hemisphere plane 65 of the bi-spheric shank head 60 and the collet fingers 164 are at their point of maximum expansion.

Figure 62:
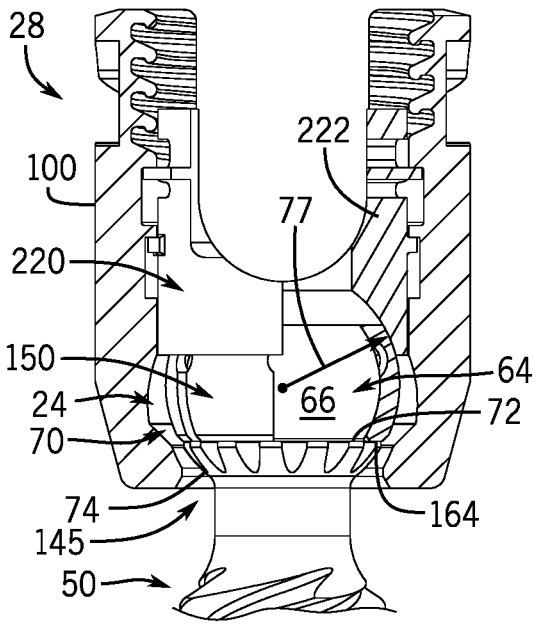
FIG. 62 is a partially cut-away front view of the multiplanar IL receiver sub-assembly continuing to move downward and the bi-spheric shank head continuing to drive upward until the bi-spheric shank head is completely captured by the cap retainer.

With reference to FIG. 62, the IL receiver sub-assembly 28 continues to move downward (or the bone anchor moves upward) as the upper partial spherical portion 64 of the bi-spheric shank head 60 becomes fully captured by the cap retainer 150 as it now contracts inward to close around the upper spherical surface 66. During this motion the discontinuous annular bottom surface 160 continues to push downward toward the lower ledge 70 as the lower partial spherical portion 74 now moves upward into and through the bottom opening 145 of the receiver 100, until the discontinuous annular bottom surface 160 engages the upward-facing planar surface 72 of the lower ledge 70 simultaneously with the capture of the upper partial spherical portion 64 by the cap retainer 150 to form the single diameter, articulating multiplanar shank head sub-assembly 24 having the major diameter 77 that is greater than the diameter of the bottom opening 145 of the receiver 100, thereby preventing the bottom loaded shank 50 from exiting the receiver 100 back out through the same bottom opening 145 through which it was initially loaded.

Figure 63:
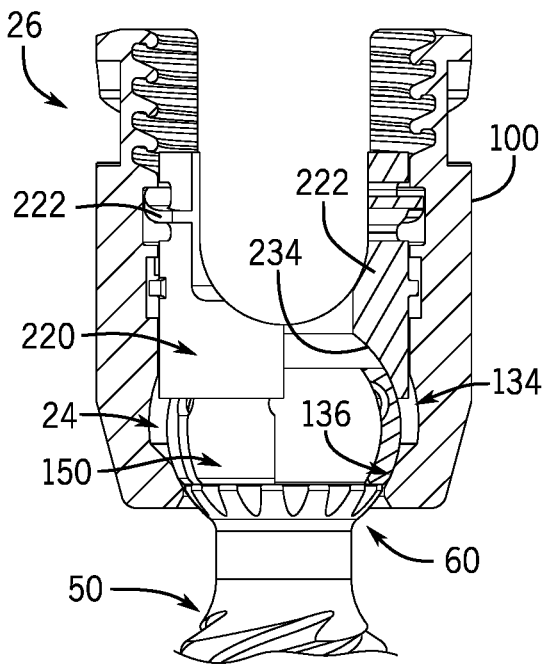
FIG. 63 is a partially cut-away front view of the multiplanar IL receiver sub-assembly with the uploading force being released and IL pressure insert being automatically downwardly deployed to push the multiplanar shank head sub-assembly back downward against the seating surface of the receiver to establish the initial configuration of the multiplanar IL bone anchor assembly in a pre-lock friction fit.

With reference to FIG. 63, once the axially-directed forces used to upload the shank 50 into the IL receiver sub-assembly 28 are released, the compressive load on the resilient upper flanges 222 of the IL pressure insert 220 can operate to automatically push the IL pressure insert 220 and the multiplanar shank head sub-assembly 24 downwardly until the cap retainer 150 (and the bi-spheric shank head 60) are re-secured against the spherical seating surface 136 of the receiver cavity with the frictional engagement, or pre-lock friction fit, without any further manipulation or deployment of the IL pressure insert 220 with tooling. As discussed above, the non-floppy friction fit at the interface at the major diameter 77 between the concave bottom surface 234 of the IL pressure insert 220, the discontinuous outer spherical surface 156 of the cap retainer 150, and the spherical seating surface 136 of the receiver 100 that will maintain the receiver 100 in position relative to the bone anchor or shank 50 unless moved by an applied force. The coupling of the bi-spheric shank head 60 of the bone anchor or shank 50 with the IL receiver sub-assembly 28 can complete the formation of the multiplanar IL bone anchor assembly 26 in its initial configuration, one in which the multiplanar IL bone anchor assembly 26 is ready to be implanted into the vertebrae of a patient or to receive the elongate rod and the closure.

Figure 64:
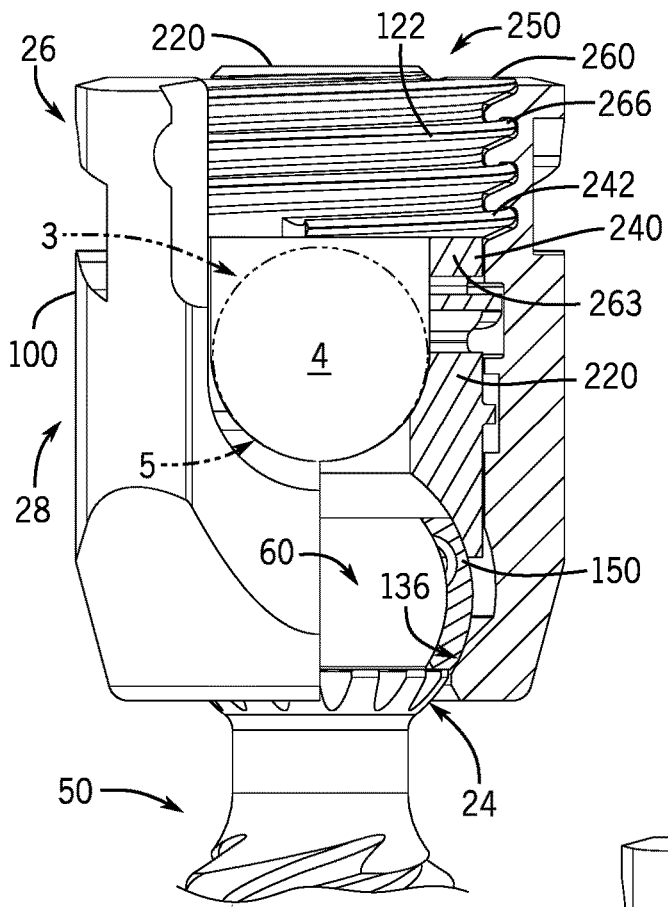
FIG. 64 is a partially cut-away front view of the multiplanar IL bone anchor assembly fully assembled with the elongate rod and with the outer ring of the two-piece closure engaging the upper surfaces of the upright arms of the IL pressure insert in the locked configuration.

Illustrated in FIGS. 64-65 is the multiplanar IL bone anchor assembly 26 as fully assembled and locked with the elongate rod 4 and the two-piece closure 250, and which final assembly can differ from the final assembly of the non-IL, single-piece closure embodiment of the multiplanar bone anchor assembly described above. For instance, after a desired alignment of the rod channel of the receiver 100 has been achieved via manipulation of the multiplanar IL receiver sub-assembly 28 relative to the multiplanar shank head sub-assembly 24, with the axially-biased IL pressure insert 220 providing a pre-lock friction fit (as shown in FIG. 63), the elongate rod 4 can be installed (i.e. reduced) into the rod channel until the lowermost or underside surface 5 of the elongate rod 4 approaches the upward-facing rod seating surface 226 of the IL pressure insert 220. The pre-assembled two-piece closure 250 can then be installed into the upper portion of the central bore 120 of the receiver (optionally using breakoff extensions), in which the continuous outer guide and advancement structure 266 of the outer ring 260 rotatably engages the discontinuous guide and advancement structure 122 formed into the interior faces of the upright arms of the receiver 100 (and the interior surfaces of the breakoff extensions, if present). The two-piece closure 250 can be threaded downwardly until the bottom surface 263 of the outer ring 260 engages and presses against the top surfaces 242 of the crossover structures 240, so as to directly drive the IP pressure insert 220 and the multiplanar shank head sub-assembly 24 downward into the spherical seating surface 136 of the receiver 100, as shown in FIG. 64. This can serve to establish an initial and independent lock of the position of the IL receiver sub-assembly 28 to the bi-spheric shank head 60, in which the IL receiver sub-assembly 28 can no longer pivot or rotate relative to the shank or bone anchor 50.

The center screw 270 of the closure 250 can then screwed downward relative to the outer ring 260 to position the bottom surface 273 of the center screw 270 against the upper surface 5 the elongate rod 4. Continued rotation and torquing of the center screw 270 can then drive the elongate rod 4 downward until the lowermost or underside surface 5 of the elongate rod 4 become fully engaged with and locked against the upward-facing rod seating surface 226 of the IL pressure insert 220, as shown in FIG. 65, to achieve a final locking of the rod 4 to the multiplanar IL bone anchor assembly 26.

Monoplanar Bone Anchor Assembly

Figure 66:
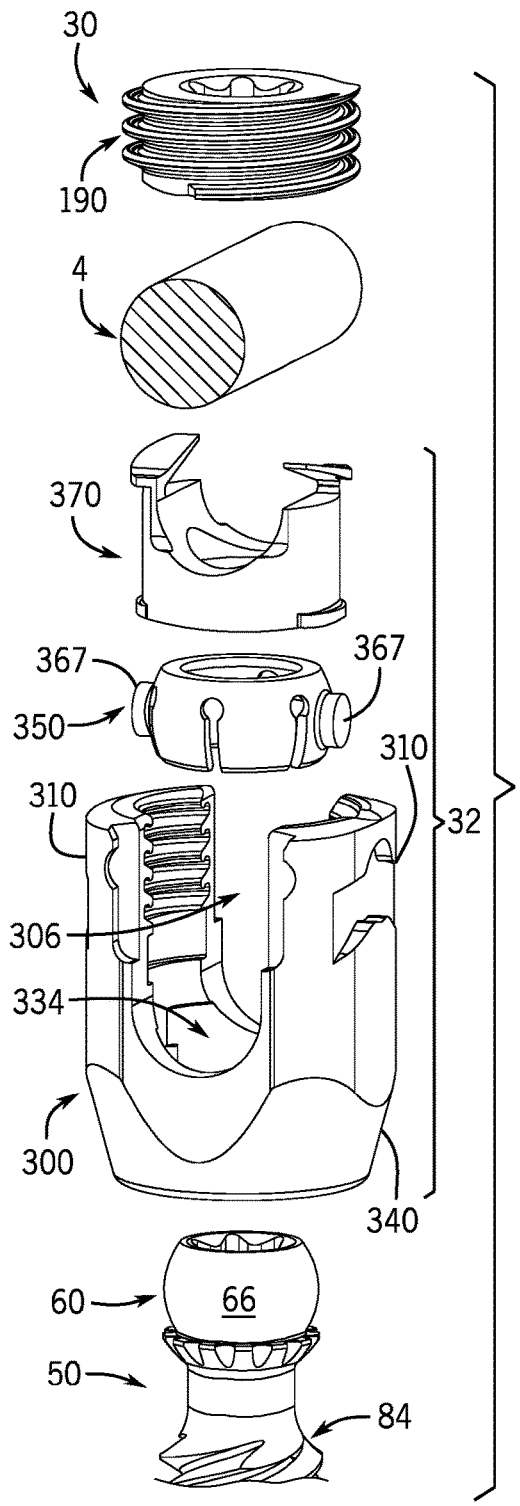
FIG. 66 is an exploded perspective view of a monoplanar embodiment of a bone anchor assembly, in accordance with the representative embodiment of the multi-component spinal fixation system shown in FIG. 1.

Referring now to FIG. 66, illustrated therein is an exploded perspective view of one representative embodiment of the monoplanar bone anchor assembly 30 illustrated in FIG. 1(d) that is configured, as noted above, to limit the pivotal motion of the bone anchor 50 relative to the receiver sub-assembly 32 (or vice versa) to a single plane while still providing for a 360-degree range of rotation around the longitudinal axis 51 of the bone anchor 50. The monoplanar bone anchor assembly 30 can include the same bone anchor or shank 50 described above, having the bi-spheric shank head 60 and the anchor portion 84 opposite the bi-spheric shank head 60 for securement or attachment to the bone of a patient. Similar to the multiplanar bone anchor assemblies discussed above, the monoplanar bone anchor assembly 30 can also include a monoplanar receiver 300 that can be initially pivotably secured to the bi-spheric shank head 60 with a number of separate internal components that have been pre-assembled into the internal cavity 334 and the rod channel 306 of the receiver 300 to form the monoplanar receiver sub-assembly 32. These internal components can include, but are not limited to, a pivoting or articulating monoplanar cap retainer 350 and a monoplanar pressure insert 370. In one aspect the monoplanar pressure insert 370 can also be a resiliently axially biasing insert, as described with reference to the multiplanar embodiment above. After the elongate rod 4 has been positioned within the lower portion of the rod channel 306, the same single-piece closure 190 (or another appropriate type of closure) can be threadably or otherwise secured into the upper portion of the rod channel 306 to apply pressure to an upper surface 3 of the elongate rod 4, thereby locking both the elongate rod 4 and the monoplanar bone anchor assembly 30 into a final locked position.

The primary difference between the multiplanar bone anchor assemblies previously described and the monoplanar bone anchor assembly 30 of FIG. 66 can be the replacement of the multiplanar cap retainer with the monoplanar cap retainer 350 that further includes circular protrusions or pegs 368 that project outwardly from opposite sides of the discontinuous outer spherical surface 356. As shown in the drawing figures, in one aspect the opposite circular pegs 368 are generally configured to be positioned upon an upward-facing annular track or bearing surface 332 formed in the internal cavity 334 of the monoplanar receiver 300 just above the seating surface, so that the while the pivotal motion of the cap retainer 350 relative to the receiver 100 is limited to a single plane defined by a pivot axis extending between the opposite circular pegs, the pivot plane itself is able to rotate around the vertical centerline axis of the monoplanar receiver 300 with the sliding of the circular pegs 368 along the annular bearing surface.

It is foreseen that in other embodiments of the monoplanar receiver sub-assembly, the upward facing bearing surface can be removed and the opposite circular pegs of the monoplanar cap retainer can instead be positioned into opposed vertical side pockets that are more deeply formed into the sidewalls of the internal cavity above the seating surface (not shown), in which case the single pivot plane is not rotatable relative to the monoplanar receiver but is limited to the single orientation defined by the vertical side pockets. In this case the monoplanar receiver sub-assembly may nevertheless be rotatable relative to the bi-spheric shank head by applying enough torque to overcome a frictional engagement at the interface of the minor diameter between the discontinuous inner spherical surface of the monoplanar cap retainer 350 and the upper spherical surface 66 of the bi-spheric shank head 60, as described in more detail below.

It will be appreciated that both the monoplanar receiver 300 and the monoplanar pressure insert 372 can be configured differently in order to better interact with the circular pegs 368 of the monoplanar cap retainer 350 shown in FIG. 66. The remainder of the components forming the monoplanar bone anchor assembly 30, such as the bi-spheric shank head 60, the elongate rod 4, and the closure 190, can be the same as or substantially similar to those already described, so as to provide the component-type modularity for the modular spinal fixation system discussed above with all its attendant features and benefits.

Figure 67:
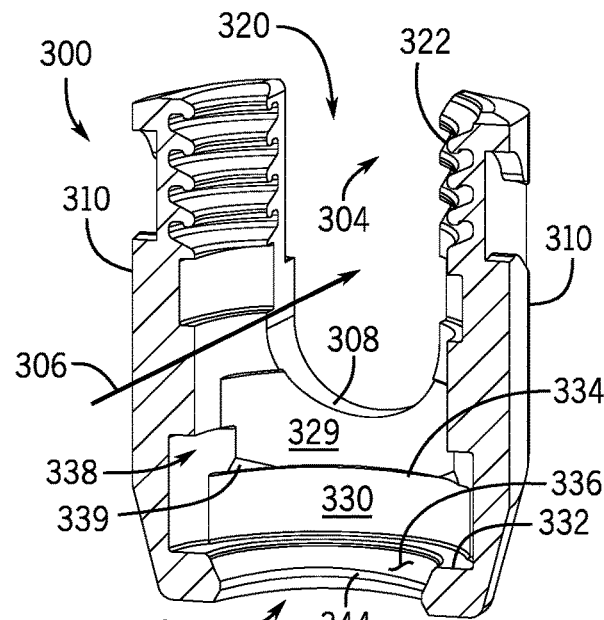
FIG. 67 is a cross-sectional perspective view of the receiver of the monoplanar bone anchor assembly of FIG. 66.
Figure 68:
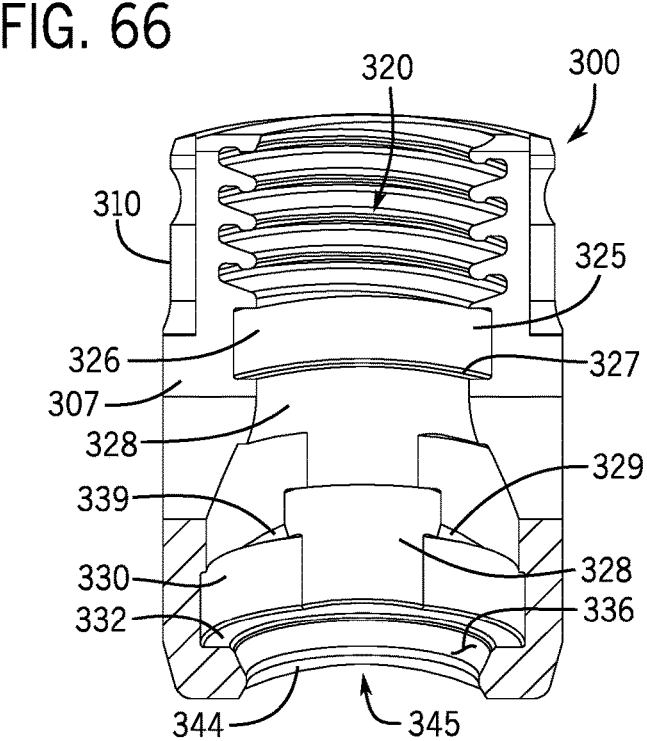
FIG. 68 is another cross-sectional perspective view of the receiver of FIG. 67.
Figure 69:
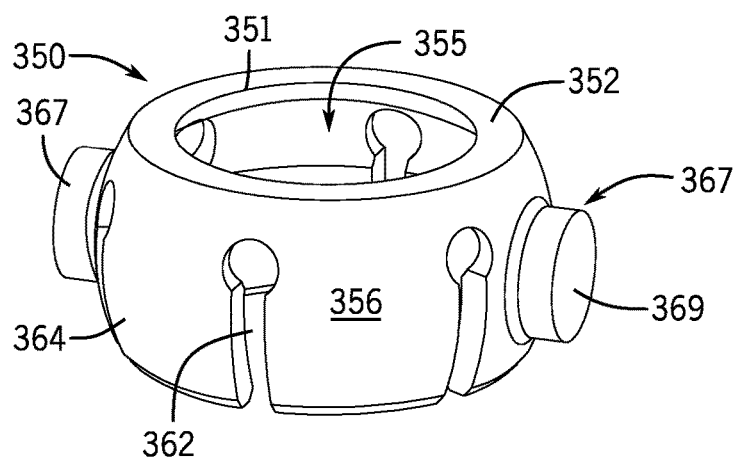
FIG. 69 is a perspective view of the cap retainer of the monoplanar bone anchor assembly of FIG. 66.
Figure 70:
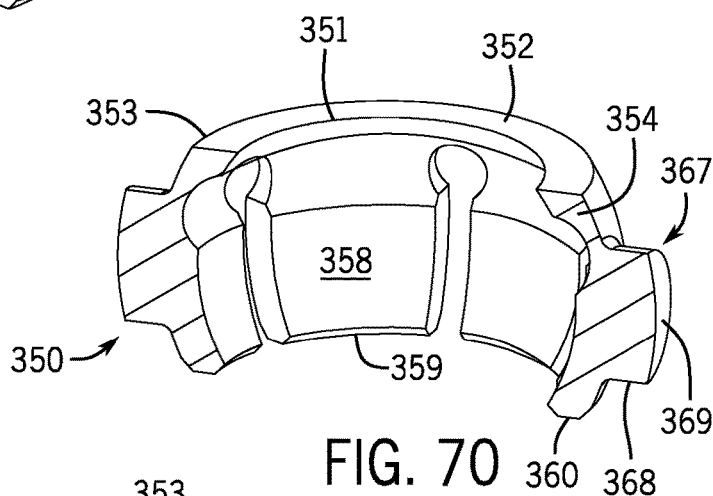
FIG. 70 is a cross-sectional perspective view of the cap retainer of FIG. 69.
Figure 71:
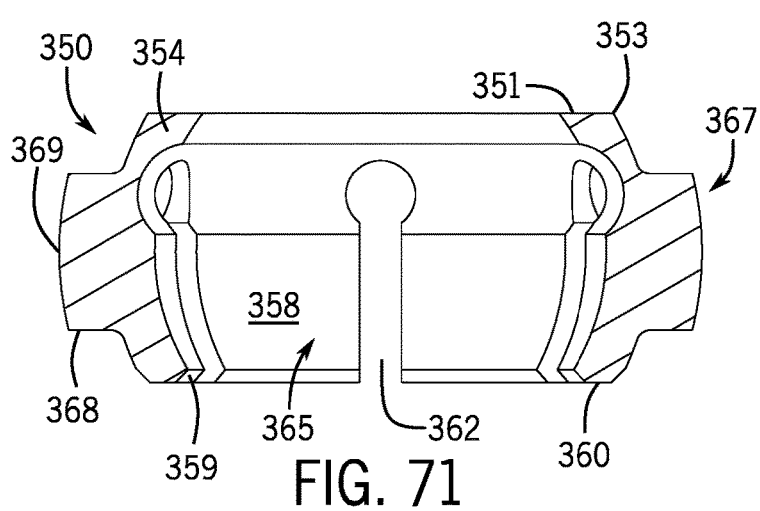
FIG. 71 is a cross-sectional side view of the cap retainer of FIG. 69.
Figure 72:
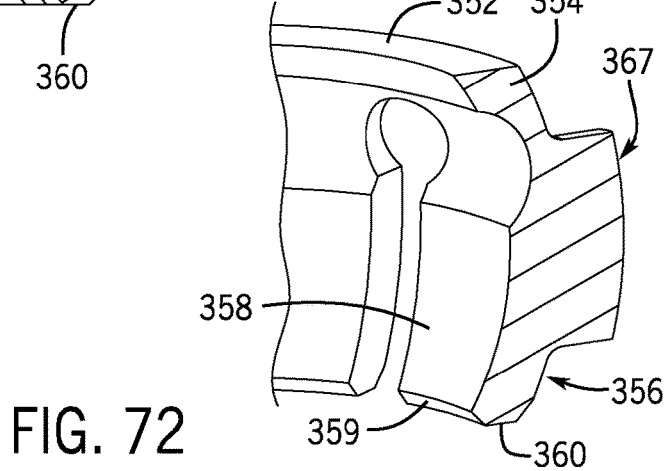
FIG. 72 is a close-up cross-sectional perspective view of a portion of the cap retainer of FIG. 69.
Figure 73:
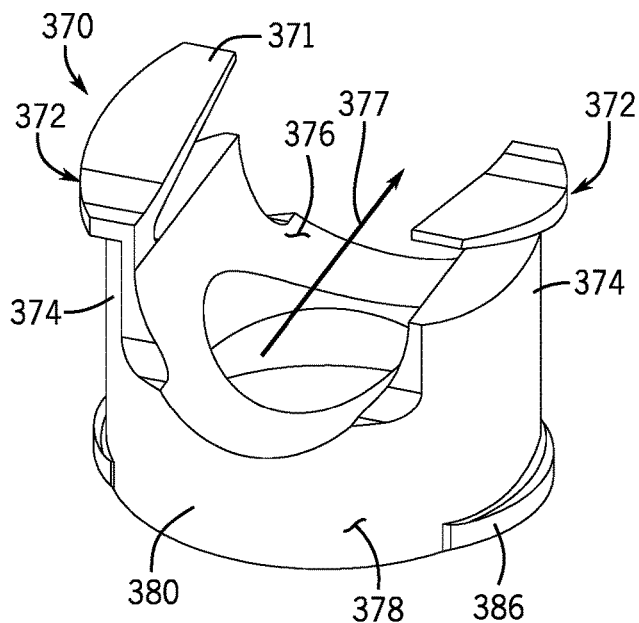
FIG. 73 is a top perspective view of the pressure insert of the monoplanar bone anchor assembly of FIG. 66.
Figure 74:
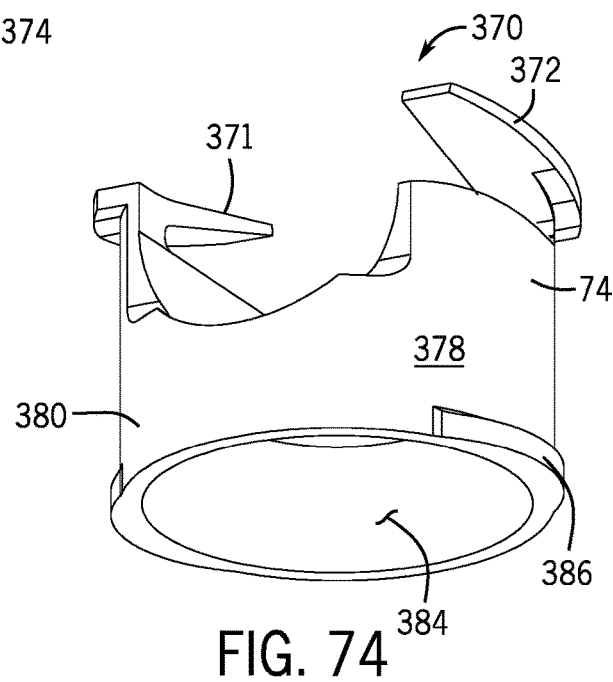
FIG. 74 is a bottom perspective view of the pressure insert of FIG. 73.
Figure 75:
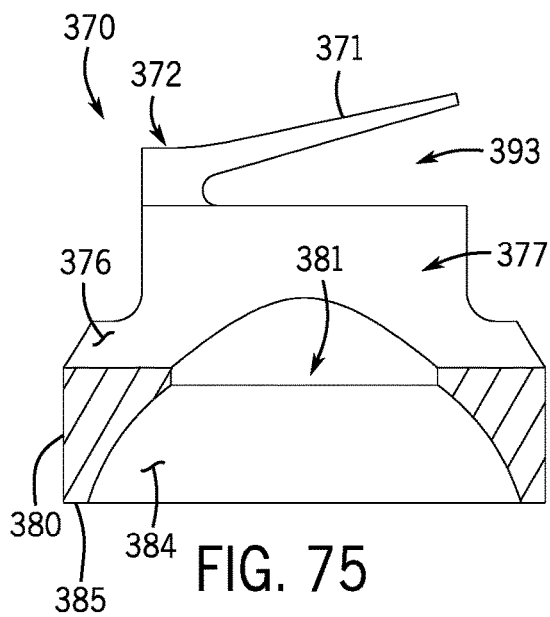
FIG. 75 is a cross-sectional side view of the pressure insert of FIG. 73.
Figure 76:
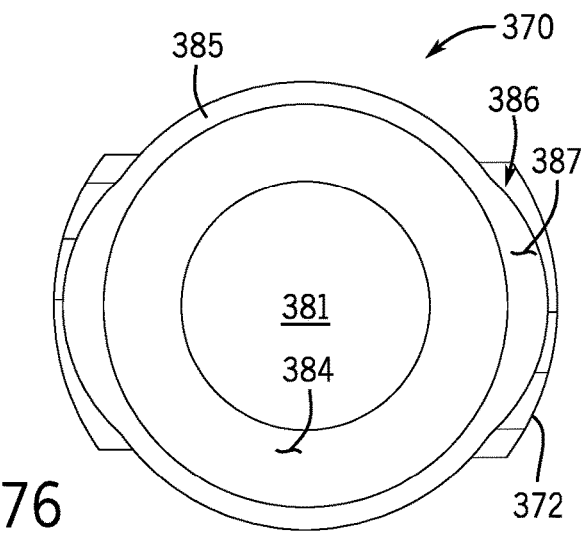
FIG. 76 is a bottom view of the pressure insert of FIG. 73.
Figure 77:
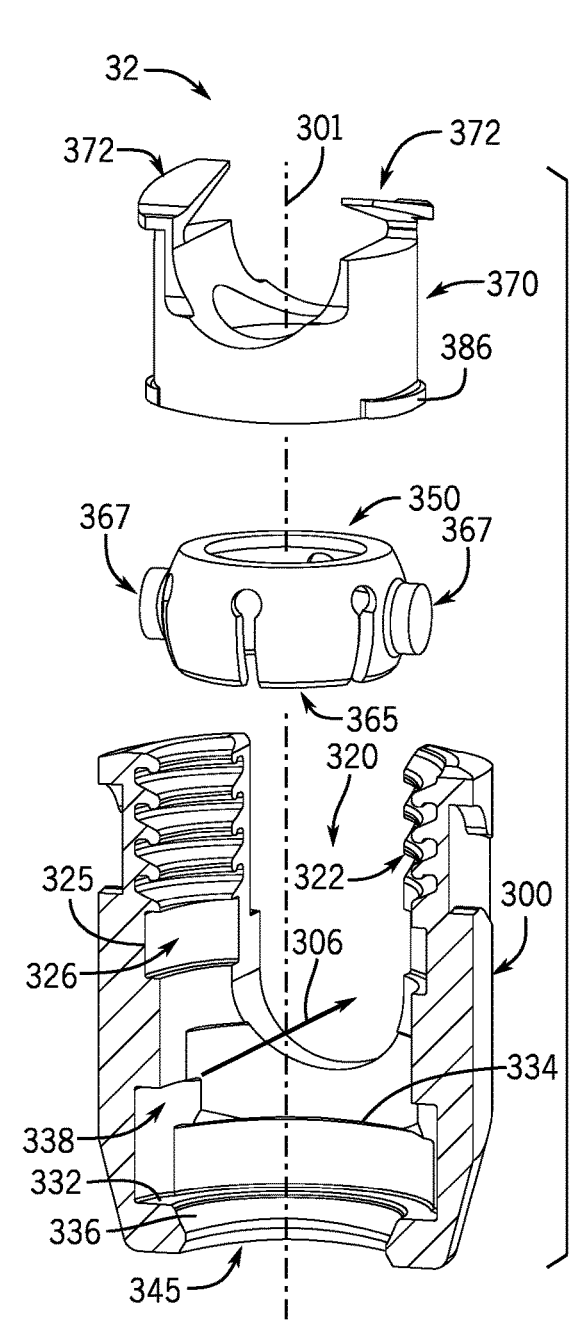
FIG. 77 is an exploded partially cut-away front perspective view of the components of the monoplanar receiver sub-assembly of FIG. 66 prior to their pre-assembly into a shipping configuration.

For example, the monoplanar receiver 300 illustrated in FIGS. 67-68 can include many of the same features of the multiplanar receiver described above, such as the overall shape and exterior features of the base 340 and the upright arms 310, the upper portions of the channel 306 including the opposed vertical planar end surfaces 307 and the discontinuous guide and advancement structure 322, and the lower portions of the central bore 320 including the partially spherically-shaped seating surface 336 and the lowermost cylindrical surface 344 that can define the bottom opening 345 of the receiver 300. However, a number of notable changes can be made in the internal cavity portions of the central bore 230 between the discontinuous inner recess 326 and the spherical seating surface 326. In particular, an upper cylindrical surface 328 formed into the interior faces 304 of the upright arms 310 can extend downward from the upward-facing lower arcuate surface 127 that delineates the lower end of the discontinuous inner recess 326. Opposed center portions of the upper cylindrical surface 328 can extend downward toward the internal cavity 334 to the upper end of opposed, arc-shaped vertical side pockets 338 that are somewhat larger than the opposed vertical side pockets of the multiplanar receiver embodiment. The vertical side pockets 338 of the monoplanar receiver 300 can, in turn, extend downward from the upper cylindrical surface 328 to the upward-facing annular track or bearing surface 332 that is immediately above the partially spherical seating surface 336.

Opposite curvate sidewall surfaces 329, centered below the saddle surfaces 308 that define the lower portions of the channel 106, can extend circumferentially around the upper portions of the interior cavity 334 to intersect with both the upper cylindrical surfaces 328 and upper portions of the vertical side pockets 338. In one aspect the curvate sidewall surfaces 329 can be slightly ramped or increasingly-inwardly-sloped as extending from the widest central location below the saddle surfaces 308 toward the vertical side pockets 338, the reasons for which being similar to the ramped or increasingly-inwardly-sloped surfaces of the horizontal access recesses in the multiplanar receiver embodiment described above.

Moving downward, a lower cylindrical recess 330 can extend across the lower portions of the internal cavity 334 below the curvate sidewall surfaces 329, between the opposed vertical side pockets 338, and immediately above the upward-facing bearing surface 332. As described in more detail below, the lower cylindrical recess 330 and the bearing surface 332 can be configured to accommodate and slidably support the circular pegs 368 of the monoplanar cap retainer 350, so that the monoplanar cap retainer 350 can be continuously rotated around the circumference of the internal cavity 334. In one aspect small, triangular transition surfaces 339 can also be formed at the intersections of the curvate sidewall surfaces 329, the lower cylindrical recess 330, and the vertical side pockets 338.

With reference to FIGS. 69-72, the monoplanar cap retainer 350 can also include many of the same features of the multiplanar embodiment of cap retainer previously described, such as the solid or continuous upper ring portion 354 having an annular planar upper surface 352 with a continuous circular inner edge 351 that defines the central upper opening 355, a discontinuous outer spherical surface 356 extending downward from the continuous circular outer edge 353 toward a discontinuous annular bottom surface 360, a discontinuous inner spherical surface 358 that extends downward from the circular inner edge 351, and a plurality of slots 362 extending through the thickness of the lower portions of the cap retainer 350 to form the collet fingers 364 having inner beveled edge surfaces 359 that define the expandable central lower opening 365 of the cap retainer 350. As described above, however, one difference can be the addition of the opposite circular protrusions or pegs 367 projecting outwardly from the discontinuous outer spherical surfaces 356 on two opposite collet fingers 364. In one aspect each of the opposite circular pegs 367 can include a cylindrical base portion 368 located inwardly of a rounded outer end surface 369, with the cylindrical base portion 368 being configured to ride on the annular bearing surface 332 of the internal cavity 334 of the monoplanar receiver 300 described above (FIGS. 67-68), and for engagement by downward facing surfaces of the monoplanar pressure insert, as described below. Again, as noted above, in one alternative embodiment the monoplanar cap retainer can also be configured with a through-slot or gap for uploading through the bottom opening.

With reference to FIGS. 69-72, the monoplanar pressure insert 370 can also include many of the same features of the multiplanar embodiment of pressure insert previously described, such as the lower base portion 380 with a pair of insert arms 374, the upper flanges 372 projecting radially outward from a cylindrical outer surface that 378 so as to extend into the discontinuous recess 326 formed into the central bore 320 of the multiplanar receiver 300 (FIGS. 67-68), the upward-facing rod seating surface 376 extending between the insert arms 374 to define an insert channel 377, the spherical, downwardly-opening concave lower surface 384 extending upward and inward from an annular planar bottom edge surface 385, and a central tool-receiving aperture 381 defined by an inner cylindrical surface 282. One notable difference can be that the opposite outwardly-projecting indexing nubs 386 or protuberances that define the indexing structure of the pressure insert 370 can be moved down to the annular bottom edge surface 385 of the base portion 380 and can be lengthened circumferentially along the lower edge to better correspond with the wider side pockets 338 formed into the internal cavity 334 of the receiver 300. The indexing nubs 386 can have circumferentially elongate planar bottom surfaces 387 that in one aspect can be flush with or extensions of the annular bottom edge surface 385 of the base 380.

Figure 78:
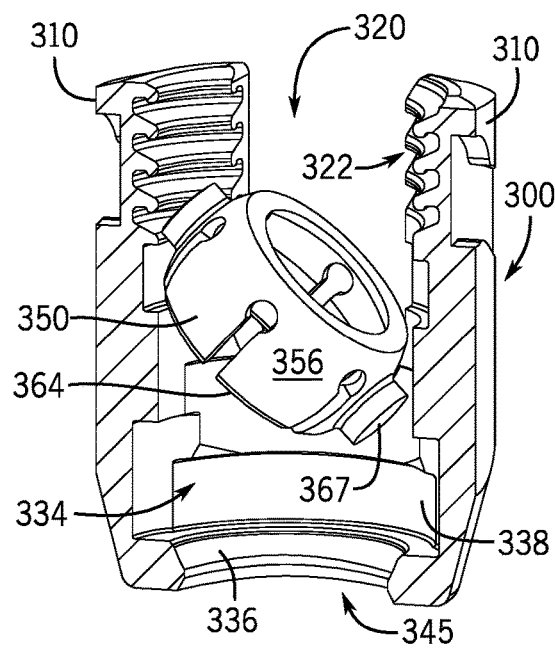
FIG. 78 is a partially cut-away front perspective view of the monoplanar receiver sub-assembly receiver of FIG. 77 with the monoplanar cap retainer being downloaded through the open channel of the receiver.
Figure 79:
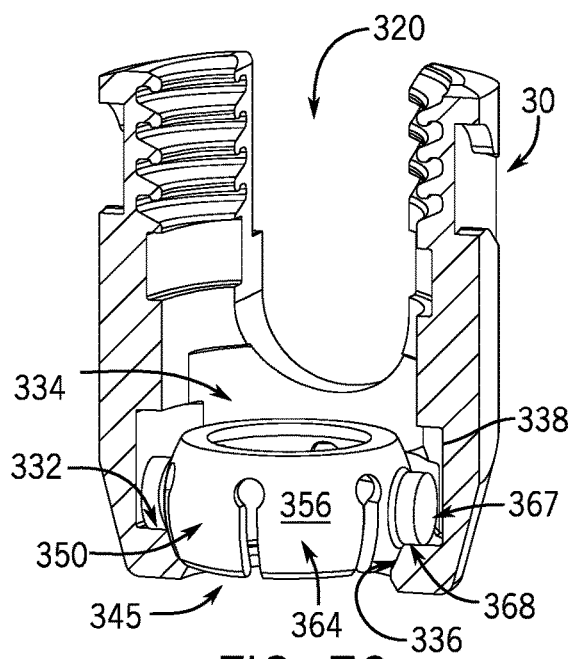
FIG. 79 is a partially cut-away front perspective view of the monoplanar receiver sub-assembly receiver of FIG. 77 with the seated monoplanar cap retainer contacting the spherical seating surface of the receiver.

FIGS. 77 and 78-83 illustrate the pre-assembly of the monoplanar versions of the receiver 300, the cap retainer 350, and the pressure insert 370 together to form the monoplanar receiver sub-assembly 32 in a self-biased shipping state configuration, which method of assembly can be similar to that described above with respect to the multiplanar embodiments but with a few notable differences. In particular, as shown in FIG. 78, the monoplanar cap retainer 350 may require downloading into the internal cavity 334 of the receiver 300 in an angled orientation so that the opposite pegs 367 can fit downward through the central bore 320, between the guide and advancement structure 322 formed into the interior faces of the upright arms 310, and generally in alignment with the vertical side pockets 338. The downloading of the cap retainer 350 into the internal cavity 334 can continue until the lower portions of the discontinuous outer spherical surface 356, specifically the outer surfaces of the collet fingers 364, engage with the spherical seating surface 336 at the lower end of the internal cavity 334 adjacent the bottom opening 345. In this position the cylindrical base portions 368 of the opposite circular pegs 367 can also be positioned on the annular bearing surface 332 of the internal cavity, and the circular pegs 367 themselves can be aligned with the vertical side pockets 338, as shown in FIG. 79.

Figure 80:
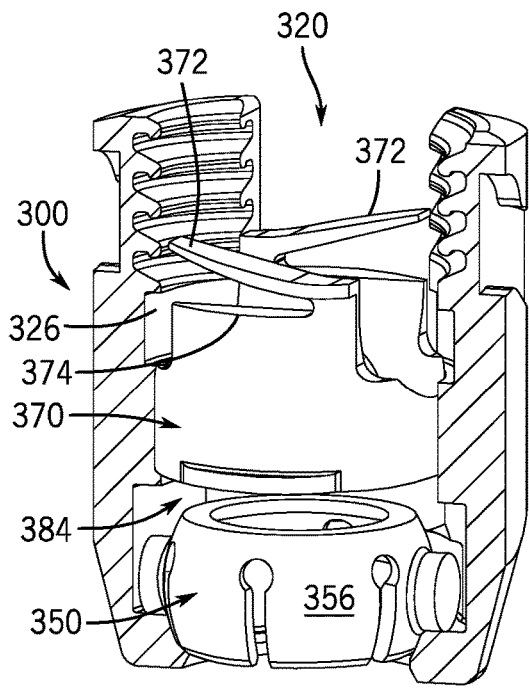
FIG. 80 is a partially cut-away front perspective view of the monoplanar receiver sub-assembly receiver of FIG. 77, together with the seated monoplanar cap retainer and with the monoplanar pressure insert being downloaded through the open channel of the receiver.
Figure 81:
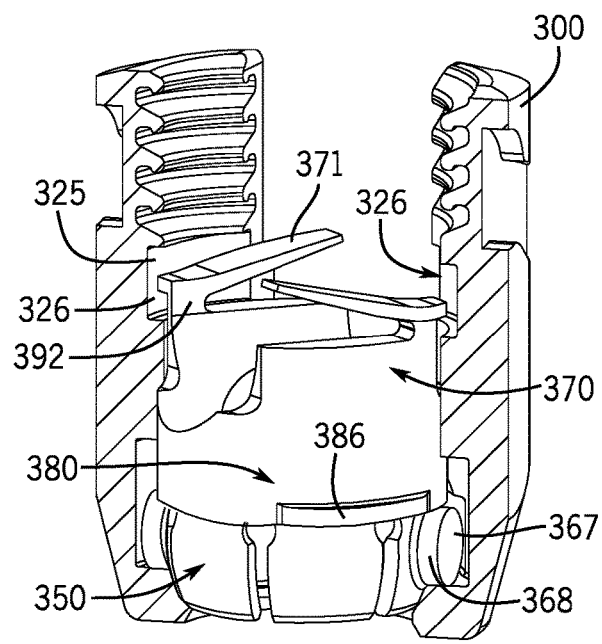
FIG. 81 is a partially cut-away front perspective view of the monoplanar receiver sub-assembly receiver of FIG. 77, together with the seated monoplanar cap retainer and the downloaded and partially rotated monoplanar pressure insert.

After the cap retainer 350 is seated on the spherical seating surface 336 of the receiver 300, the pressure insert 370 may then be top-loaded or down-loaded into the central bore 320 and installed into its the shipping state position above the cap retainer 350. This can be achieved by positioning the pressure insert 370 above the central bore 320 with the insert arms 374 and their radially-outwardly projecting upper flanges 372 being aligned with the open channel, and then downloading the pressure insert 370 into the central bore 320, as shown in FIG. 80. The pressure insert 370 can move downward within the central bore 320 until the concave lower surface 384 of the pressure insert 370 lightly engages the upper portion of the discontinuous outer spherical surface 356 of the cap retainer 350 and the upper flanges 372 reach the level of the discontinuous inner recess 326 formed into the central bore 320. In the initial downloaded pre-rotation position, the level of the leading edges of the upwardly-angled top surfaces 371 of the resilient upper flanges 372 can be proximate a mid-portion of the discontinuous inner recess 326, while the level of the trailing edges of the top surfaces 371 can extend above the level of the downward-facing upper arcuate surfaces 325 of the discontinuous recess 326. With reference to FIG. 81, after reaching the initial downloaded pre-rotation position, the pressure insert 370 may then be rotated around its longitudinal axis (which is co-axial with the vertical centerline axis of the receiver 300) so that the leading edges of the upwardly-angled top surfaces 371 of the resilient upper flanges 372 begin to enter into the discontinuous inner recess 126 of the upright arms 110 and the opposite indexing nubs 386 projecting outwardly from the base 380 of the insert 370 begin to slide along the opposed curvate sidewall surfaces 329 of the internal cavity 334.

Figure 82:
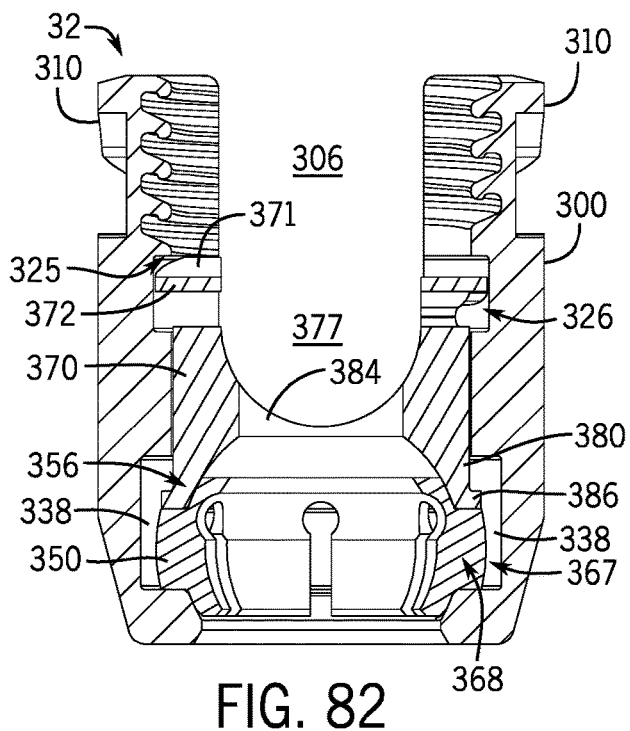
FIG. 82 is a partially cut-away front view of the monoplanar receiver sub-assembly receiver of FIG. 77, together with the seated monoplanar cap retainer and the monoplanar pressure insert being fully rotated therein and automatically deployed to form a pre-assembled monoplanar receiver sub-assembly in the shipping state configuration.
Figure 83:
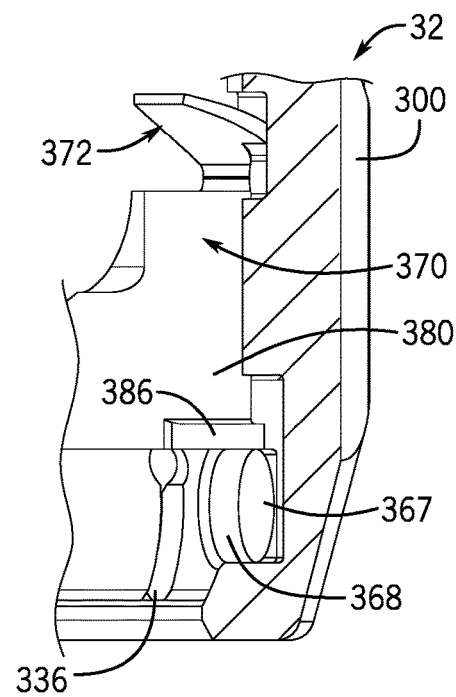
FIG. 83 is a close-up partially cut-away front perspective view of the monoplanar receiver sub-assembly of FIG. 82.

With reference to FIGS. 82-83, continued rotation of the pressure insert 370 can cause the top surfaces 371 of the upper flanges 372 to slidably resiliently engage with the downward-facing upper arcuate surfaces 325 of the discontinuous recess 326. Because the vertical location of the pressure insert 370 within the central bore 320 is fixed by the connection between the concave lower surface 384 and the upper portion of the discontinuous outer spherical surface 356 of the cap retainer 350, this slidable engagement can cause the resilient upper flanges 372 to deflect downward under compression in order to enter the discontinuous recess 326. The rotation of the pressure insert 370 can continue for a full 90 degrees or quarter turn, until the rod channel 377 of the insert 370 becomes aligned with the open channel 306 of the receiver 300, the compressed upper flanges 372 become fully positioned within the discontinuous inner recess 326 of the interior faces of the upright arms 310, and the opposite indexing nubs 386 projecting outwardly from the lower end of the base 380 can completely slide into the opposed vertical side pockets 338 of the central bore 320 and come to rest upon the upper portions of the cylindrical base portions 368 of the opposite circular pegs 367. As with the multiplanar bone anchor assembly described above, the resiliently axially-biased monoplanar pressure insert 370 can provide a friction fit that stabilizes and inhibits motion of the monoplanar cap retainer 350 within the internal cavity 334 to prevent any subsequent movement and misalignment of the cap retainer 350 relative to the 345 bottom opening that would impede the uploading of the bi-spheric shank head of the bi-spherical universal shank during assembly.

The assembly of the separate components into the monoplanar receiver sub-assembly 32, namely the receiver 300, the cap retainer 350, and the pressure insert 370, into the shipping state configuration is now complete. It will be appreciated that the monoplanar receiver sub-assembly 32 is now ready for storage and/or shipping and handling, and for eventual attachment to the bi-spheric shank head of a bone anchor or shank either prior to or during spinal surgery.

The assembly of the monoplanar receiver sub-assembly 32 of FIGS. 82-83 to the bi-spheric shank head 60 of the bone anchor 50 can be substantially similar to the assembly of the multiplanar embodiments discussed above. For example, and with reference to the abbreviated sequence of assembly shown in FIGS. 84-88, the monoplanar receiver sub-assembly 32 can be first positioned above the proximal end 52 of the bone anchor 50, with the bottom opening 345 of the receiver 300 and the central lower opening 365 of the cap retainer 350 being generally aligned with the upper partial spherical portion 64 of the bi-spheric shank head 60, as shown in FIG. 84. The monoplanar receiver sub-assembly 32 is then dropped downward (or the bone anchor 50 is moved upward, depending on the frame of reference of the reader) until the upper spherical surface 66 of the bi-spheric shank head 60 passes upward through the bottom opening 345 of the receiver 300 to engage the inner beveled edge surfaces 359 of the discontinuous annular bottom surface 360 of the cap retainer, as shown in FIG. 85.

With reference to FIG. 86, the monoplanar receiver sub-assembly 32 continues to move downward (or the bone anchor moves upward) as the bi-spheric shank head 60 pushes both the cap retainer 350 and the pressure insert 370 upwards within the internal cavity 334 and the central bore 320 of the receiver 300, respectively, thereby compressing the resilient upper flanges 372 of the pressure insert 370 against the immovable upper arcuate surfaces 325 of the discontinuous inner recess 326. In one aspect the pressure insert 370 can quickly reach its uppermost position within the central bore 320 defined by the upper surfaces of the indexing nubs 386 abutting against the downward-facing upper surfaces of the vertical side pockets 338. At the same time, the central lower opening 365 of the cap retainer 350 can begin to expand as the cap retainer 350 enters the upper expansion portion of the internal cavity 334, thereby allowing the inner beveled edge surfaces 359 of the discontinuous annular bottom surface 360 to scrape downwards across the upper spherical surface 66 of the bi-spheric shank head 60 as it moves upward into the internal cavity 334 of the receiver 300.

With the pressure insert 370 being fixed relative to the receiver 300 and the upper end of the cap retainer 350 being fixed against the concave lower surface 384 of the pressure insert 370, the collet fingers 364 of the cap retainer 350 continue to be expanded within the expansion portion 331 of the internal cavity 334 by the upward movement of the bi-spheric shank head 60 into the receiver. With continued reference to FIG. 86, the expansion of the cap retainer 350 can continue, with the discontinuous annular bottom surface 360 pushing any bone debris and/or soft tissue located on the upper spherical surface 66 downwards before it, until the discontinuous annular bottom surface 360 reaches the hemisphere plane of the bi-spheric shank head 60 and the cap retainer 350 is at its point of maximum expansion. Also visible in the drawing figures, the vertical side pocket 338 of the internal cavity 334 can be size and shaped to provide clearance for the movement of the opposite circular pegs 367 as they twist upwards due to upward and outward movement of the collet fingers from which they extend.

Figure 87:
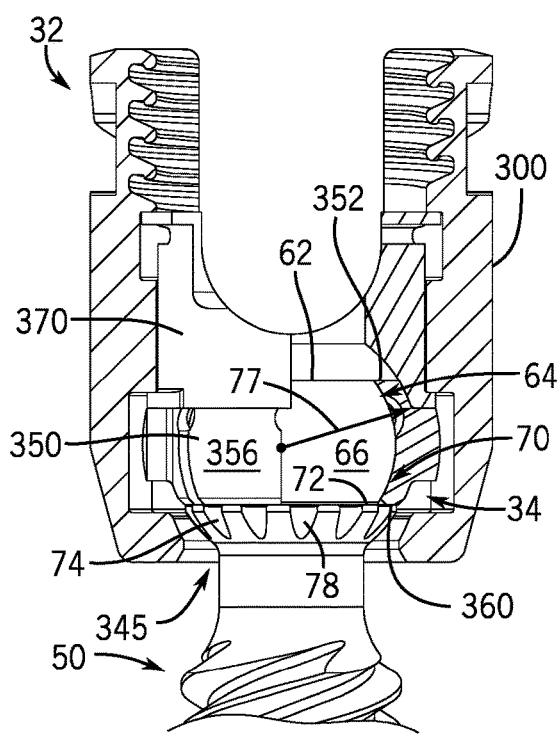
FIG. 87 is a partially cut-away front view of the monoplanar receiver sub-assembly continuing to move downward and the bi-spheric shank head continuing to drive upward until the bi-spheric shank head is completely captured by the cap retainer.

With reference to FIG. 87, the monoplanar receiver sub-assembly 32 continues to move downward (or the bone anchor moves upward) as the upper partial spherical portion 64 of the bi-spheric shank head 60 becomes fully captured by the cap retainer 350 as it contracts to close around the lower half of the upper partial spherical portion 64. During this motion, the discontinuous annular bottom surface 360 of the cap retainer 350 continues to push any bone debris and/or soft tissue downward toward the lower ledge 70 as the lower partial spherical portion 74 now moves upward into and through the bottom opening 345 of the receiver 300. Any bone debris and/or soft tissue that has been removed from the upper spherical surface 66 of the bi-spheric shank head 60 can pass through the plurality of open, vertically aligned flutes 78 that extend downwardly through and below the lower ledge 70 as the discontinuous annular bottom surface 360 engages the upward-facing surface 72 of the lower ledge 70.

The discontinuous inner spherical surface 358 of the cap retainer 350 is now secured around the upper spherical surface 66 of the bi-spheric shank head 60. As with the multiplanar embodiment described above, the annular planar upper surface 352 of the cap retainer 350 can aligned flush with the annular top surface 62 of the bi-spheric shank head 60 while the discontinuous outer spherical surface 356 of the cap retainer 350 can aligned with the lower spherical surface 76 of the lower partial spherical portion 74 so as to create a single diameter, articulating, monoplanar shank head sub-assembly 34 having the major diameter 77 that is greater than the diameter of the bottom opening 345 of the receiver 300.

Figure 88:
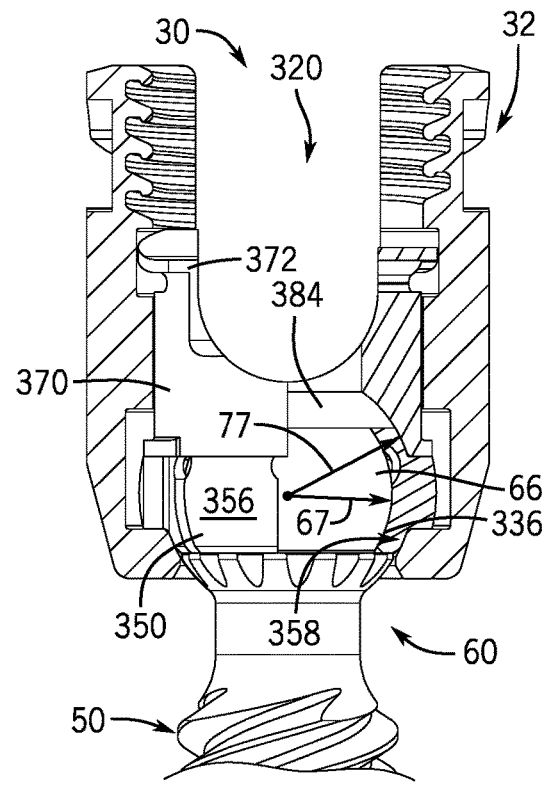
FIG. 88 is a partially cut-away front view of the monoplanar receiver sub-assembly with the uploading force being released and pressure insert being automatically downwardly deployed to push the monoplanar shank head sub-assembly back downward against the seating surface of the receiver to establish the initial configuration of the monoplanar bone anchor assembly in a pre-lock friction fit.

With reference to FIG. 88, the axially-directed forces used to upload the shank 50 to the monoplanar receiver sub-assembly 32 can now be released, which in turn releases the compressive load on the resilient upper flanges 372 of the pressure insert 370 and allows them to automatically push the pressure insert 370 and the monoplanar shank head sub-assembly 34 downwardly until the cap retainer 350 (and the bi-spheric shank head 60) are re-secured against the spherical seating surface 336 with a frictional engagement, or pre-lock friction fit, without any further manipulation or deployment of the pressure insert 370 with tooling. The coupling of the universal bi-spheric shank head 60 of the bone anchor or shank 50 with the monoplanar receiver sub-assembly 32 can complete the formation of the monoplanar bone anchor assembly 30 in its initial configuration, one in which the monoplanar bone anchor assembly 30 is ready to be implanted into the vertebrae of a patient or to receive the elongate rod and the closure.

Figure 89:
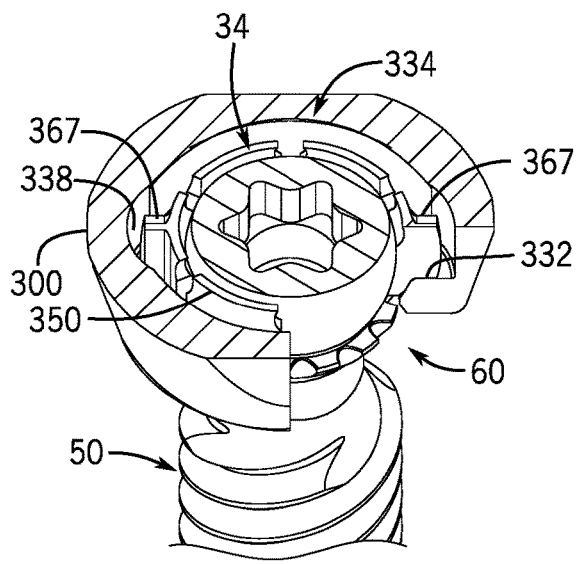
FIG. 89 is a cross-sectional top perspective view of the monoplanar bone anchor assembly, showing the monoplanar cap retainer aligned with the vertical side pockets of the receiver.
Figure 90:
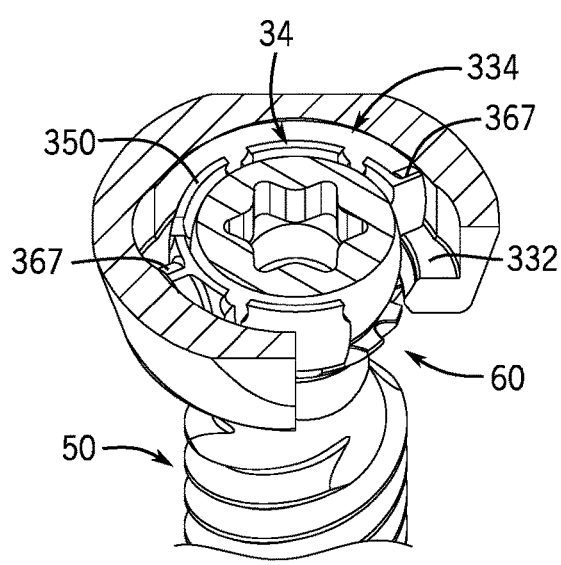
FIG. 90 is another cross-sectional top perspective view of the monoplanar bone anchor assembly, showing the monoplanar cap retainer rotated within the internal cavity with respect to vertical side pockets of the receiver.
Figure 91:
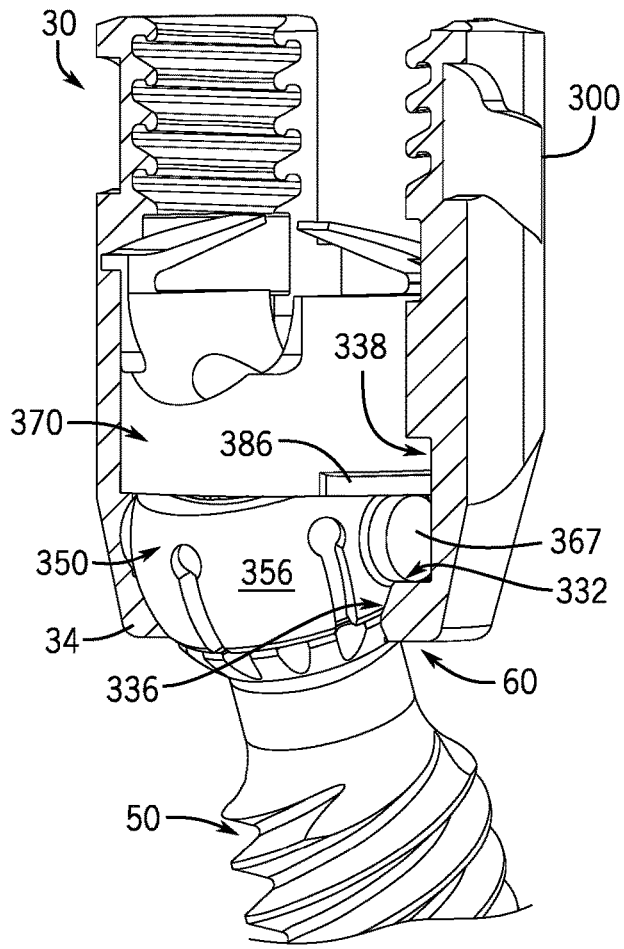
FIG. 91 is a partially cut-away front perspective view of the monoplanar bone anchor assembly, showing the monoplanar cap retainer aligned with the vertical side pockets of the receiver.
Figure 92:
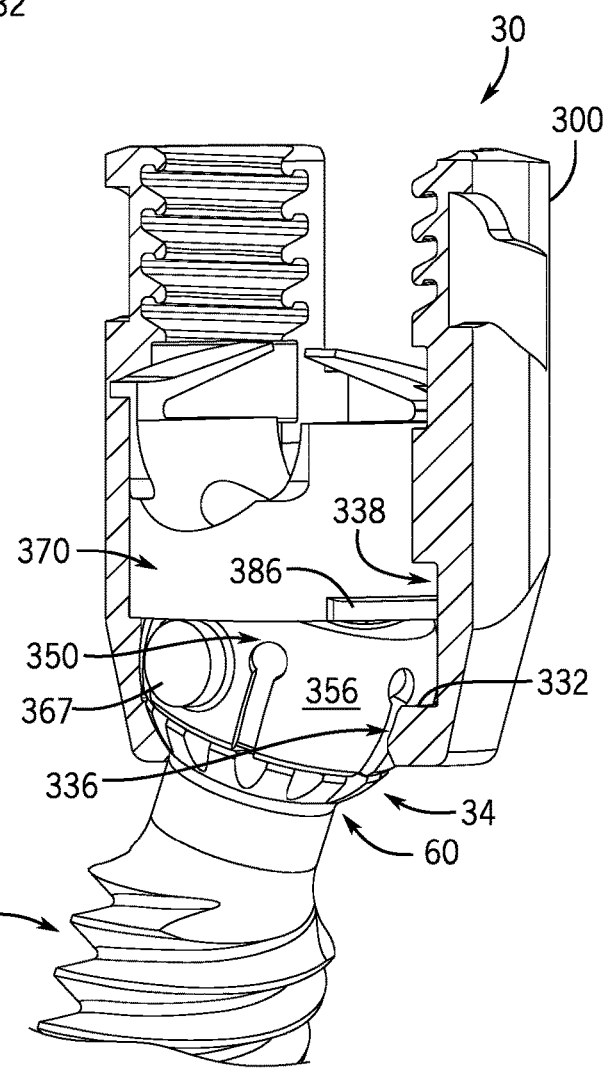
FIG. 92 is another partially cut-away front perspective view of the monoplanar bone anchor assembly, showing the monoplanar cap retainer rotated within the internal cavity with respect to vertical side pockets of the receiver.

With reference to FIGS. 88 and 89-92, it is contemplated that the frictional engagements at the interface at the minor diameter 67 (FIG. 88), between the discontinuous inner spherical surface 358 of the cap retainer 350 and the upper spherical surface 66 of the bi-spheric shank head 60, can be stronger than the frictional engagements at the interface at the major diameter 77, between the discontinuous outer spherical surface 356 of the cap retainer 350, the concave lower surface 384 of the pressure insert 370, and the spherical seating surface 336 of the receiver 300 that may be provided by the axially-biasing pressure insert 370. As such, any rotational forces or moments created between the bi-spheric shank head 60 and the monoplanar receiver sub-assembly 32 can cause the circular pegs 367 of the cap retainer 350 to slide around the annular bearing surface 332 of the internal cavity 334, from the initial orientation in which the circular pegs 367 are aligned with the vertical side pockets 338 (as shown in FIGS. 89 and 91) to orientations in which the monoplanar shank head sub-assembly 34 (i.e. the combined bi-spherical shank and the monoplanar cap retainer) has been rotated relative to the receiver 300 and the circular pegs 367 have been moved to other opposite locations on the annular bearing surface 332 (as shown in FIGS. 90 and 92). This 360-degree range of rotational motion of the monoplanar shank head sub-assembly 34 around the longitudinal axis 51 of the receiver 300, while limiting the pivotal motion of the shank 50 to the single plane extending perpendicular to the pivot axis defined by the circular pegs 367, can be available even as the axially-biasing pressure insert 370 is providing the pre-lock friction fit.

It is foreseen that in one alternative embodiment of the monoplanar receiver 300 described above, the upward-facing annular track or bearing surface can be removed and the opposite circular pegs of the monoplanar cap retainer can instead be positioned into opposed vertical side pockets that are more deeply formed into the sidewalls of the internal cavity. In this embodiment the monoplanar receiver sub-assembly may nevertheless be rotatable relative to the bi-spheric shank head by applying enough torque to overcome the frictional engagement at the minor diameter interface between the discontinuous inner spherical surface of the monoplanar cap retainer and the outer upper spherical surface of the bi-spheric shank head.

As with the multiplanar embodiment described above, it is also foreseen that both the monoplanar receiver and the monoplanar pressure insert can be reconfigured for manual downwardly deployment of the monoplanar pressure insert using tooling after the bi-spheric shank head has been captured by the monoplanar cap retainer, so as to provide the pre-lock friction fit. For example, the monoplanar pressure insert can be provided with the opposite outwardly-projecting flanges that are moved downward from the opposed upper recesses to become engaged within the opposed lower recesses upon deployment of pressure insert with the tooling. In yet another alternative embodiment, both the monoplanar receiver and the monoplanar pressure insert can be reconfigured so that tooling may be used to temporarily hold the monoplanar pressure insert down in a biased or even in a temporarily locked position within the monoplanar receiver sub-assembly, until there is a final locking of the monoplanar bone anchor assembly with the elongate rod and via the closure.

Figure 93:
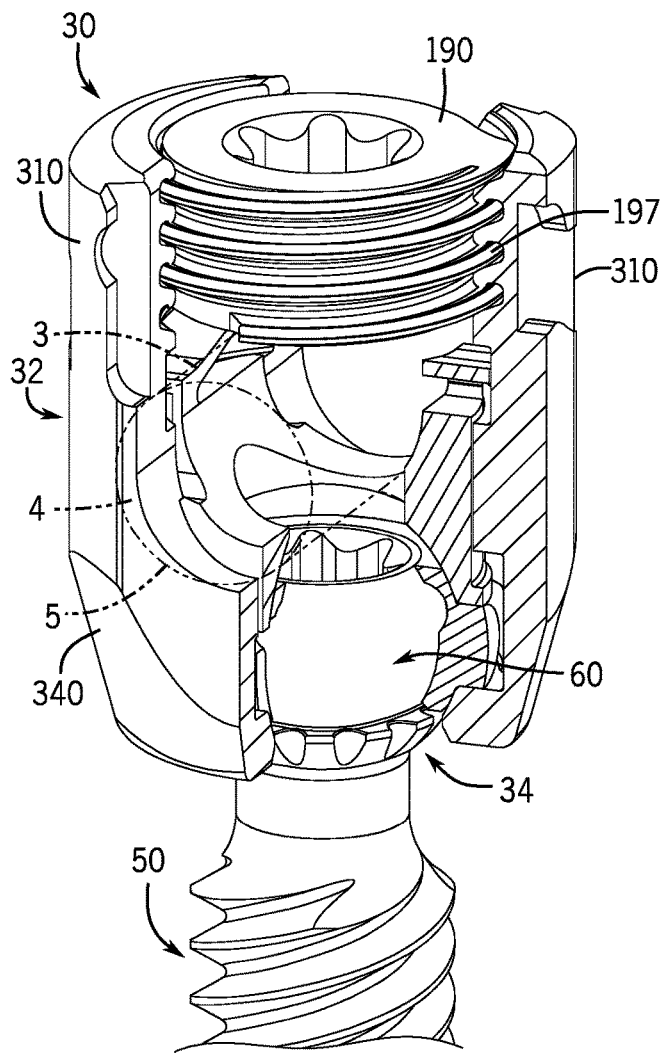
FIG. 93 is a partially cut-away front perspective view of the monoplanar bone anchor assembly, fully assembled with the elongate rod and closure and with the bone anchor in a non-articulated position relative to the receiver.
Figure 94:
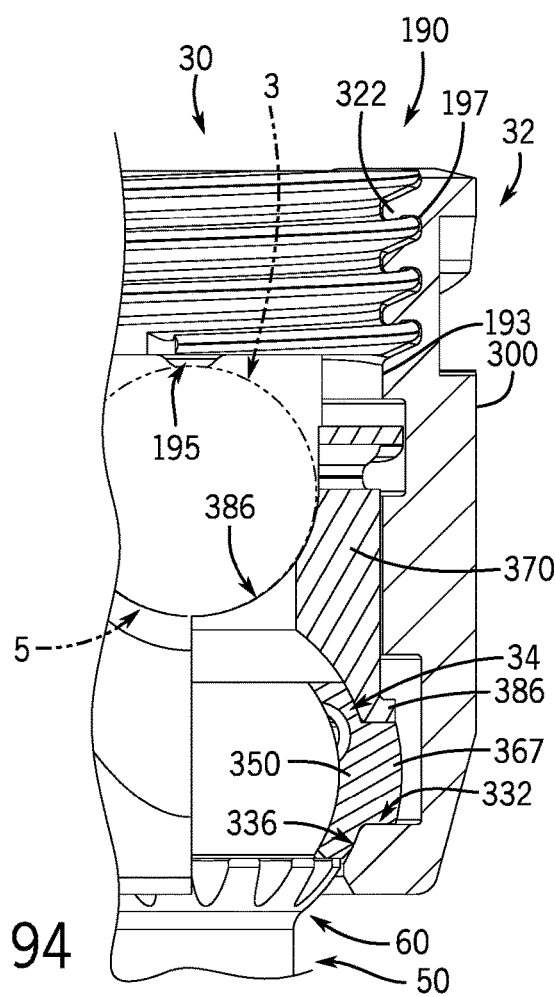
FIG. 94 is a close-up partially cut-away front view of a portion of the fully-assembled monoplanar bone anchor assembly of FIG. 93.

Illustrated in FIGS. 93-94 is the monoplanar bone anchor assembly 30 as fully assembled and locked with the elongate rod 4 and the single-piece closure 190. For instance, after a desired alignment of the rod channel of the receiver 300 has been achieved via manipulation of the monoplanar receiver sub-assembly 32 relative to the shank head 60 or, more accurately, to the monoplanar shank head sub-assembly 34, and with the axially-biased monoplanar insert 370 providing a pre-lock friction fit, the elongate rod 4 can be installed (i.e. reduced) into the rod channel, such as with instruments and/or breakoff extensions on the upright arms 310, until the lowermost or underside surface 5 of the elongate rod 4 approaches the upward-facing rod seating surface 386 of the pressure insert 370. The closure 190 can then be installed into the upper portion of the central bore of the receiver (optionally using breakoff extensions), in which the outer continuous guide and advancement structure 197 of the closure 190 rotatably engages the discontinuous guide and advancement structure 322 formed into the interior faces of the upright arms 310 of the receiver 100 (and the interior surfaces of the breakoff extensions, if present). The closure 190 can be threaded downwardly until the bottom surface 193, or the downwardly-projecting central projection 195 protruding therefrom, engages the upper surface 3 of the elongate rod 4. Further rotation and torquing of the closure 190 can then be used to drive the elongate rod 4 downward onto the pressure insert 370, which in turn further drives the monoplanar shank head sub-assembly 34 downward onto the spherical seating surface 336 and the annular bearing surface 332 of the internal cavity 334 of the receiver 300 to achieve a final locking of the monoplanar bone anchor assembly 30, in which the monoplanar receiver sub-assembly 32 can no longer pivot or rotate relative to the shank or bone anchor 50. It will be appreciated that, in positions of the monoplanar shank head sub-assembly 34 where the circular pegs 367 are generally aligned with the indexing nubs 386, the engagement between the circumferentially elongate planar bottom surfaces of the indexing nubs 386 with the cylindrical base portions 368 of the circular pegs 367 can serve to hold the circular pegs 367 down against the annular bearing surface 332, and thereby restrain the monoplanar cap retainer 350 from lifting or twisting up off of the annular bearing surface 332 under out-of-plane side loading or bending on the shank in the monoplanar bone anchor assembly 30.

Monoaxial Bone Anchor Assembly

Figure 95:
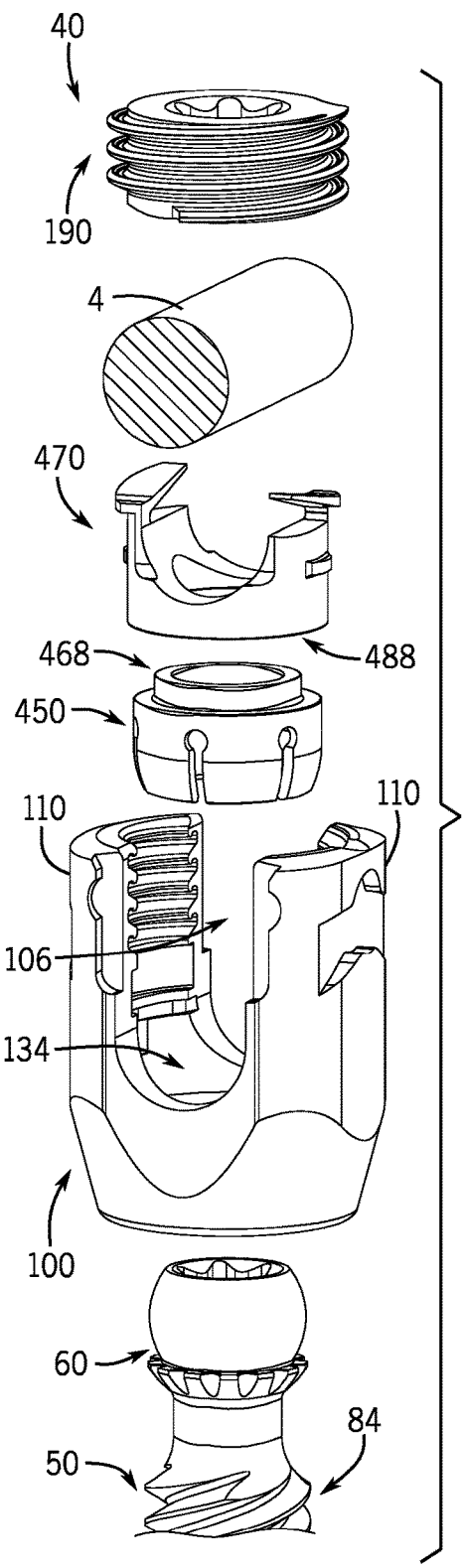
FIG. 95 is an exploded perspective view of a monoaxial embodiment of a bone anchor assembly, in accordance with the representative embodiment of the multi-component spinal fixation system shown in FIG. 1.

Referring now to FIG. 95, illustrated therein is an exploded perspective view of one representative embodiment of the monoaxial or 'non-pivotal but rotatable' bone anchor assembly 40 illustrated in FIG. 1(e) that is configured, as noted above, to substantially eliminate pivotal motion of the bone anchor relative to the receiver sub-assembly (except perhaps for a slight toggle) while still providing for a 360-degree range of rotational motion around the longitudinal axis 51 of the bone anchor 50. The monoaxial bone anchor assembly 40 can include the same bone anchor or shank 50 described above, having a bi-spheric shank head 60 and an anchor portion 84 opposite the bi-spheric shank head 60 for securement or attachment to the bone of a patient. Similar to the multiplanar and monoplanar bone anchor assemblies discussed above, the monoaxial bone anchor assembly 40 can also include a receiver 100 that can be initially non-pivotably secured to the bi-spheric shank head 60 with a number of separate internal components that have been pre-assembled into the central bore 120 and the rod channel 106 to form the monoaxial receiver sub-assembly 42. These internal components can include, but are not limited to, a monoaxial cap retainer 450 and a monoaxial pressure insert 470. In one aspect the monoaxial pressure insert 470 can also be a resiliently axially biasing insert, as described above. After an elongate rod 4 has been positioned within the lower portion of the rod channel 106, the same single-piece closure 190 (or another appropriate type of closure) can be threadably or otherwise secured into an upper portion of the rod channel 106 to apply pressure to an upper surface of the elongate rod 4, thereby locking both the elongate rod 4 and the monoaxial bone anchor assembly 40 into a final locked position.

The primary differences between the multiplanar bone anchor assemblies previously described and the monoaxial bone anchor assembly of FIG. 95 can be the replacement of the pivotal multiplanar cap retainer, having a discontinuous outer spherical surface that extends continuously upward from the discontinuous annular bottom surface, with a non-pivotal monoaxial cap retainer 450 having a discontinuous outer spherical surface toward the bottom opening that transitions upwardly into a partial cylindrical side surface. In addition, the monoaxial cap retainer 450 can include an upper stepped cylindrical structure 468 having a raised inward annular surface surrounded by a lower outward annular surface that extends radially outward to the partial cylindrical side surface.

The monoaxial pressure insert 470 may also be configured differently in order to better interact with the monoaxial cap retainer 450 within the central bore 120 of the receiver 100. For example, the bottom portion of the monoaxial pressure insert 470 can also be modified, with the downwardly-opening concave lower surface being replaced with a lower stepped cylindrical structure 488 that is mateable with the upper stepped cylindrical structure 468 to form a vertically-centered stepped cylindrical joint that allows for relative rotation between the cap retainer 450 and the pressure insert 470 while inhibiting pivoting and lateral motions. The remainder of the components forming the monoplanar bone anchor assembly 40, such as the bi-spheric shank head 60, the elongate rod 4, the receiver 100, and the closure 190, can be the same as or substantially similar to those already described, so as to more completely provide the modular spinal fixation system 10 discussed above with respect to FIG. 1, with all its attendant features and benefits.

The receiver 100 of the monoaxial bone anchor assembly 40 illustrated in FIG. 95 can have substantially the same construction and features of the receiver of the multiplanar bone anchor assembly shown in FIGS. 7-10, and in one aspect the two embodiments of the receiver can be interchangeable or even identical. This is possible because the differences between the multiplanar bone anchor assemblies and the monoaxial bone anchor assembly 40 can be limited to the interface between the upper portions of the cap retainers and the lower portions of the pressure inserts, with the lower portions of the cap retainers (i.e. the partial spherical lower outer surface) and the upper portions of the pressure insets (i.e. the upper flanges and the opposite indexing nubs) interacting with the internal surfaces and/or structures of the central bore of the receiver in substantially the same way.

Figure 96:
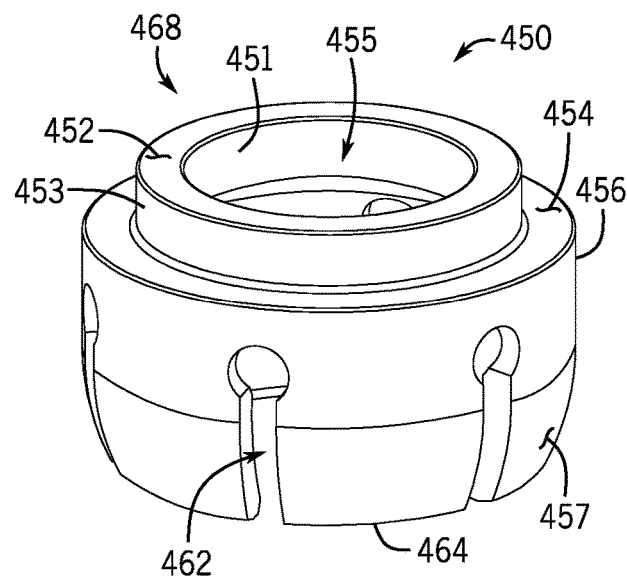
FIG. 96 is a top perspective view of the cap retainer of the monoaxial bone anchor assembly of FIG. 95.
Figure 97:
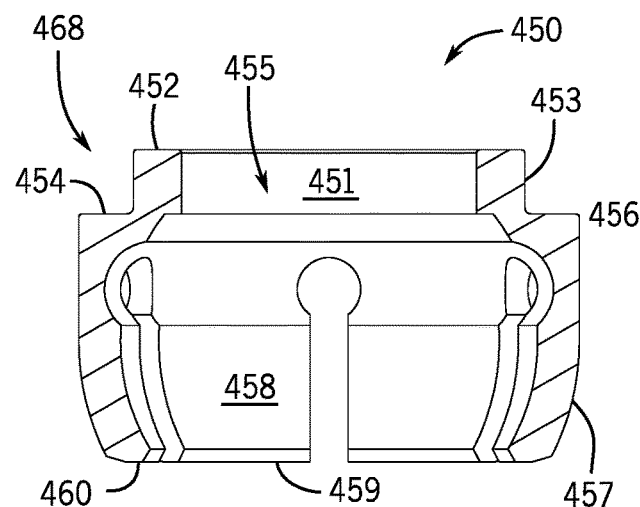
FIG. 97 is a cross-sectional side view of the cap retainer of FIG. 96.
Figure 98:
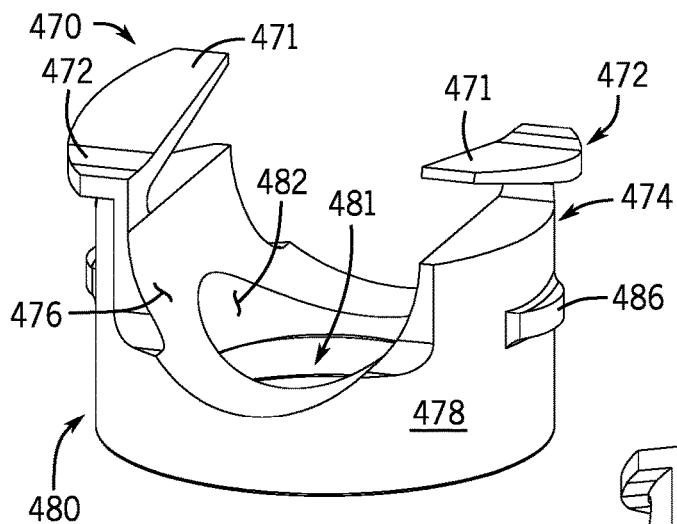
FIG. 98 is a top perspective view of the pressure insert of the monoaxial bone anchor assembly of FIG. 95.
Figure 99:
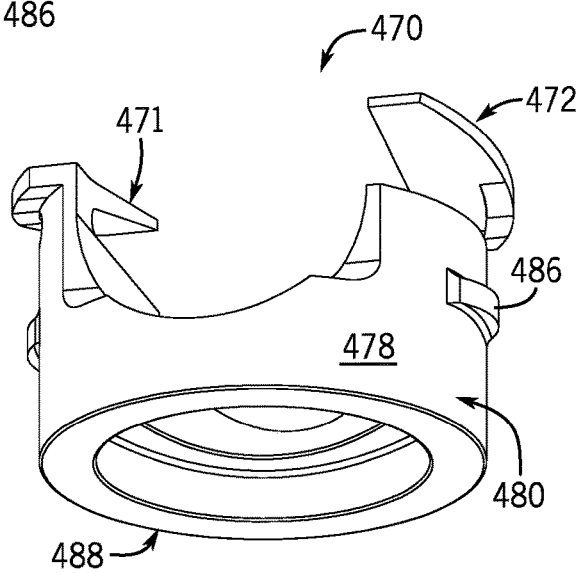
FIG. 99 is a bottom perspective view of the pressure insert of FIG. 98.
Figure 100:
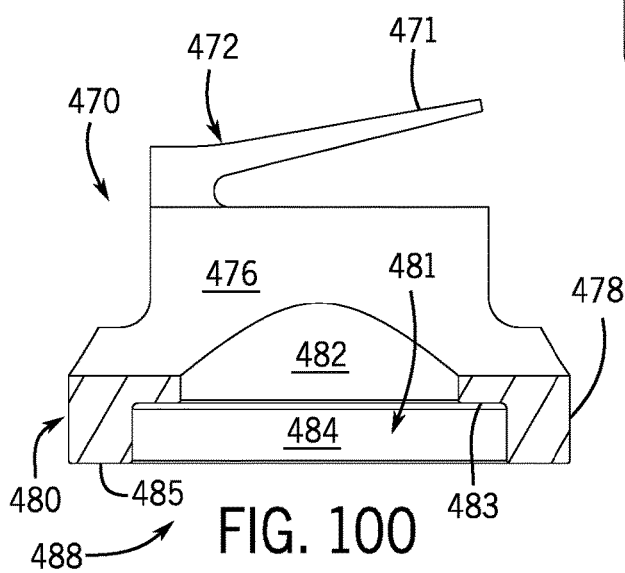
FIG. 100 is a cross-sectional side view of the pressure insert of FIG. 98.
Figure 101:
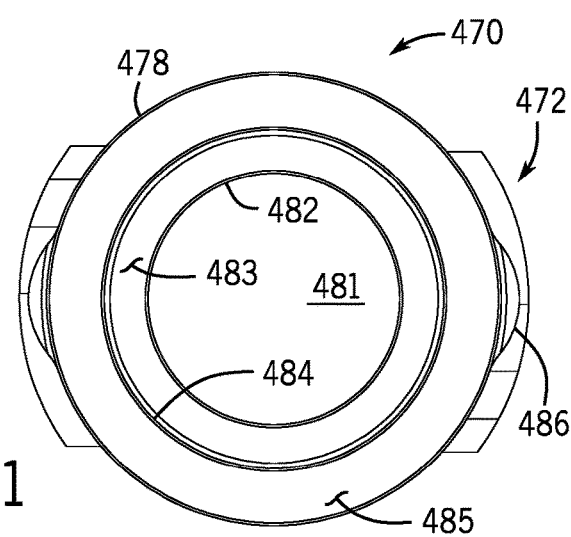
FIG. 101 is a bottom view of the pressure insert of FIG. 98.
Figure 102:
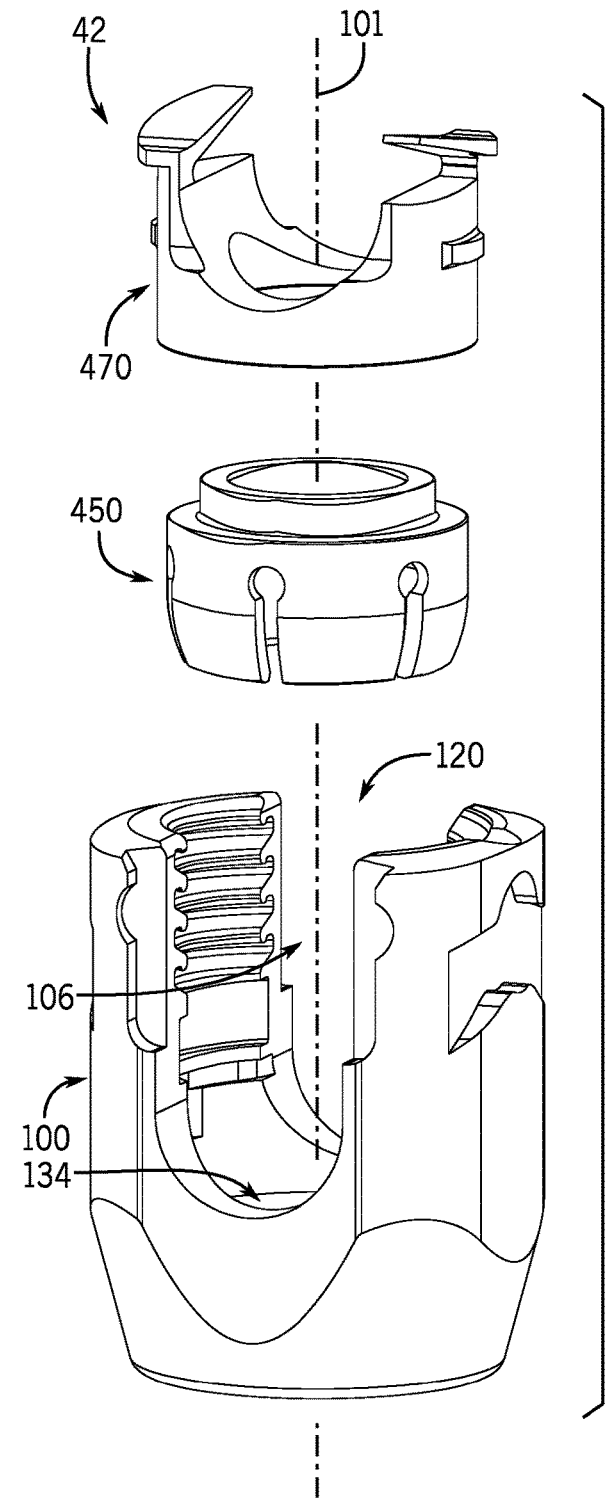
FIG. 102 is an exploded front perspective view of the components of the monoaxial receiver sub-assembly of FIG. 95 prior to their pre-assembly into a shipping configuration.

With reference to FIGS. 96-97, the construction and features of the monoaxial cap retainer 450 can differ from the multiplanar embodiment in that upper ring portion can be replaced with an upper stepped cylindrical structure 468 defined by an upward-facing inner step surface 452, an upward-facing outer step surface 454 located at a level below the inner step surface 452, an upper outer cylindrical surface 453 extending downward from the inner step surface 452 to the outer step surface 454. The upper stepped cylindrical structure 468 further includes an inner cylindrical surface 451 extending downward from the inner step surface 452 to define the upper center opening 455, and a partial cylindrical side surface 456 extending downward from the outer step surface 454 before transitioning into a discontinuous outer spherical surface 457 that continues downward toward the discontinuous bottom surface 460. In one aspect the partial cylindrical side surface 456 can have the same major diameter as the discontinuous outer spherical surface 457 that is slightly smaller than the diameter of the central bore 120 of the receiver 100, so that it can easily drop downward from the top of the receiver 100 to reach the spherical seating surface 136 adjacent the bottom opening 145 (FIGS. 7-10).

As described above, the upper stepped cylindrical structure 468 of the monoaxial cap retainer 450 can define the lower portion of a stepped cylindrical joint that can mate with the complementary lower stepped cylindrical structure 488 of the monoaxial pressure insert 470 to form a stepped cylindrical joint that allows for relative rotation between the cap retainer 450 and the pressure insert 470. Other aspects of the cap retainer 450 450, including the discontinuous inner spherical surface 458 extending downward from inner cylindrical surface 451 toward the discontinuous annular bottom surface 460, and the plurality of slots 462 formed through the thickness of the cap retainer 450 and extending upward from the annular bottom surface 460 toward the upper stepped cylindrical structure 468 to define the plurality of collet fingers 464, can be substantially the same as those of the multiplanar embodiment.

With reference to FIGS. 98-101, the monoaxial pressure insert 470 can have substantially the same construction and features of the first multiplanar embodiment described above, with the exception that the lower portions of the base portion 480 may be raised to accommodate the increased height of the partial cylindrical side surface and outer step surface of the monaxial cap retainer, and that the downwardly-opening concave lower surface can be replaced with a lower stepped cylindrical structure 488. In one aspect the lower stepped cylindrical structure 488 can include the inner cylindrical surface 482 defining the tool receiving aperture 481 and extending downward to the inner edge of a downwardly-facing inner stepped surface 483, an internal cylindrical surface 484 extending downward from the outer edge of the inner stepped surface 483 to a downwardly-facing bottom stepped surface 485 that, in turn, extends between the internal cylindrical surface 484 and the outer cylindrical surface 478. Other aspects of the pressure insert 470, including the resilient upper flanges 472 extending radially outward from the pair of insert arms 474, the upward-facing rod seating surface 476 extending between the insert arms 474 to define an insert channel 477, and the opposite indexing nubs 486, can be substantially the same as those of the first multiplanar embodiment.

Figure 103:
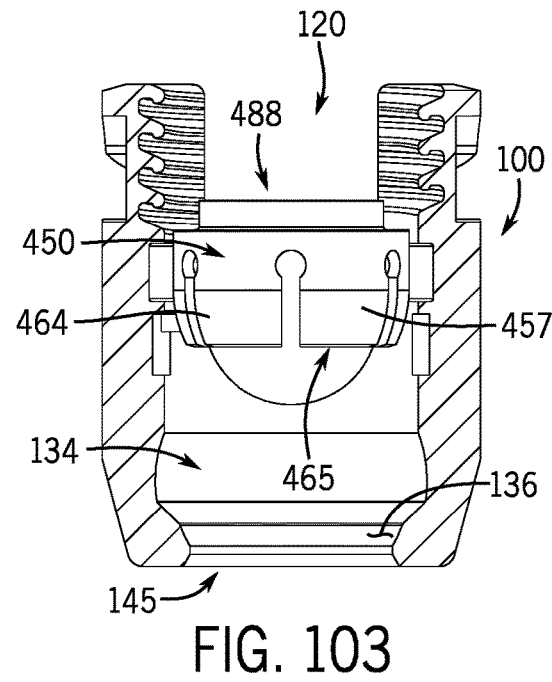
FIG. 103 is a partially cut-away front view of the receiver of FIG. 102 with the monoaxial cap retainer being downloaded through the open channel of the receiver.
Figure 104:
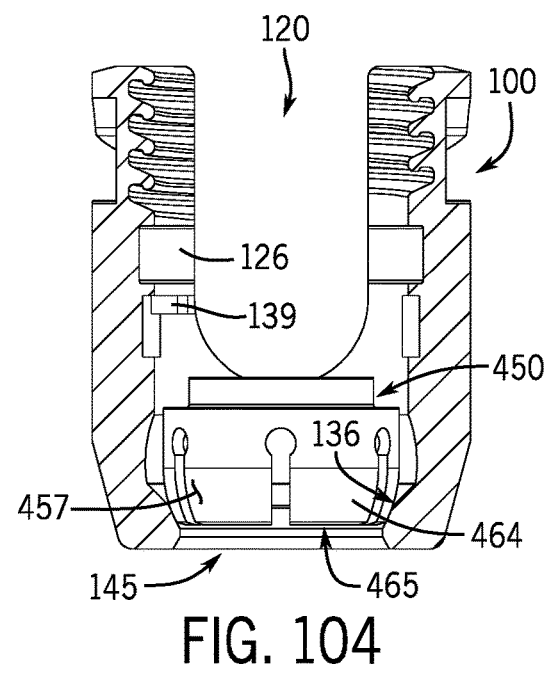
FIG. 104 is a partially cut-away front view of the receiver of FIG. 102 with the seated monoaxial cap retainer contacting the spherical seating surface of the receiver.

FIGS. 102 and 103-110 illustrate the pre-assembly of the basic receiver 100 with the monoaxial versions of the cap retainer 450 and the pressure insert 470 together to form the monoaxial receiver sub-assembly 42 in a self-biased shipping state configuration, which method of assembly can be substantially similar to that described above with respect to the multiplanar embodiments, but with a notable difference relating to the interaction between the lower stepped cylindrical structure 488 of the pressure insert 470 and the upper stepped cylindrical structure 468 of the cap retainer 450 to form the vertically-centered stepped cylindrical joint described above. As shown in FIGS. 103-104, the method can begin with top loading the cap retainer 450 downward through the central bore 120 of the receiver 100 until the discontinuous outer spherical surface 457 engages with the seating surface 136 at the lower end of the cavity 134 of the receiver, with the central lower opening 465 of the cap retainer 450 defined by the inner beveled edge surfaces of the collet fingers 464 being centered adjacent to and aligned with the bottom opening 145 of the receiver 100.

Figure 105:
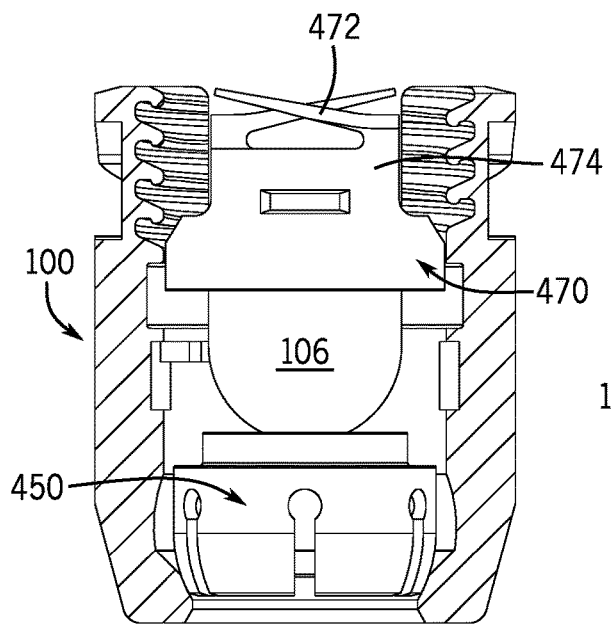
FIG. 105 is a partially cut-away front view of the receiver of FIG. 102, together with the seated monoaxial cap retainer and with the monoaxial pressure insert being downloaded through the open channel of the receiver.
Figure 106:
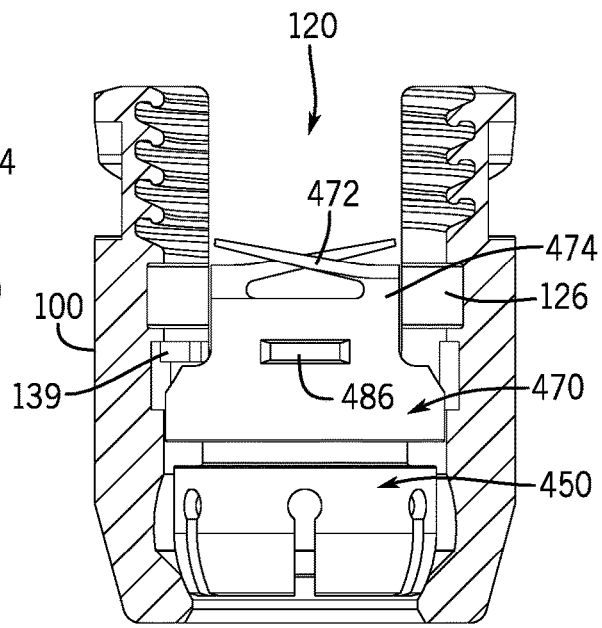
FIG. 106 is a partially cut-away front view of the receiver of FIG. 102, together with the seated monoaxial cap retainer and with the monoaxial pressure insert being further downloaded through the open channel of the receiver.

The monoaxial pressure insert 470 can then be top-loaded or down-loaded into the central bore 120 and installed into its the shipping state position above the cap retainer 450. As shown in FIGS. 105-106, this can be achieved by positioning the pressure insert 470 above the central bore 120 with the insert arms 474 and upper flanges 472 being aligned with the open channel 106, and then downloading the pressure insert 470 through the channel 106 (FIG. 105) until the leading edges of the upper flanges 472 reach the level of the discontinuous inner recess 126 formed into the central bore 120 for this type of twist-in-place axially biasing pressure insert, and the outwardly-projecting indexing nubs 486 reach the level of the horizontal access recesses 139 (FIG. 106). In this initial pre-rotation position the lower stepped cylindrical structure of the pressure insert 470 can still be spaced above the upper stepped cylindrical structure of the cap retainer 150.

Figure 107:
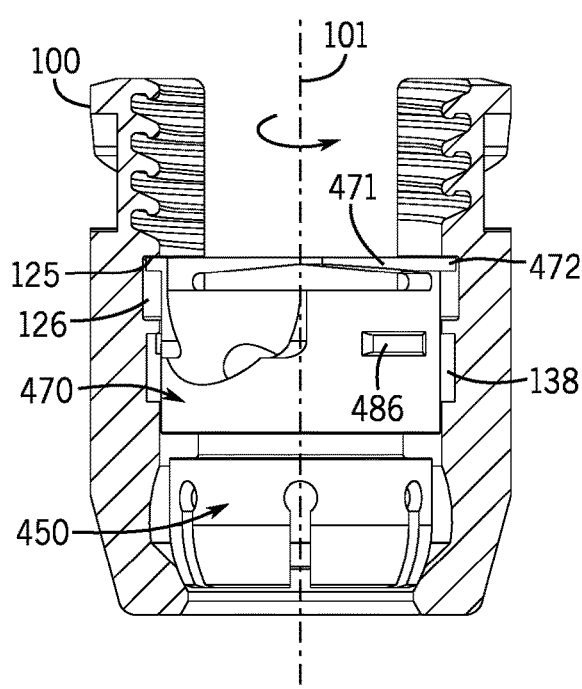
FIG. 107 is a partially cut-away front view of the receiver of FIG. 102, together with the seated monoaxial cap retainer and the downloaded and partially rotated monoaxial pressure insert.
Figure 108:
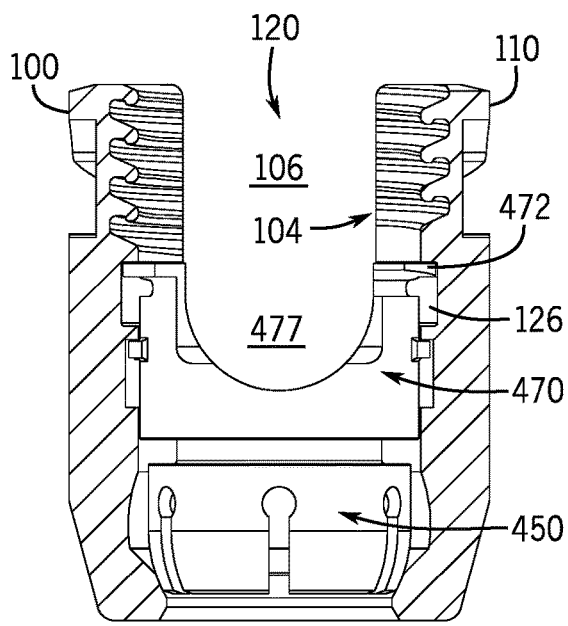
FIG. 108 is a partially cut-away front view of the receiver of FIG. 102, together with the seated monoaxial cap retainer and the downloaded and almost completely rotated monoaxial pressure insert.

The pressure insert 470 may then be rotated around its longitudinal axis (which is co-axial with the vertical centerline axis 101 of the receiver 100) so that the leading edges of the radially or outwardly-projecting and upwardly-angled upper flanges 472 enter into the discontinuous inner recess 126 of the upright arms 110 and the outwardly-projecting indexing nubs 486 enter the horizontal access recesses 139 (FIG. 107). Continued rotation of the pressure insert 470 can cause the top surfaces 471 of the upper flanges 472 to slidably resiliently engage with the downward-facing upper arcuate surfaces 125 of the discontinuous recess 126. Because the vertical location of the pressure insert 470 within the central bore 120 is temporarily fixed by the location of the indexing nubs 486 within the horizontal access recesses 139, this slidable engagement will cause the resilient upper flanges 472 to deflect downward under compression in order to enter the discontinuous recess 126, as shown in FIG. 107. The rotation of the pressure insert 470 can continue for a full 90 degrees or quarter turn, until the rod channel 477 of the insert 470 becomes aligned with the open channel 106 of the receiver 100, the compressed upper flanges become positioned within the discontinuous inner recess 126 of the interior faces 104 of the upright arms 110, and the indexing nubs 486 almost completely slide into the opposed vertical side pockets 138 of the central bore 120 (FIG. 108). It will be appreciated that the vertical position of the pressure insert 470 within the central bore 120 can be temporarily fixed, with the lower stepped cylindrical structure of the pressure insert 470 still spaced above the upper stepped cylindrical structure of the cap retainer 150, while the outwardly-projecting indexing nubs 486 are traveling along the horizontal access recesses 139.

Figure 109:
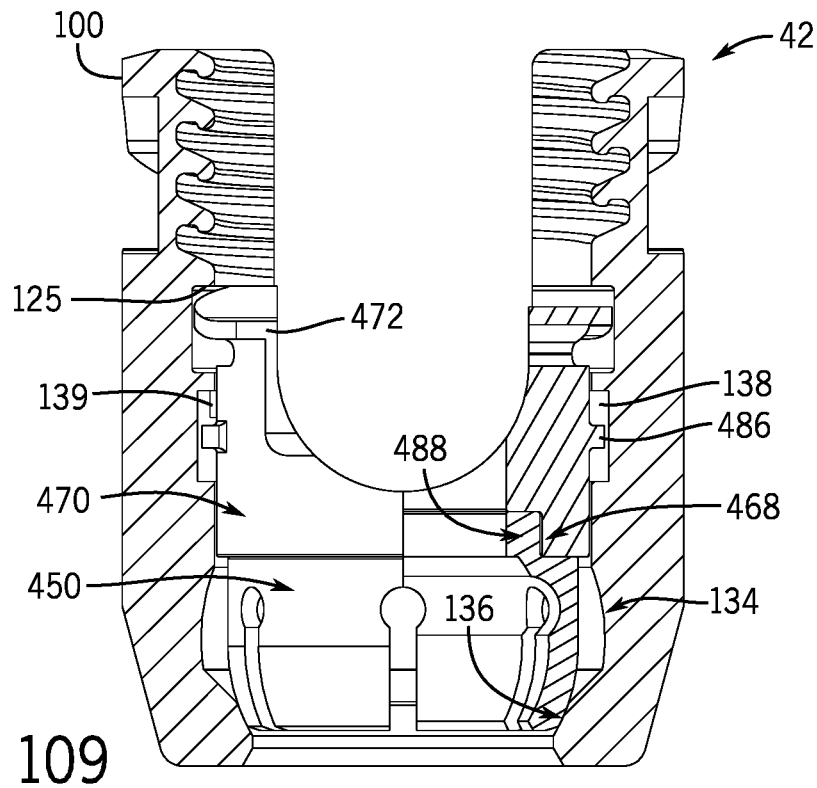
FIG. 109 is a partially cut-away front view of the receiver of FIG. 102, together with the seated monoaxial cap retainer and the monoaxial pressure insert being fully rotated therein and automatically deployed to form a pre-assembled monoaxial receiver sub-assembly in the shipping state configuration.
Figure 110:
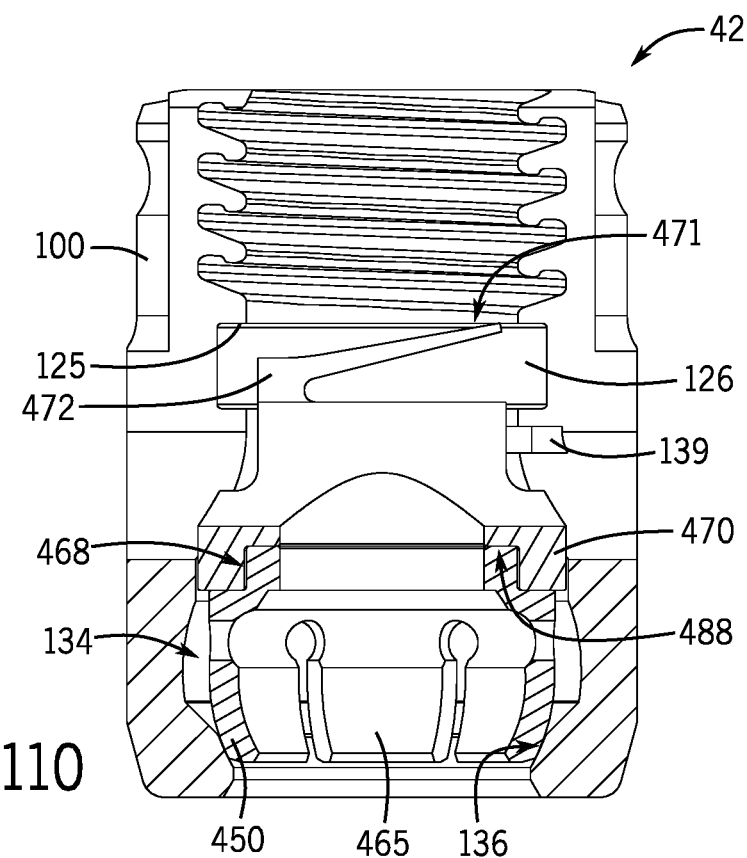
FIG. 110 is a partially cut-away side view of the monoaxial receiver sub-assembly of FIG. 109.

As soon as the indexing nubs 486 exit the horizontal access recesses 139 and completely enter into the opposed vertical side pockets 138, however, the compressed upper flanges 472 can release to drive the pressure insert 470 downward until the lower stepped cylindrical structure 488 engages the upper stepped cylindrical structure 468 of the cap retainer 450 to form the vertically-centered stepped cylindrical joint, as shown in FIGS. 109-110. The downward movement of the pressure insert 470 also causes the indexing nubs 486 to move downward within the side pockets 138 and below the horizontal access recesses 139, so that further engagement between the indexing nubs 486 and the sides of the vertically-aligned side pockets 138 can inhibit rotation the pressure insert 470, either clockwise or counter-clockwise, out of its rotated position. As with both the multiplanar and monoplanar embodiments described above, the continued compressive engagement between the upper flanges 472 and the receiver 100 can also bias the pressure insert 470 downwardly to engage and drive the cap retainer 450 downward against the seating surface 136 to establish the frictional engagement, or pre-lock friction fit, that can serve to inhibit subsequent rotation of the cap retainer 450 relative to the internal cavity 134 of the receiver 100. It will be appreciated that the stepped cylindrical joint between the lower stepped cylindrical structure 488 of the pressure insert 470 and the upper stepped cylindrical structure 468 of the cap retainer 450 can substantially prevent any pivotal motion of the cap retainer 450 relative to the internal cavity 334 of the receiver 100.

Thus, upon the monoaxial pressure insert 470 being rotated into its fully installed position within the receiver 100 above the monoaxial cap retainer 450, as shown in FIG. 109-110, so as to prevent both the pressure insert 470 and the cap retainer 450 from exiting the central bore 120 of the receiver 100, the pre-assembly of the monoaxial receiver sub-assembly 42 into its shipping state position or configuration is now complete. The monoaxial receiver sub-assembly 42 is now ready for storage and/or shipping and handling, and for eventual attachment to the bi-spheric shank head of a shank or bone anchor either prior to or during spinal surgery.

Figure 111:
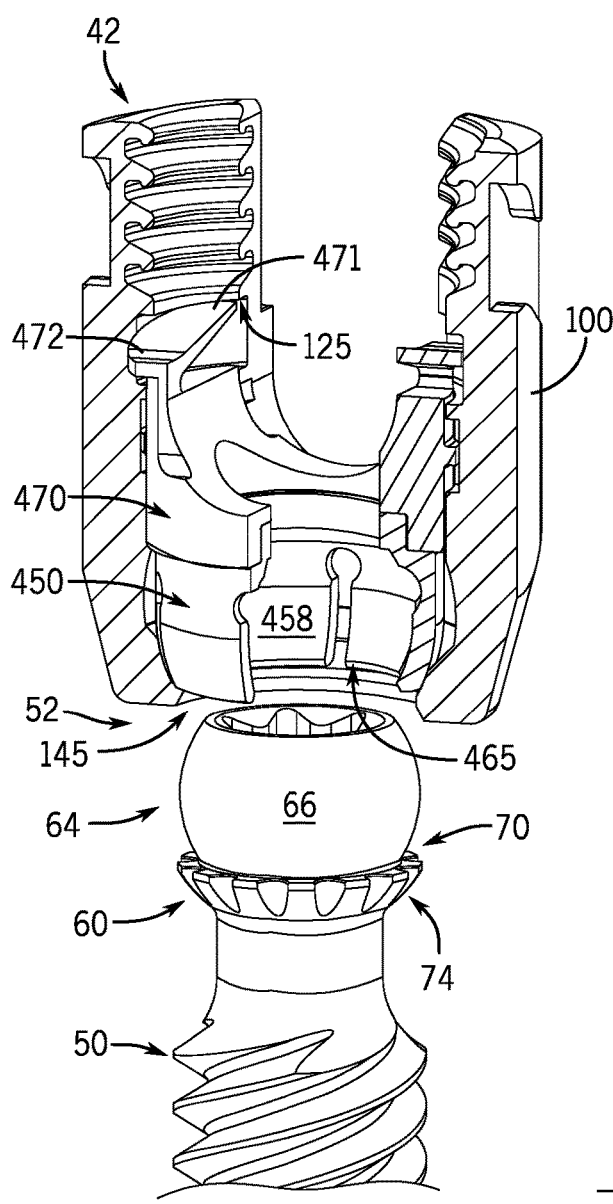
FIG. 111 is a partially cut-away front perspective view of the monoaxial receiver sub-assembly positioned above the bi-spheric shank head of the universal bone anchor.
Figure 112:
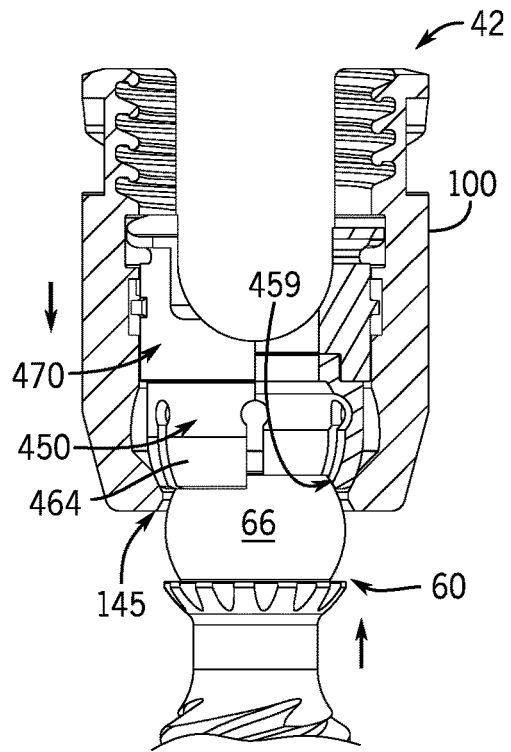
FIG. 112 is a partially cut-away front view of the monoaxial receiver sub-assembly moving downward until the bi-spheric shank head engages the cap retainer secured within the receiver by the pressure insert.

The assembly of the monoaxial receiver sub-assembly 42 of FIGS. 109-110 to the bi-spheric shank head 60 of the bone anchor 50 can be substantially similar to the assembly of the multiplanar embodiment discussed above in reference to FIGS. 29-42. For example, and with reference to the abbreviated sequence of assembly shown in FIGS. 111-119, the monoaxial receiver sub-assembly 42 can be first positioned above the proximal end 52 of the bone anchor 50, with the lower center aperture 465 of the monoaxial cap retainer 450, that is centered within the bottom opening 145 of the receiver 100, being generally aligned with the upper partial spherical portion 64 of the bi-spheric shank head 60 (FIG. 111). The monoaxial receiver sub-assembly 42 is then dropped downward (or the bone anchor 50 is moved upward, depending on the frame of reference of the reader) until the upper spherical surface 66 of the bi-spheric shank head 60 passes upward through the bottom opening 145 of the receiver 100 to engage the inner beveled edge surfaces 459 of the collet fingers 464 that define the central lower opening 465 (FIG. 112).

Figure 113:
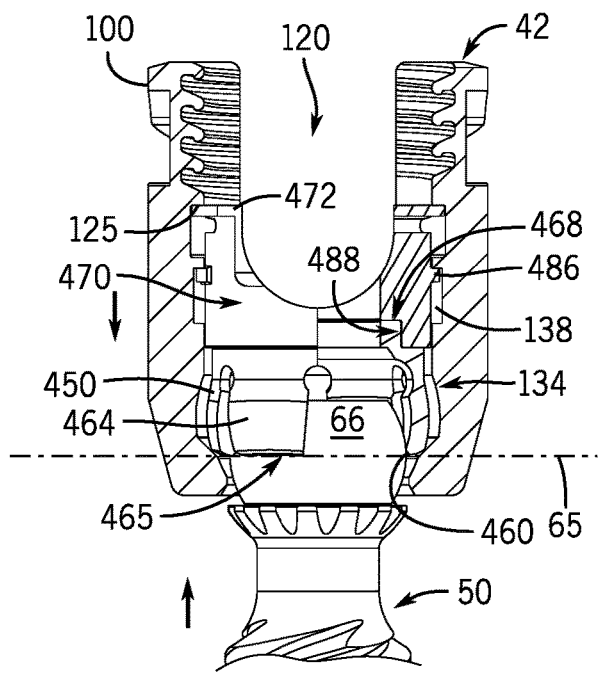
FIG. 113 is a partially cut-away front view of the monoaxial receiver sub-assembly continuing to move downward and the cap retainer and pressure insert being pushed upward to their uppermost positions, and the bi-spheric shank head continuing to drive upward as it expands the cap retainer within the internal cavity until reaching the maximum expansion of the cap retainer.

With reference to FIG. 113, the monoaxial receiver sub-assembly 42 continues to move downward (or the bone anchor moves upward) as the bi-spheric shank head 60 pushes both the cap retainer 450 and the pressure insert 470 upwards within the internal cavity 134 and the central bore 120 of the receiver, respectively, thereby compressing the resilient upper flanges 472 of the pressure insert 470 against the immovable upper arcuate surfaces 125 of the discontinuous recess 126. In one aspect the pressure insert 470 quickly reaches its uppermost position within the central bore 120 defined by the upper surfaces of the indexing nubs 486 abutting against the downward-facing upper surfaces of the vertical side pockets 138. At the same time, the central lower opening 465 of the cap retainer 450 begins to expand as it enters the upper expansion portion of the internal cavity 334, thereby allowing the inner beveled edge surfaces 459 of the collet fingers 464 of the cap retainer 450 to scrape downwards across the upper spherical surface 66 of the bi-spheric shank head 60.

With the pressure insert 470 now being fixed relative to the receiver 100, and the upper stepped cylindrical structure 468 of the cap retainer 450 being fixed against the complementary lower stepped cylindrical structure 488 of the pressure insert 470, the collet fingers 464 of the cap retainer 450 continue to be expanded within the expansion portion of the internal cavity 134 by the upward movement of the bi-spheric shank head 60 into the receiver 100. As shown in FIG. 113, the expansion of the cap retainer 450 can continue, with the discontinuous annular bottom surface 460 pushing any bone debris and/or soft tissue located on the upper spherical surface 66 downwards before it, until the discontinuous annular bottom surface reaches the hemisphere plane 65 of the bi-spheric shank head 60 and the cap retainer 450 is at its point of maximum expansion.

Figure 114:
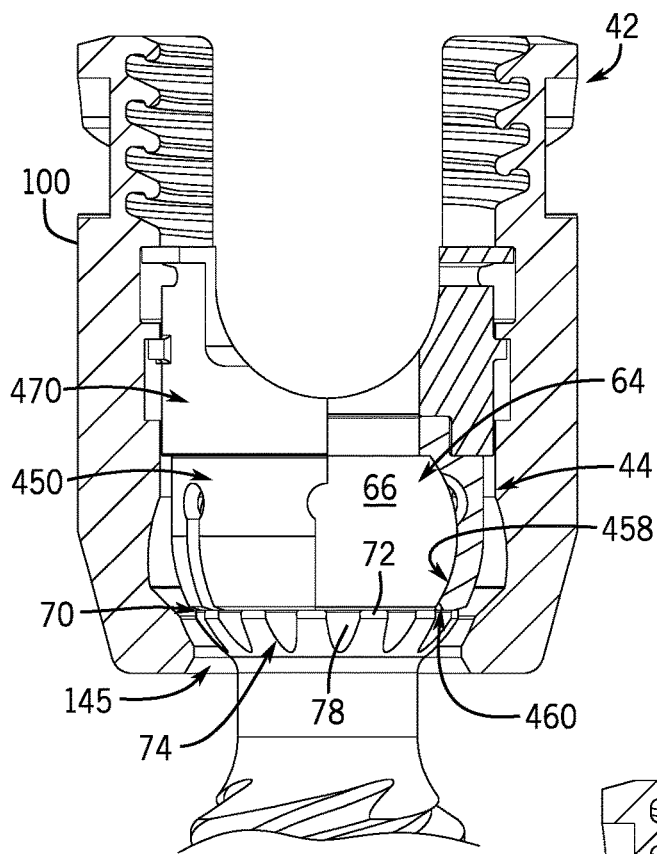
FIG. 114 is a partially cut-away front view of the monoaxial receiver sub-assembly continuing to move downward and the bi-spheric shank head continuing to drive upward until the bi-spheric shank head is completely captured by the cap retainer.

With reference to FIG. 114, the monoaxial receiver sub-assembly 42 continues to move downward (or the bone anchor moves upward) as the upper partial spherical portion 64 of the bi-spheric shank head 60 becomes fully captured by the cap retainer 450 as it contracts to close around the lower half of the upper partial spherical portion 64. During this motion, the discontinuous annular bottom surface 460 of the cap retainer 450 continues to push any bone debris and/or soft tissue downward toward the lower ledge 70 as the lower partial spherical portion 74 now moves upward into and through the bottom opening 145 of the receiver 100. Any bone debris and/or soft tissue that has been removed from the upper spherical surface 66 of the bi-spheric shank head 60 can pass through the plurality of open, vertically aligned flutes 78 that extend downwardly through and below the lower ledge 70 as the discontinuous annular bottom surface 460 engages the upward-facing surface 72 of the lower ledge 70. The discontinuous inner spherical surface 458 of the cap retainer 450 is now secured around the upper spherical surface 66 of the bi-spheric shank head 60, but with the stepped cylindrical joint between the cap retainer 450 and pressure insert 470 preventing any articulation of the monoaxial shank head sub-assembly 44 (i.e. the combined bi-spherical shank and the monoaxial cap retainer).

Figure 115:
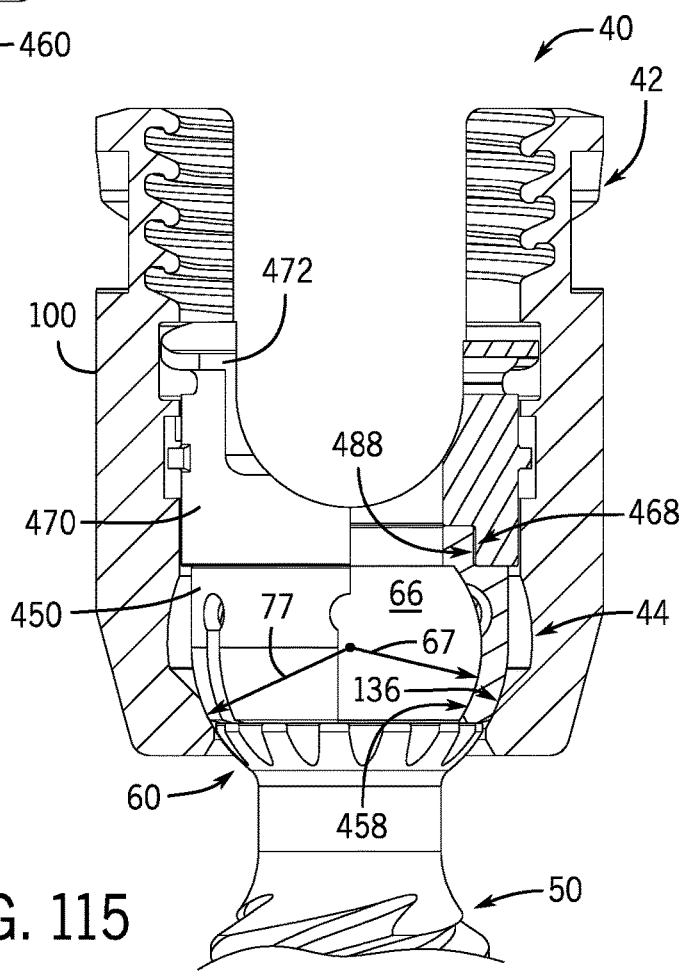
FIG. 115 is a partially cut-away front view of the monoaxial receiver sub-assembly with the uploading force being released and pressure insert being automatically downwardly deployed to push the monoaxial shank head sub-assembly back downward against the seating surface of the receiver to establish the initial configuration of the monoaxial bone anchor assembly in a pre-lock friction fit.

With reference to FIG. 115, the axially-directed forces used to upload the shank 50 to the monoaxial receiver sub-assembly 42 can now be released, which in turn releases the compressive load on the resilient upper flanges 472 of the pressure insert 470 and allows them to automatically push the pressure insert 470 and the non-articulating monoaxial shank head sub-assembly 44 downwardly until the cap retainer 450 (and the bi-spherical shank head) are re-secured against the seating surface 136 with a frictional engagement, or pre-lock friction fit, without any further manipulation or deployment of the pressure insert 470 with tooling.

With continued reference to FIG. 115, the frictional engagement at the interface at the minor diameter 67 between the spherical inner surface 458 of the cap retainer 450 and the outer spherical surface 66 of the bi-spheric shank head 60 can be stronger than any frictional engagement at the interface at the major diameter 77 between the discontinuous outer spherical surface 457 and the seating surface 136 of the receiver 100, and between the upper stepped cylindrical structure 468 and the lower stepped cylindrical structure 488 of the stepped cylindrical joint that may be provided by the axially-biasing pressure insert 470. As such, any rotational forces or moments created between the bi-spheric shank head 60 and the monoaxial receiver sub-assembly 42 can allow the non-articulating monoaxial shank head sub-assembly 44 to rotate or spin together within the internal cavity 134 of the receiver 100, even when the axially-biasing pressure insert 470 is providing the pre-lock friction fit.

As with the multiplanar embodiments described above, it is foreseen that both the receiver 100 and the monoaxial pressure insert can be reconfigured for manual downwardly deployment of the monoaxial pressure insert using tooling after the bi-spheric shank head 60 has been captured by the monoaxial cap retainer, so as to provide the pre-lock friction fit. For example, the monoaxial pressure insert can be provided with the opposite outwardly-projecting flanges that are moved downward from the opposed upper recesses to become engaged within the opposed lower recesses upon deployment of pressure insert with the tooling. In yet another alternative embodiment, both the monoaxial receiver and the monoaxial pressure insert can be reconfigured so that tooling may be used to temporarily hold the monoaxial pressure insert down in a biased or even in a temporarily locked position within the monoaxial receiver sub-assembly, until there is a final locking of the monoaxial bone anchor assembly with the elongate rod and via the closure.

Figure 116:
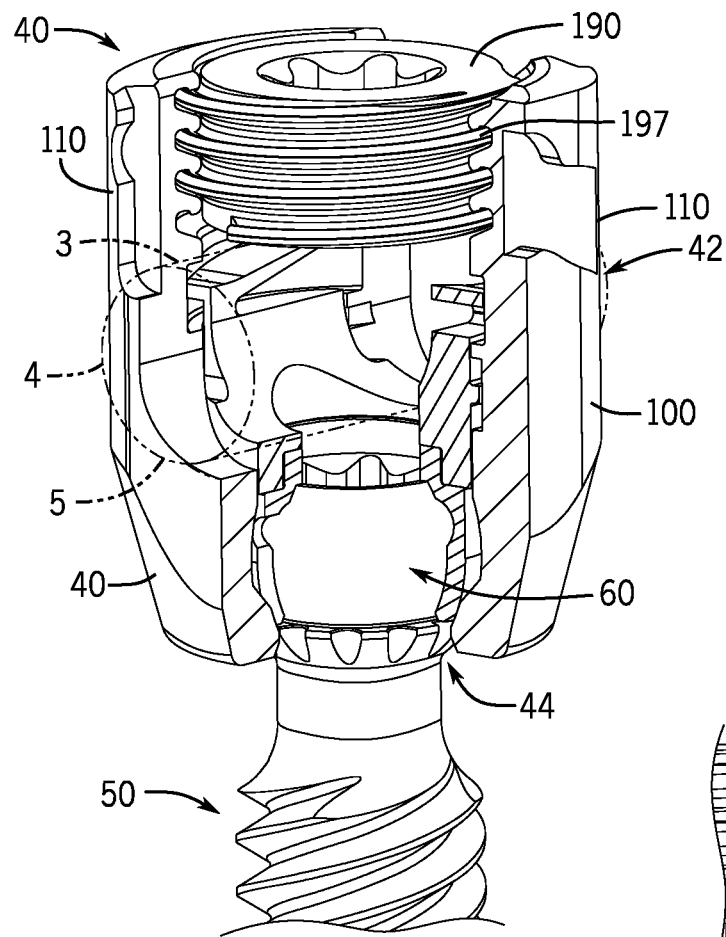
FIG. 116 is a partially cut-away front perspective view of the monoaxial bone anchor assembly, fully assembled with the elongate rod and closure and with the bone anchor in a non-articulated position relative to the receiver.
Figure 117:
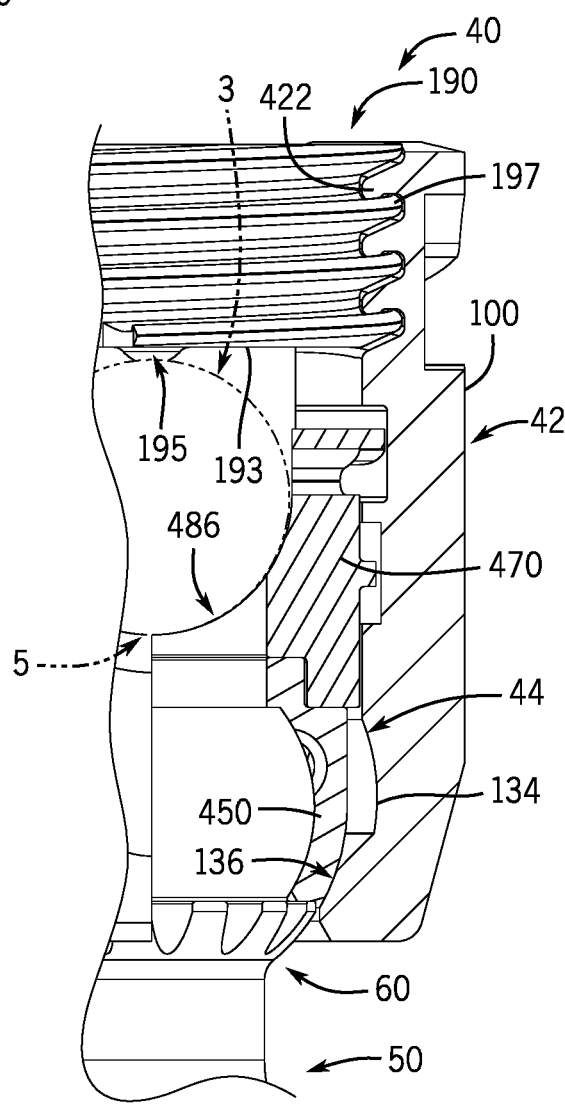
FIG. 117 is a close-up partially cut-away front view of a portion of the fully-assembled monoaxial bone anchor assembly of FIG. 116.

Illustrated in FIGS. 116-117 is the monoaxial bone anchor assembly 40 as fully assembled and locked with the elongate rod 4 and the single-piece closure 190. For instance, after a desired rotational-only alignment of the rod channel of the receiver 100 has been achieved via manipulation of the monoaxial receiver sub-assembly 42 relative to the shank head 60, with the axially-biased monoaxial insert 470 providing a pre-lock friction fit, the elongate rod 4 can be installed (i.e. reduced) into the rod channel, such as with instruments and/or breakoff extensions on the upright arms 110, until the lowermost or underside surface 5 of the elongate rod 4 approaches the upward-facing rod seating surface 486 of the pressure insert 470. The closure 190 can then be installed into the upper portion of the central bore of the receiver 100 (optionally using breakoff extensions), in which the outer continuous guide and advancement structure of the closure 197 rotatably engages the discontinuous guide and advancement structure 422 formed into the interior faces of the upright arms 110 of the receiver 100 (and the interior surfaces of the breakoff extensions, if present). The closure 190 can be threaded downwardly until the bottom surface 193 of the closure, or the downwardly-projecting central projection 195 protruding therefrom, engages the upper surface 3 of the elongate rod 4. Further rotation and torquing of the closure can then be used to drive the elongate rod downward onto the pressure insert 470, which in turn further drives the monoaxial shank head sub-assembly 44 downward onto the spherical seating surface 136 of the internal cavity of the receiver 100 to achieve a final locking of the monoaxial bone anchor assembly 40, in which the monoaxial receiver sub-assembly 42 can no longer pivot or rotate relative to the shank 50.

As indicated above, the spinal fixation system of the present disclosure has been described herein in terms of preferred embodiments and methodologies considered by the inventors to represent best modes of carrying out the one or more inventions disclosed herein. It will be understood by the skilled artisan, however, that a wide range of additions, deletions, and modifications, both subtle and gross, may be made to the illustrated embodiments of the pivotal and non-pivotal bone anchor assemblies, to the modular spinal fixation system, and to the representative type of bi-spherical universal shank head, and that these and other revisions might be made by those of skill in the art without departing from the spirit and scope of the one or more inventions that are to be constrained only by their respective claims.

What is claimed is:

1. A spinal fixation system for securing a fixation rod to a bone of a patient with a plurality of closures, the spinal fixation system comprising:
    a plurality of bone anchors, each bone anchor comprising
        a longitudinal axis, a shank head at a proximal end, and an anchor portion opposite the shank head configured for fixation to the bone, the shank head including:
            an upper partial spherical portion comprising an annular planar top surface at an upper end of the shank head and an upper spherical surface having a first diameter extending downward from the planar top surface past a hemisphere plane to a circular inner edge of an upward-facing ledge; and
            a lower partial spherical portion comprising a lower spherical surface having second diameter greater than the first diameter extending downward from a circular outer edge of the upward-facing ledge toward a neck portion that connects the shank head to the anchor portion; and a plurality of receiver sub-assemblies, each receiver sub-assembly including:
a receiver having a vertical centerline axis, an upper portion defining a channel configured to receive the fixation rod, and a base defining a lower portion of a central bore formed around the vertical centerline axis and communicating with a bottom surface of the receiver through a bottom opening, the central bore extending upwardly from the bottom opening through the channel to a top of the receiver and including a guide and advancement structure mateable with a closure proximate the top of the receiver and a seating surface adjacent the bottom opening;
a retaining structure positionable within the internal cavity having a discontinuous outer spherical surface configured to slidably engage the seating surface of the receiver, a discontinuous inner spherical surface configured to frictionally engage the upper spherical surface of the shank head, and a plurality of slots extending upward from a discontinuous annular bottom surface to form a plurality of collet fingers configured to resiliently expand to receive and capture the upper partial spherical portion of the shank head within the central bore when the shank head is uploaded through the bottom opening; and
a pressure insert positionable within the central bore above the retaining structure and having an upper surface configured to engage the elongate rod and a lower end configured to engage the retaining structure,
wherein each of the plurality of shank heads is configured for uploading into each of the plurality of receivers sub-assemblies through the bottom opening of the receiver, and for axial rotation about the longitudinal axis of the bone anchor relative to the receiver prior to locking the receiver sub-assembly to the shank head with the fixation rod and a closure.

2. The spinal fixation system of claim 1, wherein the seating surface of the receiver is a spherical seating surface.

3. The spinal fixation system of claim 1,
wherein the plurality of receiver sub-assemblies includes both pivoting and non-pivoting receiver sub-assemblies, and
wherein each of the shank heads is configured for uploading into both the pivoting and non-pivoting receiver sub-assemblies through the bottom opening of the receiver.

4. The spinal fixation system of claim 3, wherein the pivoting receiver sub-assemblies further comprise at least one multiplanar receiver sub-assembly and at least one monoplanar receiver sub-assembly.

5. The spinal fixation system of claim 3, wherein upper ends of the retaining structures and the lower ends of the pressure inserts of the non-pivoting receiver sub-assemblies are configured to form a stepped cylindrical joint when engaged together, with the retaining structures being rotatable about the vertical centerline axis of the receiver relative to the pressure inserts prior to locking the receiver assemblies to the shank heads.

6. The spinal fixation system of claim 1, wherein the shank head further comprises an internal drive structure surrounded by the annular planar top surface and extending downward from the upper end of the shank head and configured to mate with a drive tool.

7. The spinal fixation system of claim 6, wherein the bone anchor further comprises a shank body having an axial bore extending from the internal drive structure down to a distal end of the anchor portion and configured to receive a guide wire, the anchor portion of the shank body being configured for implantation in the bone about the guide wire with the drive tool prior to the shank head being uploaded into the central bore of the receiver.

8. The spinal fixation system of claim 1, wherein the discontinuous annular bottom surface of the retaining structure is configured to engage an upper ledge surface of the upward-facing ledge to align the retaining structure to the shank head when capturing the shank head within the central bore of the receiver.

9. The spinal fixation system of claim 8, wherein a diameter of the discontinuous outer spherical surface of the retaining structure is substantially equal to the second diameter of the lower spherical surface of the shank head to form a single diameter, articulating shank head sub-assembly having the second diameter that is greater than the diameter of the bottom opening of the receiver upon capturing the shank head within the central bore of the receiver.

10. The spinal fixation system of claim 8, wherein the retaining structure includes an annular planar upper surface that alignable flush with the annular planar top surface of the shank head upon capturing the shank head within the central bore of the receiver.

11. The spinal fixation system of claim 8, wherein the discontinuous annular bottom surface of the retaining structure and the upper ledge surface of the upward-facing ledge are substantially planar surfaces extending perpendicular to the longitudinal axis of the bone anchor.

12. The spinal fixation system of claim 1, wherein the upward-facing ledge and the lower partial spherical portion of the shank head include a plurality of open, vertically aligned flutes arranged circumferentially around the shank head and extending downwardly through and below the upward-facing ledge.

13. The spinal fixation system of claim 1, wherein the pressure insert further comprises an insert base, a pair of inserts arms extending upward from the insert base to define a channel configured to receive the elongate rod, and upper flanges projecting radially outward from upper portions of the insert arms with top surfaces configured to rotate under and resiliently engage downward-facing upper arcuate surfaces of a discontinuous recess formed into the central bore of the receiver so as to provide a downwardly-directed biasing force against the retaining structure.

14. The spinal fixation system of claim 13, wherein the upper flanges are formed integral with the pair of insert arms.

15. A spinal fixation system for securing a fixation rod to a bone of a patient with a plurality of closures, the spinal fixation system comprising:
a plurality of bone anchors, each bone anchor comprising a longitudinal axis, a shank head at a proximal end, and an anchor portion opposite the shank head configured for fixation to the bone, the shank head including:
an upper partial spherical portion comprising an annular planar top surface at an upper end of the shank head and an upper spherical surface having a first diameter extending downward from the planar top surface past a hemisphere plane to a circular inner edge of an upward-facing ledge; and
a lower partial spherical portion comprising a lower spherical surface having second diameter greater than the first diameter extending downward from a circular outer edge of the upward-facing ledge to a neck portion that connects the shank head to the anchor portion; and a plurality of pivoting and non-pivoting receiver sub-assemblies, each receiver sub-assembly including:

a receiver having a vertical centerline axis, an upper portion defining a channel configured to receive the fixation rod, and a base defining a lower portion of a central bore formed around the vertical centerline axis and communicating with a bottom surface of the receiver through a bottom opening, the central bore extending upwardly from the bottom opening through the channel to a top of the receiver and including a guide and advancement structure mateable with a closure proximate the top of the receiver and a spherical seating surface adjacent the bottom opening;

a retaining structure positionable within the internal cavity having a discontinuous outer spherical surface configured to slidably engage the seating surface of the receiver, a discontinuous inner spherical surface configured to frictionally engage the upper spherical surface of the shank head, and a plurality of slots extending upward from a discontinuous annular bottom surface to form a plurality of collet fingers configured to resiliently expand to receive and capture the shank head within the central bore when the shank head is uploaded through the bottom opening; and a pressure insert positionable within the central bore above the retaining structure and having an upper surface configured to engage the elongate rod and a lower end configured to engage an upper end of the retaining structure, wherein each of the plurality of shank heads is configured for uploading into both the pivoting and non-pivoting receiver sub-assemblies through the bottom opening of the receiver, and for axial rotation about the longitudinal axis of the bone anchor relative to the receiver prior to locking the receiver sub-assembly to the shank head with the fixation rod and a closure.

16. The spinal fixation system of claim 15, wherein the upper ends of the retaining structures and the lower ends of the pressure inserts of the non-pivoting receiver sub-assemblies are configured to form a stepped cylindrical joint when engaged together, with the retaining structures being rotatable about the vertical centerline axis of the receiver relative to the pressure inserts prior to locking the receiver assemblies to the shank heads.

17. The spinal fixation system of claim 15, wherein the pivoting receiver sub-assemblies further comprise at least one multiplanar receiver sub-assembly and at least one monoplanar receiver sub-assembly.

18. The spinal fixation system of claim 17, wherein a diameter of the discontinuous outer spherical surface of the retaining structure is substantially equal to the second diameter of the lower spherical surface of the shank head to form a single diameter, articulating shank head sub-assembly having the second diameter that is greater than the diameter of the bottom opening of the receiver upon capturing the shank head within the central bore of the receiver.

19. The spinal fixation system of claim 15, wherein the discontinuous annular bottom surface of the retaining structure is configured to engage an upper ledge surface of the upward-facing ledge to align the retaining structure to the shank head when capturing the shank head within the central bore of the receiver.

20. The spinal fixation system of claim 15, wherein the upward-facing ledge and the lower partial spherical portion of the shank head include a plurality of open, vertically aligned flutes arranged circumferentially around the shank head and extending downwardly through and below the upward-facing ledge.

21. The spinal fixation system of claim 15, wherein the pressure insert further comprises an insert base, a pair of inserts arms extending upward from the insert base to define a channel configured to receive the elongate rod, and integral upper flanges projecting upward and radially outward from upper portions of the insert arms with top surfaces configured to rotate under and resiliently engage downward-facing upper arcuate surfaces of a discontinuous recess formed into the central bore of the receiver so as to provide a downwardly-directed biasing force against the retaining structure.

* * * * *